US008648076B2

(12) United States Patent
Guedat et al.

(10) Patent No.: US 8,648,076 B2
(45) Date of Patent: Feb. 11, 2014

(54) CYSTEINE PROTEASE INHIBITORS AND THEIR THERAPEUTIC APPLICATIONS

(75) Inventors: Philippe Guedat, Montenois (FR);
Guillaume Boissy, Vincennes (FR);
Catherine Borg-Capra, Surenes (FR);
Frédéric Colland, Puiseux en France (FR); Laurent Daviet, Vetraz Monthoux (FR); Etienne Formstecher, Paris (FR); Xavier Jacq, Paris (FR);
Jean-Christophe Rain, Ermont (FR);
Rémi Delansorne, Paris (FR); Stefania Vallese, Gallarate (IT); Matteo Colombo, Camnago (IT)

(73) Assignee: Hybrigenics SA, Paris (FR)

( * ) Notice: Subject to any disclaimer, the term of this patent is extended or adjusted under 35 U.S.C. 154(b) by 1061 days.

(21) Appl. No.: 11/997,765

(22) PCT Filed: Jul. 26, 2006

(86) PCT No.: PCT/IB2006/002637
§ 371 (c)(1),
(2), (4) Date: Dec. 11, 2008

(87) PCT Pub. No.: WO2007/017758
PCT Pub. Date: Feb. 15, 2007

(65) Prior Publication Data
US 2009/0215786 A1    Aug. 27, 2009

Related U.S. Application Data

(63) Continuation of application No. 11/197,525, filed on Aug. 5, 2005.

(30) Foreign Application Priority Data

Aug. 5, 2005  (EP) .................................. 05291683

(51) Int. Cl.
*A01N 43/58* (2006.01)
*A01N 43/60* (2006.01)
*A61K 31/50* (2006.01)
*A61K 31/495* (2006.01)
*C07D 471/00* (2006.01)
*C07D 487/00* (2006.01)

(52) U.S. Cl.
USPC .......................................... 514/250; 544/344

(58) Field of Classification Search
None
See application file for complete search history.

(56) References Cited

U.S. PATENT DOCUMENTS

| 5,460,909 A | * | 10/1995 | Shoshi et al. .............. 430/58.25 |
| 6,103,720 A | | 8/2000 | Lubisch et al. |
| 2004/0109690 A1 | | 6/2004 | Maeda |
| 2004/0198716 A1 | | 10/2004 | Arad et al. |

FOREIGN PATENT DOCUMENTS

| JP | 6345742 | 12/1994 |
| JP | 7098508 | 4/1995 |
| JP | 7175235 | 7/1995 |
| JP | 7179440 | 7/1995 |
| JP | 7199486 | 8/1995 |
| JP | 7199487 | 8/1995 |
| JP | 7281460 | 10/1995 |
| JP | 2001028885 | 1/2001 |
| WO | WO 03048123 | 6/2003 |
| WO | WO 03055853 | 7/2003 |
| WO | WO 2004/022526 | 3/2004 |

OTHER PUBLICATIONS

Chawla et. al.; Current Research & Information on Pharmaceutical Science, 2004, 5(1), p. 9-12.*
Newman et. al.; Drug Discovery Today, 2003, 8(19) p. 898-905.*
Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Grigg, et. al. Tetrahedron Letters, (1990), 31(49), 7215-18.*
Popp, Frank D., Journal of Heterocyclic Chemistry (1972), 9(6), 1399-401.*
Schoeni, et al., "Nouvelles vois d'accès à des amino-2-pyrazines substituées", Helvetica Chimica Acta, vol. 69 (1986).
Lang, At Al., "Nouvelle Synthese Univoque d'Aminopyrazines", Tetrahedron Letters No. 45, pp. 3967-3970, 1974. Pergamon Press. Great Britain.
Lang et al., "Tetrahedron Letters," 1974, pp. 3967-3970, vol. 45, No. 15.
Tsuda et al, "Synthesis of New Pyrazine Compounds from Diaminomaleonitrile", 1978, pp. 213-217, vol. 52, No. 5, Nippon Nogei Kagaku Kaishi.
Sato et al., "Studies on Pyrazine. 23[1]. Homolytic Acylation of 2-Amino-3-cyanopyrazine and the Related Compounds with a-Keto Acids: A Synthesis of 5-Acyl-3-aminopyrazinecarboxylic Acid Derivatives", 1992, pp. 1685-1688, vol. 29, No. 7, Journal of Heterocyclic Chemistry.
English Translation of Japanese Office Action in Corresponding JP Application No. 2008-524625.

* cited by examiner

*Primary Examiner* — Jeffrey Murray
(74) *Attorney, Agent, or Firm* — Steven J. Weyer; Stites & Harbison, PLLC

(57) ABSTRACT

The present invention concerns new compounds of formula (I), their process of preparation and their therapeutic use.

20 Claims, No Drawings

CYSTEINE PROTEASE INHIBITORS AND THEIR THERAPEUTIC APPLICATIONS

This application is a continuation of application Ser. No. 11/197,525, filed Aug. 5, 2005 (which is hereby incorporated by reference).

The present invention concerns new inhibitors of cysteine proteases, their process of preparation and their therapeutic use.

Protease can be categorized based on their substrate specificities or mechanisms of catalysis. Upon the basis of the mechanism of peptide hydrolysis, five major protease classes are known: serine, cysteine, aspartic, threonine and metalloproteases. Cysteine proteases comprise, inter allia, de-ubiquitination enzymes, caspases, cathepsins, calpains as well as viral, bacterial or parasitic cysteine proteases.

De-ubiquitination enzymes include Ubiquitin Specific Proteases (USPs) and Ubiquitin Carboxy Hydrolases (UCHs). Broadly speaking, the ubiquitin pathway regulates protein degradation and is more particularly involved in cancer, in neurodegenerative diseases such as Alzheimer's disease, Parkinson's disease, in inflammation, in viral infectivity and latency (in particular for Herpes simplex virus-1, Epstein-Barr virus, SARS coronavirus), or in cardiovascular diseases (*Chem. Rev.* 1997, 97, p. 133-171; *Chem. Rev.* 2002, 102, p. 4459-4488; *J. Biochem.* 2003, 134, p. 9-18; *J. Virology*, 2005, 79(7), p. 4550-4551; *Cardiovasc. Res.* 2004, 61, p. 11-21).

Caspases have been shown to be involved in apoptosis and hence are targets in hepatitis, liver failure, inflammation, cardiac ischemia and failure, renal failure, neurodegeneration, deafness, diabetes, or stroke (*J. Pharmacol Exp. Ther.*, 2004, 308(3), p. 1191-1196, *J. Cell. Physiol.*, 2004, 200(2), p. 177-200; *Kidney Int*, 2004, 66(2), p. 500-506; *Am. J. Pathol.*, 2004, 165(2), p. 353-355; *Mini Rev. Chem.*, 2004, 4(2), p. 153-165; *Otol. Neurotol.*, 2004, 25(4), p. 627-632; Ref. 7, 21, 22, 23, 24, 25.

Cathepsins generally have been shown to be involved in cancer and metastasis, inflammation, immunology/immunoregulation (*Eur. Respir. J.*, 2004, 23(4), p. 620-628) and atherosclerosis (*Ageing Res. Rev.* 2003, 2(4), p. 407-418). More particularly, cathepsins include cathepsin B and B-like which are implicated in cancer and metastasis, and arthritis (*Cancer Metastasis Rev.*, 2003, 22(2-3), p. 271-286; *Biol. Chem.*, 2003, 384(6), p. 845-854 and *Biochem. Soc. Symp.*, 2003, 70, p. 263-276), cathepsin D, involved in particular in cancer and metastasis (*Clin. Exp. Metastasis*, 2004, 21(2), p. 91-106), cathepsin K acting in osteoporosis and arthritis (*Int. J. Pharm.*, 2004, 277(1-2), p. 73-79), cathepsin S which has been shown to play a role in antigen presentation in immunology (*Drug News Perspective*, 2004, 17(6), p. 357-363).

Calpains play a role in aging in general (*Ageing Res. Rev.* 2003, 2(4), p. 407-418), as well as diabetes (*Mol. Cell. Biochem.*, 2004, 261(1), p. 161-167) and cataract (*Trends Mol. Med.*, 2004, 10(2), p. 78-84) more particularly.

Viral cysteine proteases have been identified in rhinoviruses, poliomyelitis virus, hepatitis A virus, hepatitis C virus, adenovirus, or SARS coronavirus (*Chem. Rev.* 1997, 97, p. 133-171; *Chem. Rev.* 2002, 102, p. 4459-4488; *J. Virology*, 2005, 79(7), p. 4550-4551 and *Acta Microbiol. Immunol. Hung.*, 2003, 50(1), p. 95-101).

Bacterial cysteine proteases include streptopain, staphylococcal cysteine protease, clostripain or gingipains; yeasts such as *Aspergillus flavus* have also been shown to express cysteine proteases which may constitute a virulence factor (*Chem. Rev.* 1997, 97, p. 133-171).

Parasitic cysteine proteases have been reviewed in *Molecular & Biochemical Parasitology* (2002, 120, p. 1-21) and *Chem. Rev.* (2002, 102, p. 4459-4488) for example. It is worth noting that the parasitic agents responsible for most major parasitic diseases are making use of their own cysteine proteases at some point or another of their infective, nutritive or reproductive cycles; such diseases include malaria, Chagas' disease, African trypanosomiasis, leishmaniasis, giardiasis, trichomoniasis, amoebiasis, crypto-sporidiasis, toxoplamiasis, schistosomiasis, fasciolasis, onchocercosis, and other infections by some other flat or round worms.

Therefore, identifying a novel class of inhibitors of cysteine proteases is of significant importance in a wide range of diseases and pathological conditions.

Cyano-pyrazine derivatives have been disclosed, mainly as charge-transporting agents for electrophotographic photoreceptors (WO03/055853, JP200128885, JP200122316, JP07281460, JP07179440, JP07098508, JP06345742, JP07175235, JP07199487, JP07199486, JP07281460 and *Helvetica Chemica Acta*, 1986, 69(4), 793-802, *Tetrahedron Letters* 1974, 45, 3967-70, *J. Heterocyclic Chemistry*, 1972, 9(6), 1399-401, *Tetrahedron Letters*, 1990, 31(49), 7215-18). However, it has never been disclosed nor suggested that cyano-pyrazine derivatives can inhibit cysteine proteases.

According to a first object, the present invention concerns a compound of formula (I):

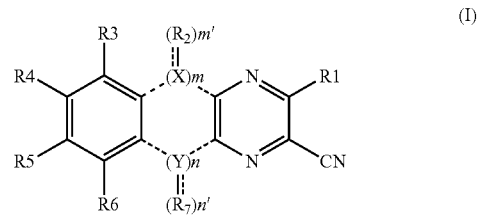

wherein:
m is 0; 1 or 2, wherein when m=0, —(X(R2)$_{m'}$)$_m$— is none so as to form an open ring or a single bond;
n is 0, 1 or 2, wherein when n=0, —(Y(R7)$_{n'}$)$_n$— is none so as to form an open ring or a single bond;
m' and n' are independently 0, 1 or 2;
X is a carbon atom or S or N;
Y is a carbon atom, or S or N;
Provided m and n are not simultaneously 0; - - - - -
is either a single or double bond, as appropriate;
— is either none or a single bond, as appropriate;
R1 is chosen from the group consisting in H, CN, Hal, OAlk, OH, NRCN, C(CN)=C(OH)(OAlk), SR, NRR', (Alk)$_p$-C(O) NRR', Heterocycle, Aryle, Heteroaryle, where Alk, Aryle, Heteroaryle, heterocycle are optionally substituted by Hal, NRR', CN, OH, CF$_3$, Aryle, Heteroaryle, OAlk, Where p is 0 or 1;
R3, R4, R5, R6 are each identical or different and are independently chosen from the group consisting in H, OAlk, Alk, Hal, NRR', CN, OH, CF$_3$, Aryle, Heteroaryle;
R2 is chosen from the group consisting in H, O, OH, N—OH, N-Aryle, N—OAlk, N—O-Aryle, N—O-Alk-Aryle, N—NR—CONRR', N—O—CO-Alk, or 2 R2 bound at the same X form together with that X an heterocycle; wherein said Alk, Aryle or heterocycle are optionally substituted by OAlk, Alk, Hal, NRR', CN, OH, CF$_3$, OAryl, —CO—(NR-Alk-CO)$_{p'}$—OAlk, —CO(NR-Alk-CO)$_{p'}$—OH,
Where p' is 0 or 1;

R7 is chosen from the group consisting in H, O, OH, N—OH, N-Aryle, N—OAlk, N—O-Aryle, N—O-Alk-Aryle, N—NR—CONRR', N—O—CO-Alk, or 2 R7 bound at the same Y form together with that Y an heterocycle; wherein said Alk, Aryle or heterocycle are optionally substituted by OAlk, Alk, Hal, NRR', CN, OH, $CF_3$, OAryl, —CO—(NR-Alk-CO)$_{p'}$—OAlk, —CO(NR-Alk-CO)$_{p'}$—OH,
Where p' is 0 or 1;
R and R' are each identical or different and are independently chosen from the group consisting in H, Alk, wherein Alk is optionally substituted by Hal, NRR', CN, OH, $CF_3$, Aryle, Heteroaryle;
or their pharmaceutically acceptable salts, hydrates, or hydrated salts, or the polymorphic crystalline structures of these compounds or their optical isomers, racemates, diastereomers or enantiomers,
with the exception of compounds where:
R3, R4, R5, R6=H, R1=CN, —(X(R2)$_{m'}$)$_m$- represents a single bond, and —(Y(R7)$_{n'}$)$_n$- represents —C(=N—OH)— or —C(=N-(2-,4-,6-trimethylphenyl))-, —C(=N-(2-,6-dimethylphenyl))-, —C(=N-(2-,6-diethylphenyl))-, —C(=N-(2-methyl-phenyl))-, —C(=N-(2-ethylphenyl))-, —C(=N-(2-trifluoromethylphenyl))-, —C(=N-(2-isopropylphenyl))-, —C(=N-phenyl)-, —C(=N-(naphtyl)- or —C(=O)—, —CH$_2$—, or
R3, R5, R6=H, R4=OMe, R1=CN, —(X(R2)$_{m'}$)$_m$- represents a single bond, and —(Y(R7)$_{n'}$)$_n$- represents —C(=O)—, or
R3, R4, R6=H, R5=OMe, R1=CN, —(X(R2)$_{m'}$)$_m$- represents a single bond, and —(Y(R7)$_{n'}$)$_n$- represents —C(=O)—, or
R3, R4, R5, R6=H, R1=NH$_2$, —(X(R2)$_{m'}$)$_m$- represents a single bond, and —(Y(R7)$_{n'}$)$_n$- represents —CH2- or —CH2-CH2-; or
R3, R4, R5, R6=H, R1=NH2, —(X(R2)$_{m'}$)$_m$- represents —CH2- or —CH2-CH2- and —(Y(R7)$_{n'}$)$_n$- represents a single bond.

Preferably, the compounds of the invention are defined as above, preferably with the exception of compounds where:
R3, R4, R5, R6=H, R1=CN, —(X(R2)$_{m'}$)$_m$- represents a single bond, and —(Y(R7)$_{n'}$)$_n$- represents —C(=N-(2-,4-,6-trimethylphenyl))-, —C(=N-(2-,6-dimethylphenyl))-, —C(=N-(2-,6-diethylphenyl))-, —C(=N-(2-methylphenyl))-, —C(=N-(2-ethyl-phenyl))-, —C(=N-(2-trifluoromethylphenyl))-, —C(=N-(2-iso-propylphenyl))-, —C(=N-phenyl)-, —C(=N-(naphtyl)- or —C(=O)—, —CH2-, or
R3, R5, R6=H, R4=OMe, R1=CN, —(X(R2)$_{m'}$)$_m$- represents a single bond, and —(Y(R7)$_{n'}$)$_n$- represents —C(=O)—, or
R3, R4, R6=H, R5=OMe, R1=CN, —(X(R2)$_{m'}$)$_m$- represents a single bond, and —(Y(R7)$_{n'}$)$_n$- represents —C(=O)—, or
R3, R4, R5, R6=H, R1=NH2, —(X(R2)$_{m'}$)$_m$- represents a single bond, and —(Y(R7)$_{n'}$)$_n$- represents —CH2-; or
R3, R4, R5, R6=H, R1=NH2, —(X(R2)$_{m'}$)$_m$- represents —CH2- and —(Y(R7)$_{n'}$)$_n$- represents a single bond.

Preferably, R1 is chosen from the group consisting in H, CN, Hal, OAlk, OH, NRCN, C(CN)=C(OH)(OAlk), SR, NRR', C(O)NRR', Heterocycle, where Alk is optionally substituted by OAlk and where Heterocycle is optionally substituted by Hal.

Preferably, R3, R4, R5, R6 are each identical or different and are independently chosen from the group consisting in H, OAlk, OH, Alk, Hal.

Preferably, —(Y(R7)$_{n'}$)$_n$- is a single bond or Y represents a carbon atom or a S atom.

Preferably, —(X(R2)$_{m'}$)$_m$- represents a single bond.

Preferably, R2 is chosen from the group consisting in H, O.

Preferably, R7 is chosen from the group consisting in H, O, OH, N—OH, N—OAlk, N-Aryle, N—O-Aryle or N—O-Alk-Aryle, N—O-Alk-Oaryle, N—O-Alk-CO—(NR-Alk-CO)$_{p'}$—OAlk, N—O-Alk-CO(NR-Alk-CO)$_{p'}$—OH, N—NR—CO—NRR', N—O—CO-Alk or 2 R7 bound at the same Y form together with that Y an heterocycle, where p' is 0 or 1.

Preferably, R and R' are each identical or different and are independently chosen from the group consisting in H, Alk.

More preferably, in formula (I), —(X(R2)$_{m'}$)$_m$- represents a single bond, n is 1, n' is 1, Y is a carbon atom;
R1 is chosen from the group consisting in H, CN, Hal, OAlk, OH, NRCN, C(CN)=C(OH)(OAlk), SR, NRR', C(O)NRR', Heterocycle, where Alk is optionally substituted by OAlk and where Heterocycle is optionally substituted by Hal;
R3, R4, R5, R6 are each identical or different and are independently chosen from the group consisting in H, OAlk, OH, Alk, Hal;
R7 is chosen from the group consisting in O, N—OH, N—OAlk, N-Aryle, N—O-Aryle or N—O-Alk-Aryle;
R and R' are each identical or different and are independently chosen from the group consisting in H, Alk;
or their pharmaceutically acceptable salts, hydrates, or hydrated salts, or the polymorphic crystalline structures of these compounds or their optical isomers, racemates, diastereomers or enantiomers.

Preferred compounds of the invention are chosen from the group consisting in:
9-hydroxy-3-methoxy-9H-indeno[1,2-b]pyrazine-2-carbonitrile
3-methoxy-9-oxo-9H-indeno[1,2-b]pyrazine-2-carbonitrile
3-dimethylamino-9-oxo-9H-indeno[1,2-b]pyrazine-2-carbonitrile
3-(2-methoxy-ethoxy)-9-oxo-9H-indeno[1,2-b]pyrazine-2-carbonitrile
3-hydroxy-9-oxo-9H-indeno[1,2-b]pyrazine-2-carbonitrile
3-amino-9-oxo-9H-indeno[1,2-b]pyrazine-2-carbonitrile
3-(4,4-difluoro-piperidin-1-yl)-9-oxo-9H-indeno[1,2-b]pyrazine-2-carbonitrile
3-chloro-9-oxo-9H-indeno[1,2-b]pyrazine-2-carbonitrile
9-(1',3'-dioxolan-2'-yl)-9H-indeno[1,2-b]pyrazine-2,3-dicarbonitrile
2-cyano-9-[hydroxyimino]-9H-indeno[1,2-b]pyrazine-3-carboxylic acid amide
9-(methoxyimino)-9H-indeno[1,2-b]pyrazine-2,3-dicarbonitrile
9-(Allyloxyimino)-9H-indeno[1,2-b]pyrazine-2,3-dicarbonitrile
9-Benzyloxyimino-9H-indeno[1,2-b]pyrazine-2,3-dicarbonitrile
9-Ethoxyimino-9H-indeno[1,2-b]pyrazine-2,3-dicarbonitrile
9-Phenoxyimino-9H-indeno[1,2-b]pyrazine-2,3-dicarbonitrile
6-Methoxy-9H-indeno[1,2-b]pyrazine-2,3-dicarbonitrile
6,7-Dimethoxy-9H-indeno[1,2-b]pyrazine-2,3-dicarbonitrile
8-Methyl-9H-indeno[1,2-b]pyrazine-2,3-dicarbonitrile
7,8-Dimethoxy-9H-indeno[1,2-b]pyrazine-2,3-dicarbonitrile
6-Methyl-9H-indeno[1,2-b]pyrazine-2,3-dicarbonitrile
5,8-Dimethoxy-9H-indeno[1,2-b]pyrazine-2,3-dicarbonitrile
6-Methoxy-9-oxo-9H-indeno[1,2-b]pyrazine-2,3-dicarbonitrile
6,7-Dimethoxy-9-oxo-9H-indeno[1,2-b]pyrazine-2,3-dicarbonitrile
8-Methyl-9-oxo-9H-indeno[1,2-b]pyrazine-2,3-dicarbonitrile 7,8-Dimethoxy-9-oxo-9H-indeno[1,2-b]pyrazine-2,3-dicarbonitrile
6-Methyl-9-oxo-9H-indeno[1,2-b]pyrazine-2,3-dicarbonitrile
5,8-Dimethoxy-9-oxo-9H-indeno[1,2-b]pyrazine-2,3-dicarbonitrile
7-Chloro-9-oxo-9H-indeno[1,2-b]pyrazine-2,3-dicarbonitrile
7-Fluoro-9-oxo-9H-indeno[1,2-b]pyrazine-2,3-dicarbonitrile
7-Hydroxy-9-oxo-9H-indeno[1,2-b]pyrazine-2,3-dicarbonitrile
benzo[4,5]thieno[2,3-b]pyrazine-2,3-dicarbonitrile
5,10-dioxo-5,10-dihydro-benzo[g]quinoxaline-2,3-dicarbonitrile
9-[hydroxyimino]-9H-indeno[1,2-b]pyrazine-2,3-dicarbonitrile
2-cyano-9-oxo-9H-indeno[1,2-b]pyrazin-3-yl-cyanamide
3-(1-cyano-2-ethoxy-2-hydroxy-vinyl)-9-oxo-9H-indeno[1,2-b]pyrazine-2-carbonitrile
3-ethylsulfanyl-9-oxo-9H-indeno[1,2-b]pyrazine-2-carbonitrile
7-Chloro-9-methoxyimino-9H-indeno[1,2-b]pyrazine-2,3-dicarbonitrile
9-Allyloxyimino-7-chloro-9H-indeno[1,2-b]pyrazine-2,3-dicarbonitrile
6-Chloro-9-oxo-9H-indeno[1,2-b]pyrazine-2,3-dicarbonitrile
2-(2-cyano-9-oxo-9H-indeno[1,2-b]pyrazin-3-yl)-acetamide
9-(2-Phenoxy-ethoxyimino)-9H-indeno[1,2-b]pyrazine-2,3-dicarbonitrile
7-Chloro-9-(2-phenoxy-ethoxyimino)-9H-indeno[1,2-b]pyrazine-2,3-dicarbonitrile
9-Allyloxyimino-6-chloro-9H-indeno[1,2-b]pyrazine-2,3-dicarbonitrile
7-Fluoro-8-methyl-9-oxo-9H-indeno[1,2-b]pyrazine-2,3-dicarbonitrile
6,7-dichloro-9-oxo-9H-indeno[1,2-b]pyrazine-2,3-dicarbonitrile
6-ethyl-9-oxo-9H-indeno[1,2-b]pyrazine-2,3-dicarbonitrile
2-cyano-9-[hydroxyimino]-9H-indeno[1,2-b]pyrazine-3-carboxylic acid amide
9-Allyloxyimino-2-cyano-9H-indeno[1,2-b]pyrazine-3-carboxylic acid amide2-Cyano-9-ethoxyimino-9H-indeno[1,2-b]pyrazine-3-carboxylic acid amide
2-Cyano-9-(2-methoxy-ethoxyimino)-9H-indeno[1,2-b]pyrazine-3-carboxylic acid amide
2-Cyano-9-methoxyimino-9H-indeno[1,2-b]pyrazine-3-carboxylic acid amide
2-cyano-9-acetoxyimino-9H-indeno[1,2-b]pyrazine-3-carboxylic acid amide
2-cyano-9-oxo-9H-indeno[1,2-b]pyrazine-3-carboxylic acid amide
(3-carbamoyl-2-cyano-indeno[1,2-b]pyrazin-9-ylideneaminooxy)-acetic acid ethyl ester
(3-carbamoyl-2-cyano-indeno[1,2-b]pyrazin-9-ylideneaminooxy)-acetic acid
[2-(3-carbamoyl-2-cyano-indeno[1,2-b]pyrazin-9-ylideneaminooxy)-acetylamino]-acetic acid ethyl ester
[2-(3-carbamoyl-2-cyano-indeno[1,2-b]pyrazin-9-ylideneaminooxy)-acetylamino]-acetic acid
7-chloro-3-hydroxy-9-oxo-9H-indeno[1,2-b]pyrazine-2-carbonitrile
9-[(aminocarbonyl)hydrazono]-7-chloro-9H-indeno[1,2-b]pyrazine-2,3-dicarbonitrile or their pharmaceutically acceptable salts, hydrates, or hydrated salts, or the polymorphic crystalline structures of these compounds or their optical isomers, racemates, diastereomers or enantiomers.

According to another aspect, preferred compounds of the invention are chosen from the group consisting in:
9-hydroxy-3-methoxy-9H-indeno[1,2-b]pyrazine-2-carbonitrile
3-methoxy-9-oxo-9H-indeno[1,2-b]pyrazine-2-carbonitrile
3-dimethylamino-9-oxo-9H-indeno[1,2-b]pyrazine-2-carbonitrile
3-(2-methoxy-ethoxy)-9-oxo-9H-indeno[1,2-b]pyrazine-2-carbonitrile
3-hydroxy-9-oxo-9H-indeno[1,2-b]pyrazine-2-carbonitrile
3-amino-9-oxo-9H-indeno[1,2-b]pyrazine-2-carbonitrile
3-(4,4-difluoro-piperidin-1-yl)-9-oxo-9H-indeno[1,2-b]pyrazine-2-carbonitrile
3-chloro-9-oxo-9H-indeno[1,2-b]pyrazine-2-carbonitrile
9-(1',3'-dioxolan-2'-yl)-9H-indeno[1,2-b]pyrazine-2,3-dicarbonitrile
2-cyano-9-[hydroxyimino]-9H-indeno[1,2-b]pyrazine-3-carboxylic acid amide
9-(methoxyimino)-9H-indeno[1,2-b]pyrazine-2,3-dicarbonitrile
9-(Allyloxyimino)-9H-indeno[1,2-b]pyrazine-2,3-dicarbonitrile
9-Benzyloxyimino-9H-indeno[1,2-b]pyrazine-2,3-dicarbonitrile
9-Ethoxyimino-9H-indeno[1,2-b]pyrazine-2,3-dicarbonitrile
9-Phenoxyimino-9H-indeno[1,2-b]pyrazine-2,3-dicarbonitrile
6-Methoxy-9H-indeno[1,2-b]pyrazine-2,3-dicarbonitrile
6,7-Dimethoxy-9H-indeno[1,2-b]pyrazine-2,3-dicarbonitrile
8-Methyl-9H-indeno[1,2-b]pyrazine-2,3-dicarbonitrile
7,8-Dimethoxy-9H-indeno[1,2-b]pyrazine-2,3-dicarbonitrile
6-Methyl-9H-indeno[1,2-b]pyrazine-2,3-dicarbonitrile
5,8-Dimethoxy-9H-indeno[1,2-b]pyrazine-2,3-dicarbonitrile
6-Methoxy-9-oxo-9H-indeno[1,2-b]pyrazine-2,3-dicarbonitrile
6,7-Dimethoxy-9-oxo-9H-indeno[1,2-b]pyrazine-2,3-dicarbonitrile
8-Methyl-9-oxo-9H-indeno[1,2-b]pyrazine-2,3-dicarbonitrile
7,8-Dimethoxy-9-oxo-9H-indeno[1,2-b]pyrazine-2,3-dicarbonitrile
6-Methyl-9-oxo-9H-indeno[1,2-b]pyrazine-2,3-dicarbonitrile
5,8-Dimethoxy-9-oxo-9H-indeno[1,2-b]pyrazine-2,3-dicarbonitrile
7-Chloro-9-oxo-9H-indeno[1,2-b]pyrazine-2,3-dicarbonitrile
7-Fluoro-9-oxo-9H-indeno[1,2-b]pyrazine-2,3-dicarbonitrile
7-Hydroxy-9-oxo-9H-indeno[1,2-b]pyrazine-2,3-dicarbonitrile
benzo[4,5]thieno[2,3-b]pyrazine-2,3-dicarbonitrile
5,10-dioxo-5,10-dihydro-benzo[g]quinoxaline-2,3-dicarbonitrile
2-cyano-9-oxo-9H-indeno[1,2-b]pyrazin-3-yl-cyanamide
3-(1-cyano-2-ethoxy-2-hydroxy-vinyl)-9-oxo-9H-indeno[1,2-b]pyrazine-2-carbonitrile
3-ethylsulfanyl-9-oxo-9H-indeno[1,2-b]pyrazine-2-carbonitrile 7-Chloro-9-methoxyimino-9H-indeno[1,2-b]pyrazine-2,3-dicarbonitrile
9-Allyloxyimino-7-chloro-9H-indeno[1,2-b]pyrazine-2,3-dicarbonitrile
6-Chloro-9-oxo-9H-indeno[1,2-b]pyrazine-2,3-dicarbonitrile
2-(2-cyano-9-oxo-9H-indeno[1,2-b]pyrazin-3-yl)-acetamide
9-(2-Phenoxy-ethoxyimino)-9H-indeno[1,2-b]pyrazine-2,3-dicarbonitrile
7-Chloro-9-(2-phenoxy-ethoxyimino)-9H-indeno[1,2-b]pyrazine-2,3-dicarbonitrile
9-Allyloxyimino-6-chloro-9H-indeno[1,2-b]pyrazine-2,3-dicarbonitrile
7-Fluoro-8-methyl-9-oxo-9H-indeno[1,2-b]pyrazine-2,3-dicarbonitrile
6,7-dichloro-9-oxo-9H-indeno[1,2-b]pyrazine-2,3-dicarbonitrile
6-ethyl-9-oxo-9H-indeno[1,2-b]pyrazine-2,3-dicarbonitrile
2-cyano-9-[hydroxyimino]-9H-indeno[1,2-b]pyrazine-3-carboxylic acid amide
9-Allyloxyimino-2-cyano-9H-indeno[1,2-b]pyrazine-3-carboxylic acid amide2-Cyano-9-ethoxyimino-9H-indeno[1,2-b]pyrazine-3-carboxylic acid amide
2-Cyano-9-(2-methoxy-ethoxyimino)-9H-indeno[1,2-b]pyrazine-3-carboxylic acid amide
2-Cyano-9-methoxyimino-9H-indeno[1,2-b]pyrazine-3-carboxylic acid amide
2-cyano-9-acetoxyimino-9H-indeno[1,2-b]pyrazine-3-carboxylic acid amide
2-cyano-9-oxo-9H-indeno[1,2-b]pyrazine-3-carboxylic acid amide
(3-carbamoyl-2-cyano-indeno[1,2-b]pyrazin-9-ylideneaminooxy)-acetic acid ethyl ester
(3-carbamoyl-2-cyano-indeno[1,2-b]pyrazin-9-ylideneaminooxy)-acetic acid
[2-(3-carbamoyl-2-cyano-indeno[1,2-b]pyrazin-9-ylideneaminooxy)-acetylamino]-acetic acid ethyl ester
[2-(3-carbamoyl-2-cyano-indeno[1,2-b]pyrazin-9-ylideneaminooxy)-acetylamino]-acetic acid
7-chloro-3-hydroxy-9-oxo-9H-indeno[1,2-b]pyrazine-2-carbonitrile
9-[(aminocarbonyl)hydrazono]-7-chloro-9H-indeno[1,2-b]pyrazine-2,3-dicarbonitrile or their pharmaceutically acceptable salts, hydrates, or hydrated salts, or the polymorphic crystalline structures of these compounds or their optical isomers, racemates, diastereomers or enantiomers.

More preferred compounds of the invention are chosen from the group consisting in:
2-cyano-9-[hydroxyimino]-9H-indeno[1,2-b]pyrazine-3-carboxylic acid amide
9-(methoxyimino)-9H-indeno[1,2-b]pyrazine-2,3-dicarbonitrile
9-Benzyloxyimino-9H-indeno[1,2-b]pyrazine-2,3-dicarbonitrile (13c).
9-Ethoxyimino-9H-indeno[1,2-b]pyrazine-2,3-dicarbonitrile (13d).
9-Phenoxyimino-9H-indeno[1,2-b]pyrazine-2,3-dicarbonitrile (13e).
8-Methyl-9-oxo-9H-indeno[1,2-b]pyrazine-2,3-dicarbonitrile
6-Methyl-9-oxo-9H-indeno[1,2-b]pyrazine-2,3-dicarbonitrile
5,8-Dimethoxy-9-oxo-9H-indeno[1,2-b]pyrazine-2,3-dicarbonitrile
7-Chloro-9-oxo-9H-indeno[1,2-b]pyrazine-2,3-dicarbonitrile
7-Fluoro-9-oxo-9H-indeno[1,2-b]pyrazine-2,3-dicarbonitrile
2-cyano-9-oxo-9H-indeno[1,2-b]pyrazine-3-carboxylic acid amide or their pharmaceutically acceptable salts, hydrates, or hydrated salts, or the polymorphic crystalline structures of these compounds or their optical isomers, racemates, diastereomers or enantiomers.

According to a further object, the present invention concerns also the pharmaceutical compositions comprising a compound of formula (I)

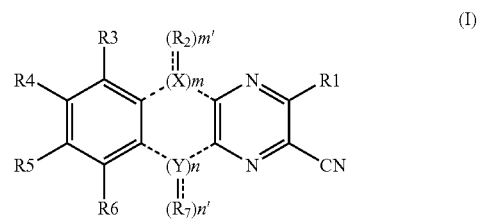

(I)

wherein:
m is 0; 1 or 2, wherein when m=0, —$(X(R2)_{m'})_m$- is none so as to form an open ring or a single bond;
n is 0, 1 or 2, wherein when n=0, —$(Y(R7)_{n'})_n$- is none so as to form an open ring or a single bond;
m' and n' are independently 0, 1 or 2;
X is a carbon atom or S or N;
Y is a carbon atom, or S or N;
Provided m and n are not simultaneously 0;
----- is either a single or double bond, as appropriate;
— is either none or a single bond, as appropriate;
R1 is chosen from the group consisting in H, CN, Hal, OAlk, OH, NRCN, C(CN)=C(OH)(OAlk), SR, NRR', $(Alk)_p$-C(O)NRR', Heterocycle, Aryle, Heteroaryle, where Alk, Aryle, Heteroaryle, Heterocycle are optionally substituted by Hal, NRR', CN, OH, $CF_3$, Aryle, Heteroaryle, OAlk
Where p is 0 or 1;
R3, R4, R5, R6 are each identical or different and are independently chosen from the group consisting in H, OAlk, Alk, Hal, NRR', CN, OH, $CF_3$, Aryle, Heteroaryle;
R2 is chosen from the group consisting in H, O, OH, N—OH, N-Aryle, N—OAlk, N—O-Aryle, N—O-Alk-Aryle, N—NR—CONRR', N—O—CO-Alk, or 2 R2 bound at the same X form together with that X an heterocycle; wherein said Alk, Aryle or heterocycle are optionally substituted by OAlk, Alk, Hal, NRR', CN, OH, $CF_3$, OAryl, —CO—$(NR-Alk-CO)_{p'}$—OAlk, —$CO(NR-Alk-CO)_{p'}$—OH,
Where p' is 0 or 1;
R7 is chosen from the group consisting in H, O, OH, N—OH, N-Aryle, N—OAlk, N—O-Aryle, N—O-Alk-Aryle, N—NR—CONRR', N—O—CO-Alk, or 2 R7 bound at the same Y form together with that Y an heterocycle; wherein said Alk, Aryle or heterocycle are optionally substituted by OAlk, Alk, Hal, NRR', CN, OH, $CF_3$, OAryl, —CO—$(NR-Alk-CO)_{p'}$—OAlk, —$CO(NR-Alk-CO)_{p'}$—OH,
Where p' is 0 or 1;
R and R' are each identical or different and are independently chosen from the group consisting in H, Alk, wherein Alk is optionally substituted by Hal, NRR', CN, OH, $CF_3$, Aryle, Heteroaryle;

or their pharmaceutically acceptable salts, hydrates, or hydrated salts, or the polymorphic crystalline structures of these compounds or their optical isomers, racemates, diastereomers or enantiomers.

According to a still further object, the present invention concerns the use of a compound of formula (I) as defined in respect of the pharmaceutical compositions of the invention, for the preparation of a medicament for inhibiting cysteine protease.

Preferred embodiments of formula (I) for the pharmaceutical compositions and use of the invention are defined as above.

Preferred compounds for the pharmaceutical compositions and use of the invention are chosen from the group consisting in:

9-oxo-9H-indeno[1,2-b]pyrazine-2,3-dicarbonitrile
9-hydroxy-3-methoxy-9H-indeno[1,2-b]pyrazine-2-carbonitrile
3-methoxy-9-oxo-9H-indeno[1,2-b]pyrazine-2-carbonitrile
3-dimethylamino-9-oxo-9H-indeno[1,2-b]pyrazine-2-carbonitrile
3-(2-methoxy-ethoxy)-9-oxo-9H-indeno[1,2-b]pyrazine-2-carbonitrile
3-hydroxy-9-oxo-9H-indeno[1,2-b]pyrazine-2-carbonitrile
3-amino-9-oxo-9H-indeno[1,2-b]pyrazine-2-carbonitrile
3-(4,4-difluoro-piperidin-1-yl)-9-oxo-9H-indeno[1,2-b]pyrazine-2-carbonitrile
3-chloro-9-oxo-9H-indeno[1,2-b]pyrazine-2-carbonitrile
9-(1',3'-dioxolan-2'-yl)-9H-indeno[1,2-b]pyrazine-2,3-dicarbonitrile
2-cyano-9-[hydroxyimino]-9H-indeno[1,2-b]pyrazine-3-carboxylic acid amide
9-[hydroxyimino]-9H-indeno[1,2-b]pyrazine-2,3-dicarbonitrile
9-(methoxyimino)-9H-indeno[1,2-b]pyrazine-2,3-dicarbonitrile
9-(Allyloxyimino)-9H-indeno[1,2-b]pyrazine-2,3-dicarbonitrile
9-Benzyloxyimino-9H-indeno[1,2-b]pyrazine-2,3-dicarbonitrile
9-Ethoxyimino-9H-indeno[1,2-b]pyrazine-2,3-dicarbonitrile
9-Phenoxyimino-9H-indeno[1,2-b]pyrazine-2,3-dicarbonitrile
9-[phenylimino]-9H-indeno[1,2-b]pyrazine-2,3-dicarbonitrile
6-Methoxy-9H-indeno[1,2-b]pyrazine-2,3-dicarbonitrile
6,7-Dimethoxy-9H-indeno[1,2-b]pyrazine-2,3-dicarbonitrile
8-Methyl-9H-indeno[1,2-b]pyrazine-2,3-dicarbonitrile
7,8-Dimethoxy-9H-indeno[1,2-b]pyrazine-2,3-dicarbonitrile
6-Methyl-9H-indeno[1,2-b]pyrazine-2,3-dicarbonitrile
5,8-Dimethoxy-9H-indeno[1,2-b]pyrazine-2,3-dicarbonitrile
6-Methoxy-9-oxo-9H-indeno[1,2-b]pyrazine-2,3-dicarbonitrile
6,7-Dimethoxy-9-oxo-9H-indeno[1,2-b]pyrazine-2,3-dicarbonitrile
8-Methyl-9-oxo-9H-indeno[1,2-b]pyrazine-2,3-dicarbonitrile
7,8-Dimethoxy-9-oxo-9H-indeno[1,2-b]pyrazine-2,3-dicarbonitrile
6-Methyl-9-oxo-9H-indeno[1,2-b]pyrazine-2,3-dicarbonitrile
5,8-Dimethoxy-9-oxo-9H-indeno[1,2-b]pyrazine-2,3-dicarbonitrile
7-Chloro-9-oxo-9H-indeno[1,2-b]pyrazine-2,3-dicarbonitrile
7-Fluoro-9-oxo-9H-indeno[1,2-b]pyrazine-2,3-dicarbonitrile
7-Methoxy-9-oxo-9H-indeno[1,2-b]pyrazine-2,3-dicarbonitrile
7-Hydroxy-9-oxo-9H-indeno[1,2-b]pyrazine-2,3-dicarbonitrile
benzo[4,5]thieno[2,3-b]pyrazine-2,3-dicarbonitrile
5,10-dioxo-5,10-dihydro-benzo[g]quinoxaline-2,3-dicarbonitrile
2-cyano-9-oxo-9H-indeno[1,2-b]pyrazin-3-yl-cyanamide
3-(1-cyano-2-ethoxy-2-hydroxy-vinyl)-9-oxo-9H-indeno[1,2-b]pyrazine-2-carbonitrile
3-ethylsulfanyl-9-oxo-9H-indeno[1,2-b]pyrazine-2-carbonitrile
7-Chloro-9-methoxyimino-9H-indeno[1,2-b]pyrazine-2,3-dicarbonitrile
9-Allyloxyimino-7-chloro-9H-indeno[1,2-b]pyrazine-2,3-dicarbonitrile
6-Chloro-9-oxo-9H-indeno[1,2-b]pyrazine-2,3-dicarbonitrile
2-(2-cyano-9-oxo-9H-indeno[1,2-b]pyrazin-3-yl)-acetamide
9-(2-Phenoxy-ethoxyimino)-9H-indeno[1,2-b]pyrazine-2,3-dicarbonitrile
7-Chloro-9-(2-phenoxy-ethoxyimino)-9H-indeno[1,2-b]pyrazine-2,3-dicarbonitrile
9-Allyloxyimino-6-chloro-9H-indeno[1,2-b]pyrazine-2,3-dicarbonitrile
7-Fluoro-8-methyl-9-oxo-9H-indeno[1,2-b]pyrazine-2,3-dicarbonitrile
6,7-dichloro-9-oxo-9H-indeno[1,2-b]pyrazine-2,3-dicarbonitrile
6-ethyl-9-oxo-9H-indeno[1,2-b]pyrazine-2,3-dicarbonitrile
2-cyano-9-[hydroxyimino]-9H-indeno[1,2-b]pyrazine-3-carboxylic acid amide
9-Allyloxyimino-2-cyano-9H-indeno[1,2-b]pyrazine-3-carboxylic acid amide2-Cyano-9-ethoxyimino-9H-indeno[1,2-b]pyrazine-3-carboxylic acid amide
2-Cyano-9-(2-methoxy-ethoxyimino)-9H-indeno[1,2-b]pyrazine-3-carboxylic acid amide
2-Cyano-9-methoxyimino-9H-indeno[1,2-b]pyrazine-3-carboxylic acid amide
2-cyano-9-acetoxyimino-9H-indeno[1,2-b]pyrazine-3-carboxylic acid amide
2-cyano-9-oxo-9H-indeno[1,2-b]pyrazine-3-carboxylic acid amide
(3-carbamoyl-2-cyano-indeno[1,2-b]pyrazin-9-ylideneaminooxy)-acetic acid ethyl ester
(3-carbamoyl-2-cyano-indeno[1,2-b]pyrazin-9-ylideneaminooxy)-acetic acid
[2-(3-carbamoyl-2-cyano-indeno[1,2-b]pyrazin-9-ylideneaminooxy)-acetylamino]-acetic acid ethyl ester
[2-(3-carbamoyl-2-cyano-indeno[1,2-b]pyrazin-9-ylideneaminooxy)-acetylamino]-acetic acid
7-chloro-3-hydroxy-9-oxo-9H-indeno[1,2-b]pyrazine-2-carbonitrile
9-[(aminocarbonyl)hydrazono]-7-chloro-9H-indeno[1,2-b]pyrazine-2,3-dicarbonitrile or their pharmaceutically acceptable salts, hydrates, or hydrated salts, or the polymorphic crystalline structures of these compounds or their optical isomers, racemates, diastereomers or enantiomers.

More preferred compounds for the pharmaceutical compositions and use of the invention are chosen from the group consisting in:

9-oxo-9H-indeno[1,2-b]pyrazine-2,3-dicarbonitrile
2-cyano-9-[hydroxyimino]-9H-indeno[1,2-b]pyrazine-3-carboxylic acid amide
9-(methoxyimino)-9H-indeno[1,2-b]pyrazine-2,3-dicarbonitrile
9-Benzyloxyimino-9H-indeno[1,2-b]pyrazine-2,3-dicarbonitrile (13c).
9-Ethoxyimino-9H-indeno[1,2-b]pyrazine-2,3-dicarbonitrile (13d).
9-Phenoxyimino-9H-indeno[1,2-b]pyrazine-2,3-dicarbonitrile (13e).
9-[phenylimino]-9H-indeno[1,2-b]pyrazine-2,3-dicarbonitrile
8-Methyl-9-oxo-9H-indeno[1,2-b]pyrazine-2,3-dicarbonitrile
6-Methyl-9-oxo-9H-indeno[1,2-b]pyrazine-2,3-dicarbonitrile
5,8-Dimethoxy-9-oxo-9H-indeno[1,2-b]pyrazine-2,3-dicarbonitrile
7-Chloro-9-oxo-9H-indeno[1,2-b]pyrazine-2,3-dicarbonitrile
7-Fluoro-9-oxo-9H-indeno[1,2-b]pyrazine-2,3-dicarbonitrile
2-cyano-9-oxo-9H-indeno[1,2-b]pyrazine-3-carboxylic acid amide or their pharmaceutically acceptable salts, hydrates, or hydrated salts, or the polymorphic crystalline structures of these compounds or their optical isomers, racemates, diastereomers or enantiomers.

As used hereabove or hereafter:

Alk represents alkyl, alken or alkyn.

"Alkyl" means an aliphatic hydrocarbon group which may be straight or branched having 1 to 20 carbon atoms in the chain. Preferred alkyl groups have 1 to 12 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Alken" means an aliphatic hydrocarbon group containing a carbon-carbon double bond and which may be straight or branched having 2 to 15 carbon atoms in the chain. Preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkyn" means an aliphatic hydrocarbon group containing a carbon-carbon triple bond and which may be straight or branched having 2 to 15 carbon atoms in the chain. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

"Halogen atom" refers to fluorine, chlorine, bromine or iodine atom; preferably fluorine and chlorine atom.

"Aryl" means an aromatic monocyclic or multicyclic hydrocarbon ring system of 6 to 14 carbon atoms, preferably of 6 to 10 carbon atoms. Exemplary aryl groups include phenyl or naphthyl.

As used herein, the terms "heterocycle" or "heterocyclic" refer to a saturated, partially unsaturated or unsaturated, non aromatic stable 3 to 14, preferably 5 to 10 membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in *The Handbook of Chemistry and Physics*, 76th Edition, CRC Press, Inc., 1995-1996, p. 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydro-pyridyl, dihydropyridyl, tetrahydropyrimidinyl, dihydrothiopyranyl, azepanyl, as well as the fused systems resulting from the condensation with a phenyl group.

As used herein, the term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocycle" and the likes refers also to the corresponding "alkylene", "cycloalkylene", "alkenylene", "alkynylene", "arylene", "heteroarylene", "heterocyclene" and the likes which are formed by the removal of two hydrogen atoms.

As used herein, the term "patient" refers to either an animal, such as a valuable animal for breeding, company or preservation purposes, or preferably a human or a human child, which is afflicted with, or has the potential to be afflicted with one or more diseases and conditions described herein.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

The compounds of the general formula (I) having geometrical and stereoisomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3$^{rd}$ ed., John Wiley and Sons, 1999; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

The process of preparation of a compound of formula (I) of the invention is a further object of the present invention.

According to a first aspect, compounds of the invention of formula (I) can be obtained from corresponding compounds of formula (II)

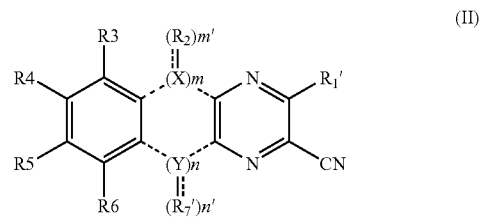

wherein R3, R4, R5, R6, X, Y, m, m', n, n' are defined as in formula (I) and R7' is R7 as defined in formula (I) or a precursor thereof and R1' is R1 as defined in formula (I) or a precursor thereof.

According to the present invention, the expression "precursor group" of a functional group refers to any group which can, by one or more reactions, lead to the desired function, by means of one or more suitable reagents. Those reactions include de-protection, as well as usual addition, substitution or functionalization reactions.

Preferably, in formula (II), R1' represents a CN group.

Generally, the compound of formula (I) is obtained from compound of formula (II) by one or more step allowing a precursor function to be transformed into the desired —R1 group. Simultaneously, the R7' group can be transformed to the desired R7, if appropriate.

The compounds of formula (II) can be obtained from corresponding compounds of formula (III):

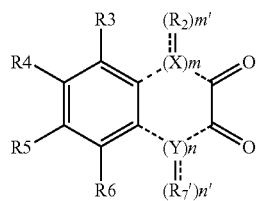

(III)

wherein R3, R4, R5, R6, X, Y, m, m', n, n' are defined as in formula (I) and R7' is defined as in formula (II). Generally, when R1'=CN, this reaction is usually carried out in the presence of diaminomaleodinitrile.

According to an alternative embodiment, the compounds of formula (II) can be obtained from corresponding compounds of formula (III'):

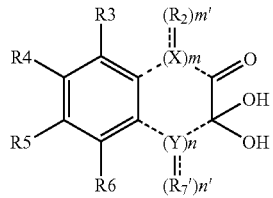

(III')

wherein R3, R4, R5, R6, X, Y, m, m', n, n' are defined as in formula (I) and R7' is defined as in formula (III').

Generally, when R1'=CN, this reaction is usually carried out in the presence of diaminomaleodinitrile.

According to an alternative embodiment, the compound of formula (II) can be obtained from corresponding compounds of formula (IV):

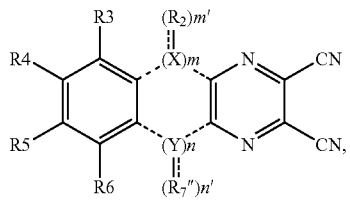

(IV)

wherein R3, R4, R5, R6, X, Y, m, m', n, n' are defined as in formula (I) and R7" represents R7' or a precursor thereof, if appropriate.

The compound of formula (III) can be obtained from a corresponding compound of formula (V):

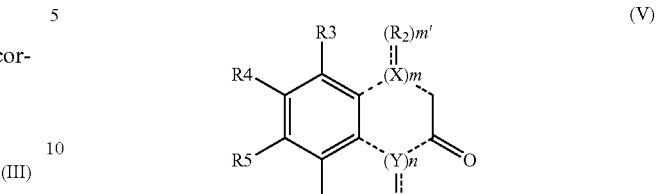

(V)

wherein R3, R4, R5, R6, X, Y, m, m', n, n' are defined as in formula (I) and R7' is defined as in formula (II).

The compound of formula (IV) can be obtained from a corresponding compound of formula (III). Generally, this reaction is carried in the presence of diaminomaleodinitrile.

The above reactions can be carried out by the skilled person by applying or adapting the methods illustrated in the examples hereinafter.

Further, the process of the invention may also comprise the additional step of isolating the compound of formula (I). This can be done by the skilled person by any of the known conventional means, such as the recovery methods described above.

The starting products are commercially available or may be obtained by applying or adapting any known methods or those described in the examples.

The synthesis may also be carried out in one pot as a multicomponent reaction.

According to a further object, the present invention is also concerned with pharmaceutical compositions comprising a compound of formula (I) together with pharmaceutically acceptable excipients.

The compounds of the invention are useful for inhibiting cysteine proteases, in particular de-ubiquitination enzymes (such as USPs and UCHs), caspases, cathepsins (in particular cathepsin B, D, K, S and the likes), calpains as well as viral, bacterial or parasitic cysteine proteases in patients in the need thereof.

The compounds of the invention are particularly useful for treating and/or preventing cancer and metastasis, neurodegenerative diseases such as Alzheimer's disease and Parkinson's disease, deafness, disorders associated with ageing, inflammatory disorders, arthritis, osteoporosis, hepatitis, liver failure, cardiac ischemia and failure, stroke, atherosclerosis, renal failure, diabetes, cataract; viral acute or latent infections by Herpes simplex virus-1, Epstein-Barr virus, SARS coronavirus, rhinoviruses, poliomyelitis virus, hepatitis A virus, hepatitis C virus, adenoviruses, and the like; bacterial or fungal infections by pathogenic agents belonging to the *Streptococcus* sp., *Staphylococcus* sp., *Clostidium* sp., *Aspergillus* sp., genera and the like; protozoal infections by species members of the *Trypanosoma* sp., *Plasmodium* sp., *Leishmania* sp., *Trichomonas* sp., *Entamoeba* sp., *Giardia* sp., *Toxoplasma* sp., *Cryptosporidium* sp., genera and the like; flat or round worm infections by species members of the *Fasciola* sp., *Schistosoma* sp., *Onchocerca* sp., *Ascaris* sp., *Taenia* sp., *Caenorhabitis* sp., *Toxocara* sp., *Haemonchus* sp., *Ancylostoma* sp., *Trichuris* sp., *Trichinella* sp., *Strongyloides* sp., *Brugia* sp., genera and the like; as well as immunological, immunoregulatory or antigen presentation disorders.

The present invention also concerns the corresponding methods of treatment comprising the administration of a compound of the invention together with a pharmaceutically acceptable carrier or excipient to a patient in the need thereof.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in preventing or treating a pathological condition requiring the inhibition of an active cysteine protease involved in its pathogenesis.

According to the invention, the term "patient", or "patient in need thereof", is intended for an animal or a human being affected or likely to be affected with a pathological condition involving an active cysteine protease in its pathogenesis. Preferably, the patient is human.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The compounds of the present invention are also capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably the unit dose range is from 1 to 500 mg administered one to six times a day, and even more preferably from 10 mg to 500 mg, once a day. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well known in the pharmaceutical art, for example, as described in *Remington: The Science and Practice of Pharmacy*, $20^{th}$ ed.; Gennaro, A. R., Ed.; Lippincott Williams & Wilkins: Philadelphia, Pa., 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description in the following examples.

Representative compounds of the invention are summarized in the table below:

| Formula | Experimental N° |
|---|---|
| 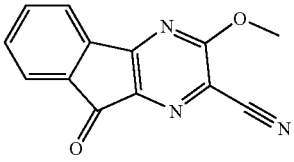 [SMILES: COc1nc2c(nc1C#N)C(=O)c1ccccc1-2] | Example 1 |
| 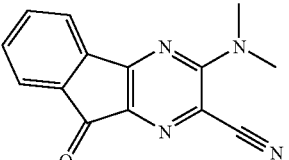 | Example 2 |

-continued

| Formula | Experimental N° |
|---|---|
| 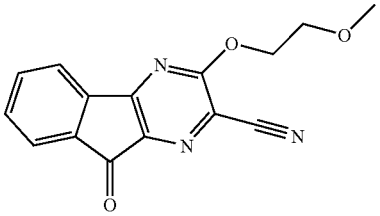 [SMILES: COCCOc1nc2c(nc1C#N)C(=O)c1ccccc1-2] | Example 3 |
| 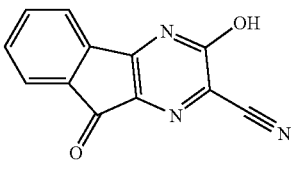 [SMILES: N#Cc1nc2c(nc1O)-c1ccccc1C2=O] | Example 4 |
| 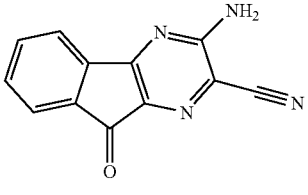 [SMILES: N#Cc1nc2c(nc1N)-c1ccccc1C2=O] | Example 5 |
| 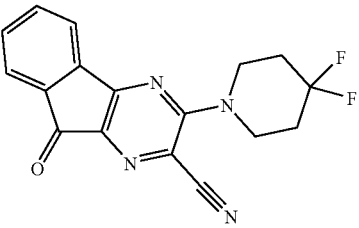 [SMILES: N#Cc1nc2c(nc1N1CCC(F)(F)CC1)-c1ccccc1C2=O] | Example 6 |
| 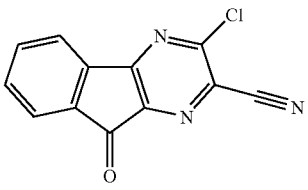 [SMILES: N#Cc1nc2c(nc1Cl)-c1ccccc1C2=O] | Example 7 |
| 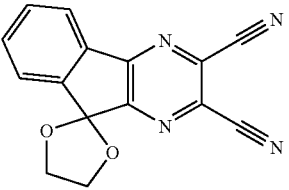 [SMILES: N#Cc1nc2c(nc1C#N)C1(OCCO1)c1ccccc1-2] | Example 8 |
|  | Example 9 |
|  | Example 10 |

| Formula | Experimental N° |
|---|---|
| 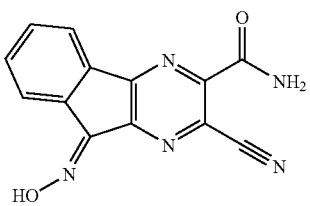 [SMILES: N#Cc1nc2c(nc1C(N)=O)-c1ccccc1/C2=N\O] | Example 11 |
| 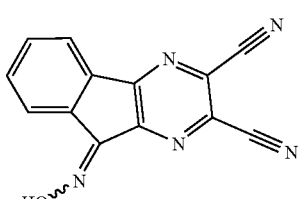 | Example 12 |
| 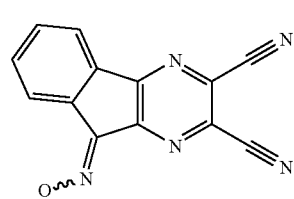 | Example 13 |
| 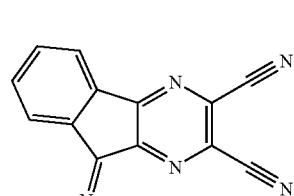 | Example 13b |
| 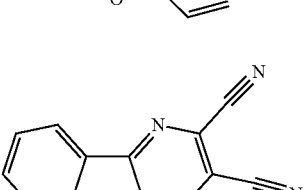 | Example 13C |
| 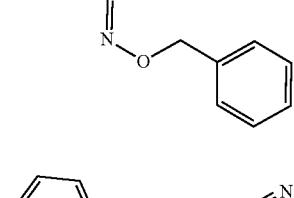 | Example 13d |
| 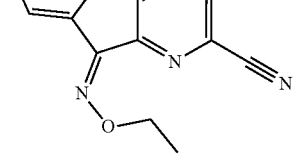 | Example 13e |
| 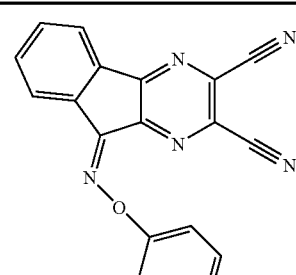 | Example 14 |
| 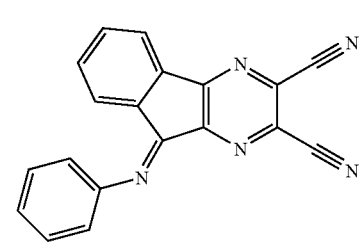 [SMILES: N#Cc1nc2c(nc1C#N)-c1ccccc1/C2=N\c1ccccc1] | Example 16b |
| 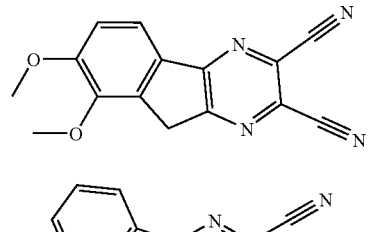 | Example 16c |
| 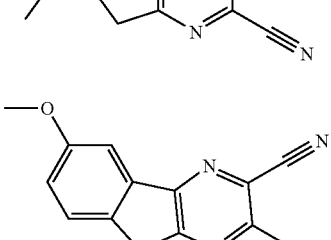 | Example 17a |
| 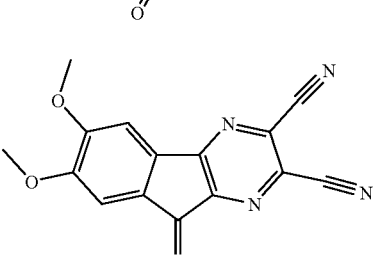 | Example 17b |
| 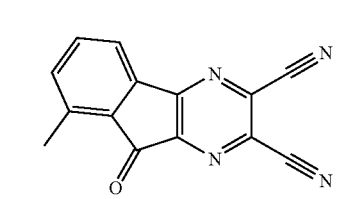 [SMILES: Cc1cccc2c1C(=O)c1nc(C#N)c(C#N)nc1-2] | Example 17c |

| Formula | Experimental N° |
|---|---|
| 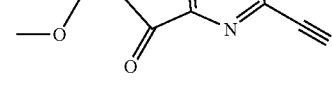 | Example 17d |
| 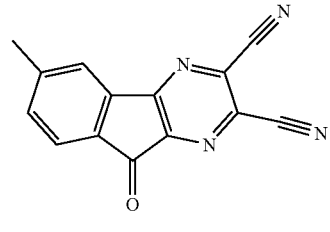 [SMILES: Cc1ccc2c(c1)-c1nc(C#N)c(C#N)nc1C2=O] | Example 17e |
| 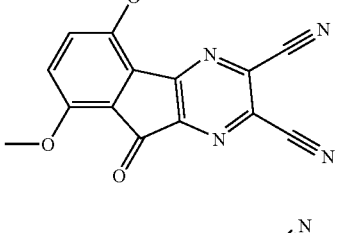 | Example 17f |
| 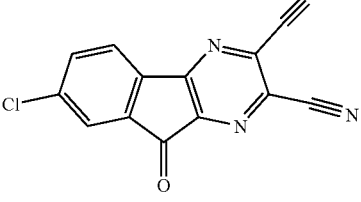 | Example 17g |
| 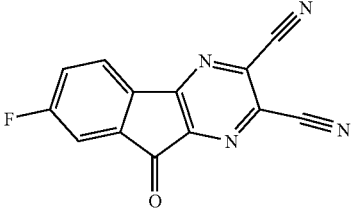 [SMILES: N#Cc1nc2c(nc1C#N)-c1ccc(F)cc1C2=O] | Example 17h |
| 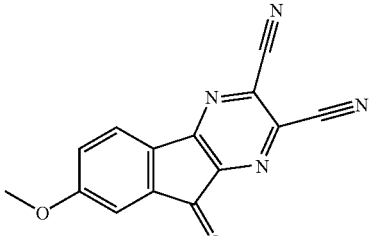 | Example 17i |
| 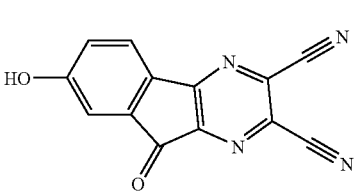 [SMILES: N#Cc1nc2c(nc1C#N)-c1ccc(O)cc1C2=O] | Example 17j |
| Formula | Experimental N° |
|---|---|
| | Example 19 |
| | Example 20 |
| | Example 21 |
| | Example 22 |
| | Example 23 |
| | Example 24a |

| Formula | Experimental N° |
|---|---|
| | Example 24b |
| | Example 25 |
| | Example 26 |
| | Example 27a |
| | Example 27b |
| | Example 27c |

| Formula | Experimental N° |
|---|---|
| | Example 30 |
| | Example 31 |
| | Example 32 |
| | Example 33 |
| | Example 34a |
| | Example 34b |
| | Example 34c |

| Formula | Experimental N° |
|---|---|
| | Example 34d |
| | Example 35 |
| | Example 36 |
| | Example 37 |

| Formula | Experimental N° |
|---|---|
| | Example 38 |
| | Example 40 |
| | Example 41 |
| | Example 42 |

| Formula | Experimental N° |
|---|---|
| 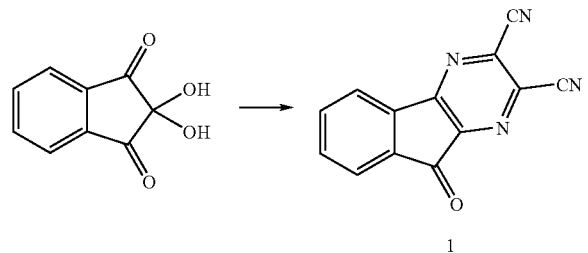 [SMILES: O=C1c2ccccc2C(=O)C1(O)O ; N#Cc1nc2c(nc1C#N)-c1ccccc1C2=O] | Example 43 |

EXPERIMENTAL

Representative compounds of the invention can be synthesized according to the following procedures:

Synthesis of 9-oxo-9H-indeno[1,2-b]pyrazine-2,3-dicarbonitrile (1)

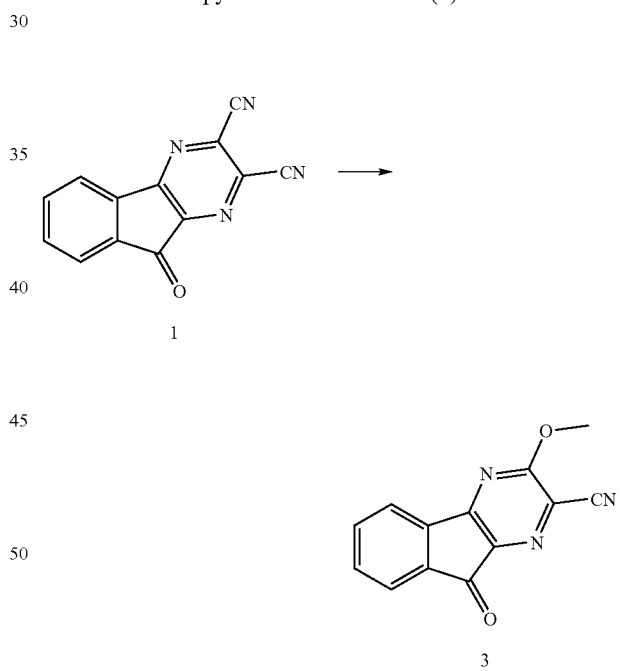

To a solution of ninhydrin (18.58 g, 104.3 mmol) in H$_2$O/EtOH/AcOH (130:195:9.1; 167 ml) a solution of diaminomaleodinitrile (11.27 g, 104.3 mmol) in H$_2$O/EtOH/AcOH (130:195:9.1; 167 ml) was added and the mixture was stirred at 60° C. After 3 hours, the precipitate was collected by filtration, washed with EtOH (100 ml) and dried under vacuum, affording 1 (23.64 g, 98%) as yellow-brown solid.

$^1$H NMR (300 MHz, CDCl$_3$): δ 8.07 (d, 1H), 7.98 (d, 1H), 7.87 (dd, 1H), 7.76 (dd, 1H). ESI$^+$MS: calcd for C$_{13}$H$_4$N$_4$O: 232.20; found: 233.0 (MH$^+$).

Synthesis of 9-hydroxy-3-methoxy-9H-indeno[1,2-b]pyrazine-2-carbonitrile (2)

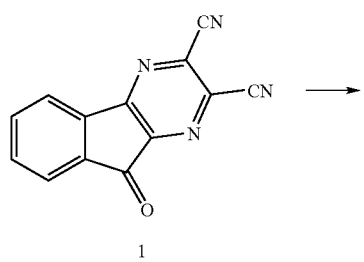

To a suspension of 1 (150 mg, 0.646 mmol) in MeOH (6.5 ml), cooled at 0° C., NaBH$_4$ (24 mg, 0.646 mmol) was added. After 30 min, water (5 ml) was added, MeOH was evaporated and the residue was extracted with CH$_2$Cl$_2$ (3×5 ml). The organic layers were dried over Na$_2$SO$_4$, filtered and evaporated. EtOH was added and the precipitate was collected by filtration affording 2 (82 mg, 53%) as white solid.

$^1$H NMR (300 MHz, DMSO d$_6$): δ 7.93 (d, 1H), 7.76 (d, 1H), 7.65 (dd, 1H), 7.58 (dd, 1H), 6.27 (d, 1H), 5.50 (d, 1H), 4.17 (s, 3H). ESI$^+$MS: calcd for C$_{13}$H$_9$N$_3$O$_2$: 239.24; found: 240.1 (MH$^+$).

Synthesis of 3-methoxy-9-oxo-9H-indeno[1,2-b]pyrazine-2-carbonitrile (3)

To a suspension of 1 (1.10 g, 4.7 mmol) in MeOH (47 ml) sodium (110 mg) was added and the mixture was stirred at room temperature for 16 hours. The precipitate was filtered, washed with EtOH and dried under vacuum, yielding 3 (1.03 g, 93%) as yellow-green solid.

$^1$H NMR (300 MHz, DMSO d$_6$): δ 7.92 (d, 1H), 7.83 (m, 2H), 7.71 (dd, 1H), 4.25 (s, 3H). ESI$^+$MS: calcd for C$_{13}$H$_7$N$_3$O$_2$: 237.22; found: 238.0 (MH$^+$).

Synthesis of 3-dimethylamino-9-oxo-9H-indeno[1,2-b]pyrazine-2-carbonitrile (4)

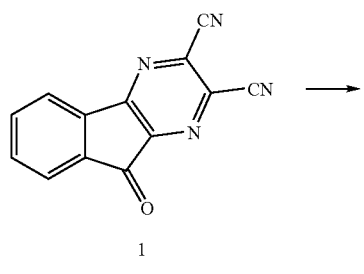

To a solution of 1 (53 mg, 0.228 mmol) in THF (2 ml) dimethylamine (2M in THF, 1.1 ml, 2.28 mmol) was added. The mixture was stirred at room temperature for 16 hours, then the solvent was evaporated affording 4 (56 mg, 98%) as yellow solid.

$^1$H NMR (300 MHz, DMSO $d_6$): δ 7.85 (d, 1H), 7.80-7.73 (m, 2H), 7.67 (dd, 1H), 3.47 (s, 6H). ESI$^+$MS: calcd for $C_{14}H_{10}N_4O$: 250.26; found: 251.1 (MH$^+$).

Synthesis of 3-(2-methoxy-ethoxy)-9-oxo-9H-indeno[1,2-b]pyrazine-2-carbonitrile (5)

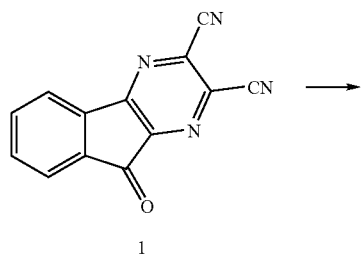

A suspension of 1 (59 mg, 0.254 mmol) in methoxyethanol (2.5 ml) was heated by MW (150° C., 30 min) in a sealed tube. The resulting suspension was filtered and the solid collected, washed with EtOH and dried under vacuum, yielding 5 (50 mg, 70%) as green solid.

$^1$H NMR (300 MHz, DMSO $d_6$): δ 7.90 (d, 1H), 7.83 (dd, 1H), 7.82 (d, 1H), 7.71 (dd, 1H), 4.79 (m, 2H), 3.80 (m, 2H), 3.36 (s, 3H). ESI$^+$MS: calcd for $C_{15}H_{11}N_3O_3$: 281.27; found: 282.0 (MH$^+$).

Synthesis of 3-hydroxy-9-oxo-9H-indeno[1,2-b]pyrazine-2-carbonitrile (6)

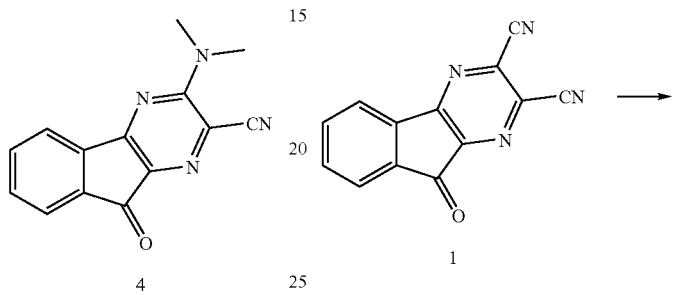

A suspension of 1 (5.66 g, 24.3 mmol) in aqueous NaOH (2% w/v, 81 ml) was stirred at room temperature for 16 hours. The mixture was acidified with 3N HCl to pH 1, the precipitate was collected by filtration, washed with water and dried under vacuum, affording 6 (4.88 g, 90%) as light brown solid.

$^1$H NMR (300 MHz, DMSO $d_6$): δ 7.89 (d, 1H), 7.79-7.62 (m, 3H). ESI$^+$MS: calcd for $C_{12}H_5N_3O_2$: 223.19; found: 224.0 (MH$^+$).

Synthesis of 3-amino-9-oxo-9H-indeno[1,2-b]pyrazine-2-carbonitrile (7)

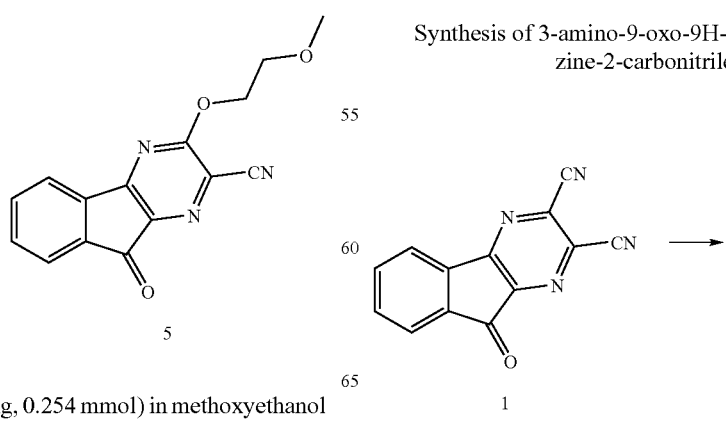

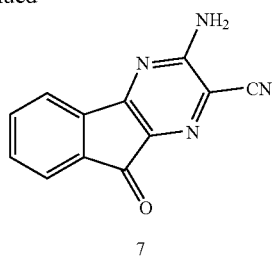

7

A mixture of 1 (201 mg, 0.86 mmol), ammonium acetate (331 mg, 4.3 mmol) and Na$_2$SO$_4$ (200 mg) in THF (2.9 ml) was stirred at 70° C. in sealed tube for 18 hours. The solvent was evaporated, water (5 ml) was added and the precipitate filtered, washed with water and dried under vacuum, affording 7 (171 mg, 90%) as green solid.

$^1$H NMR (300 MHz, DMSO d$_6$): δ 8.45 (bs, 2H), 7.78-7.63 (m, 4H). ESI$^+$MS: calcd for C$_{12}$H$_6$N$_4$O: 222.21; found: 223.1 (MH$^+$).

Synthesis of 3-(4,4-difluoro-piperidin-1-yl)-9-oxo-9H-indeno[1,2-b]-pyrazine-2-carbonitrile (8)

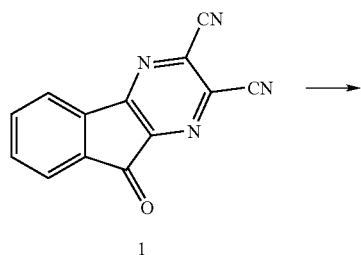

1

4,4-Difluoropiperidine hydrochloride (249 mg, 1.58 mmol) was dissolved in 1N NaOH (5 ml) and extracted with CH$_2$Cl$_2$ (2×5 ml). Organic phase was dried over Na$_2$SO$_4$, filtered and evaporated. The residue was dissolved in THF (2 ml) and this solution was added to a solution of 1 (185 mg, 0.79 mmol) in THF (2 ml); the mixture was stirred at room temperature for 48 hours. The solvent was evaporated, the crude solid washed with EtOH and dried under vacuum, affording 8 (245 mg, 95%) as yellow-brown solid.

$^1$H NMR (300 MHz, DMSO d$_6$): δ 7.89 (d, 1H), 7.79 (dd, 1H), 7.78 (d, 1H), 7.69 (dd, 1H), 4.13 (m, 4H), 2.22 (m, 4H). ESI$^+$MS: calcd for C$_{17}$H$_{12}$F$_2$N$_4$O: 326.31; found: 327.1 (MH$^+$).

Synthesis of 3-chloro-9-oxo-9H-indeno[1,2-b]pyrazine-2-carbonitrile (9)

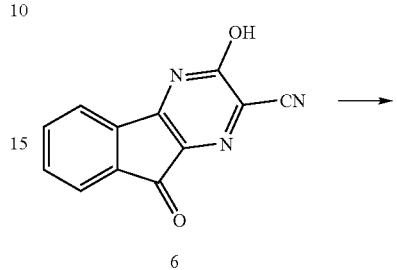

6

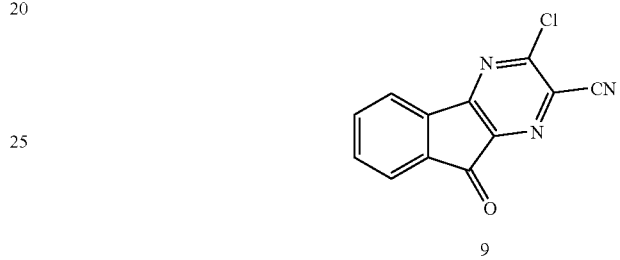

9

A suspension of 6 (671 mg, 3.0 mmol) in POCl$_3$ (8.4 ml) was heated under stirring to 100° C. for 17 h. Excess of POCl$_3$ was evaporated under reduced pressure and the crude was purified by flash chromatography on silica (CH$_2$Cl$_2$), affording 9 (320 mg, 44%) as yellow solid.

$^1$H NMR (300 MHz, DMSO d$_6$): δ 8.02 (d, 1H), 7.90 (m, 2H), 7.78 (dd, 1H). ESI$^+$MS: calcd for C$_{12}$H$_4$ClN$_3$O: 241.64; found: 241.9 (MH$^+$).

Synthesis of 9-(1',3'-dioxolan-2'-yl)-9H-indeno[1,2-b]pyrazine-2,3-dicarbonitrile (10)

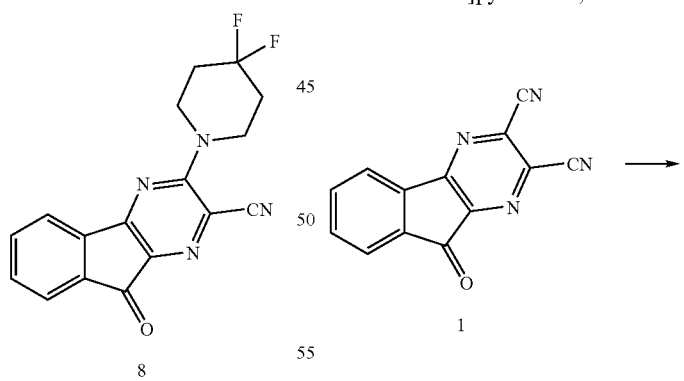

1

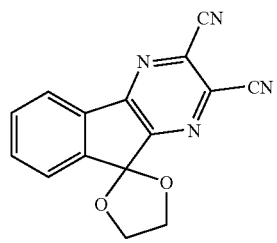

10

To a suspension of 1 (5.09 g, 21.9 mmol) in toluene (146 ml) ethylene glycol (2.4 ml, 43.8 mmol) and PTSA (6.25 g, 32.8 mmol) were added. The mixture was refluxed in a Dean-Stark apparatus for 28 hours, then, the solvent was evaporated. The crude was purified by flash chromatography on silica (CH$_2$Cl$_2$), affording 10 (3.87 g, 64%) as light yellow solid.

$^1$H NMR (300 MHz, DMSO d$_6$): δ 8.03 (m, 1H), 7.83-7.70 (m, 3H), 4.47 (s, 4H). ESI$^+$MS: calcd for C$_{15}$H$_8$N$_4$O$_2$: 276.26; found: 277.3 (MH$^+$).

Synthesis of 2-cyano-9-[hydroxyimino]-9H-indeno[1,2-b]pyrazine-3-carboxylic acid amide (11)

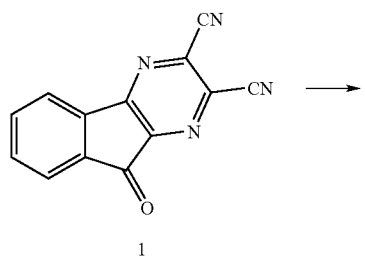

1

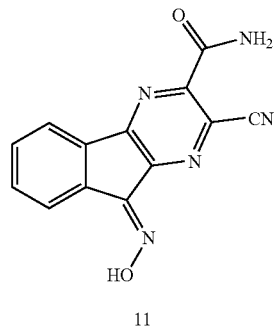

11

To a solution of 1 (500 mg, 2.1 mmol) in CH$_3$CN (20 ml) hydroxylamine (50% wt. in water, 0.25 ml, 4.2 mmol) was added at 0° C. The mixture was stirred at this temperature for 2.5 hours, then the formed precipitate was collected by filtration and dried under vacuum, affording 11 (355 mg, 62%) as red-brown solid.

$^1$H NMR (300 MHz, DMSO d$_6$): δ 10.96 (s, 1H), 8.11 (d, 1H), 7.89 (dd, 1H), 7.88 (d, 1H), 7.74 (dd, 1H), 6.32 (bs, 2H). ESI$^+$MS: calcd for C$_{13}$H$_7$N$_5$O$_2$: 265.23; found: 265.9 (MH$^+$).

Synthesis of 9-[hydroxyimino]-9H-indeno[1,2-b]pyrazine-2,3-dicarbonitrile (12)

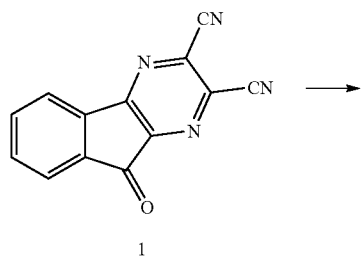

1

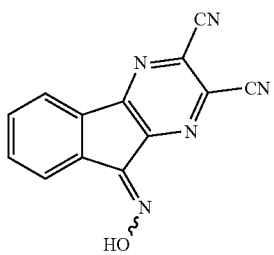

12

To a suspension of 1 (150 mg, 0.646 mmol) in pyridine (10 ml) hydroxylamine hydrochloride (134 mg, 1.94 mmol) was added at 0° C. Molecular sieves were added and the mixture was stirred at room temperature for 16 hours. The insoluble residue was filtered, the solvent evaporated and the crude purified by flash chromatography on silica (petroleum spirit/EtOAc 9:1), affording 12 (55 mg, 35%) as yellow solid in diastereoisomeric ratio 9:1.

$^1$H NMR for the main product (300 MHz, DMSO d$_6$): main product: δ 14.28 (bs, 1H), 8.54 (d, 1H), 8.22 (d, 1H), 7.84 (dd, 1H), 7.78 (dd, 1H). ESI$^+$MS: calcd for C$_{13}$H$_5$N$_5$O: 247.22; found: 247.9 (MH$^+$).

General Procedure A: Synthesis of Alkyloxyimines

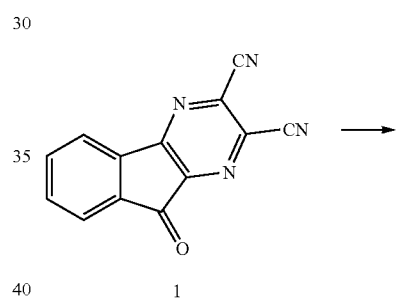

1

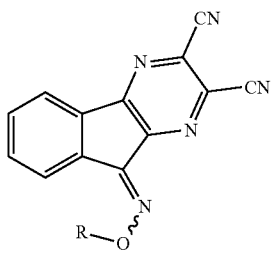

13a-d a R = Me
b R = CH$_2$—CH═CH$_2$
c R = CH$_2$—Ph
d R = Et

To a suspension of 1 (620 mg, 2.67 mmol) in pyridine (15 ml) a solution of O-alkyl-hydroxylamine hydrochloride (8.31 mmol) in pyridine (15 ml) was added dropwise at 0° C. Molecular sieves were added and the mixture was stirred at room temperature for 16 hours. The insoluble residue was filtered, the solvent evaporated and the crude purified by flash chromatography on silica (petroleum spirit/EtOAc 9:1).

Synthesis of 9-(methoxyimino)-9H-indeno[1,2-b]pyrazine-2,3-dicarbonitrile (13a)

Prepared according to the general procedure A in 35% yield as yellow solid in diastereoisomeric ratio 3:1. $^1$H NMR (300 MHz, CDCl$_3$) (mixture of syn-anti diastereoisomers): main product: δ 8.09 (dd, 1H), 7.94 (dd, 1H), 7.79-7.68 (m, 2H); 4.34 (s, 3H). Minority product: δ 8.38 (m, 1H), 8.18 (m, 1H), 7.86-7.78 (m, 2H); 4.39 (s, 3H). ESI$^+$MS: calcd for C$_{14}$H$_7$N$_5$O: 261.24; found: 262.1 (MH$^+$).

9-(Allyloxyimino)-9H-indeno[1,2-b]pyrazine-2,3-dicarbonitrile (13b)

Prepared according to the general procedure A in 15% yield as yellow solid in diastereoisomeric ratio 1:1. $^1$H NMR (300 MHz, DMSO d$_6$) (mixture of syn-anti diastereoisomers): δ 8.43 (m, 1H), 8.22 (m, 1H), 7.90-7.80 (m, 2H), 6.20 (m, 1H), 5.47 (m, 1H), 5.35 (m, 1H), 5.13 (ddd, 2H), and 8.12 (m, 1H), 7.96 (m, 1H), 7.80-7.69 (m, 2H), 6.14 (m, 1H), 5.53 (m, 1H), 5.38 (m, 1H), 5.08 (ddd, 2H). ESI$^+$MS: calcd for C$_{16}$H$_9$N$_5$O: 287.28; found: 288.2 (MH$^+$).

9-Benzyloxyimino-9H-indeno[1,2-b]pyrazine-2,3-dicarbonitrile (13c)

Prepared according to the general procedure A in 32% yield as yellow solid in diastereoisomeric ratio 2:1. $^1$H NMR (300 MHz, DMSO d$_6$) (mixture of syn-anti diastereoisomers): δ 8.42 (m, 1H), 8.21 (m, 1H), 7.88-7.78 (m, 2H), 7.56-7.49 (m, 2H), 7.47-7.33 (m, 3H), 5.67 (s, 2H) and 8.11 (m, 1H), 7.97 (m, 1H), 7.79-7.69 (m, 2H), 7.56-7.49 (m, 2H), 7.47-7.33 (m, 3H), 5.63 (s, 2H). ESI$^+$MS: calcd for C$_{20}$H$_{11}$N$_5$O: 337.34; found: 338.2 (MH$^+$).

9-Ethoxyimino-9H-indeno[1,2-b]pyrazine-2,3-dicarbonitrile (13d)

Prepared according to the general procedure A in 28% yield as yellow solid in diastereoisomeric ratio 7:3. $^1$H NMR (300 MHz, DMSO d$_6$) (mixture of syn-anti diastereoisomers): δ 8.44 (m, 1H), 8.22 (m, 1H), 7.84 (m, 2H), 4.65 (q, 2H), 1.48 (t, 3H) and 8.12 (m, 1H), 7.98 (m, 1H), 7.75 (m, 2H), 4.61 (q, 2H), 1.44 (t, 3H). ESI$^+$MS: calcd for C$_{15}$H$_9$N$_5$O: 275.27; found: 276.2 (MH$^+$).

Synthesis of 9-[phenylimino]-9H-indeno[1,2-b]pyrazine-2,3-dicarbonitrile (14)

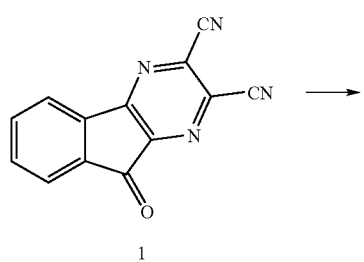

1

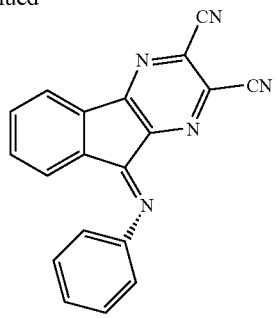

14

To a suspension of 1 (118 mg, 0.51 mmol) and molecular sieves in toluene (3 ml) aniline (0.037 ml, 0.41 mmol) was added. The mixture was heated by MW (150° C., 10 min), then the solvent was evaporated and the crude purified by flash chromatography on silica (petroleum spirit/EtOAc 9:1), affording 14 (93 mg, 60%) as red solid in diastereoisomeric ratio 7:3.

$^1$H NMR (300 MHz, CDCl$_3$): δ 8.14 (d, 1H), 7.65 (dd, 1H), 7.50 (dd, 2H), 7.44-7.29 (m, 3H), 7.05 (d, 2H). ESI$^+$MS: calcd for C$_{19}$H$_9$N$_5$: 307.32; found: 308.0 (MH$^+$).

General Procedure B: Synthesis of 1,2-indandiones

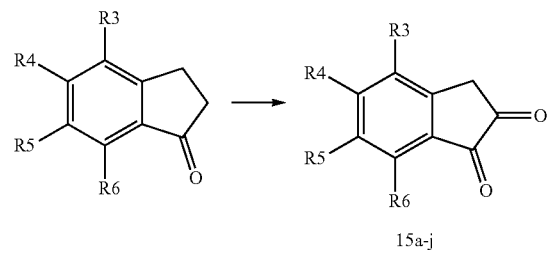

15a-j a R5 = OMe, R3 = R4 = R6 = H
b R4 = R5 = OMe, R3 = R6 = H
c R3 = Me, R4 = R5 = R6 = H
d R3 = R4 = OMe, R5 = R6 = H
e R5 = Me, R3 = R4 = R6 = H
f R3 = R6 = OMe, R4 = R5 = H
g R4 = Cl, R3 = R5 = R6 = H
h R4 = F, R3 = R5 = R6 = H
i R4 = OMe, R3 = R5 = R6 = H
j R4 = OH, R3 = R5 = R6 = H

To a suspension of substituted 1-indanone (5 mmol) in MeOH (12 ml) warmed to 40° C. isopentyl nitrite (0.73 ml, 5.5 mmol) and HCl 37% (0.5 ml) were added. After 1 hour at 40° C. the formed precipitate was collected by filtration, washed with MeOH and dried under vacuum. The solid obtained was suspended in CH$_2$O (36% aqueous, 1.6 ml) and HCl 37% (3.2 ml) and the mixture was stirred at room temperature for 16 hours. Water (20 ml) was added and the suspension was extracted with CH$_2$Cl$_2$ (3×15 ml). Collected organic phases were dried over Na$_2$SO$_4$, filtered and evaporated. The crude product was used without further purification.

6-Methoxy-indan-1,2-dione (15a)

Prepared according to the general procedure B in 60% yield as yellow solid. ESI$^+$MS: calcd for C$_{10}$H$_8$O$_3$: 176.17; found: 177.0 (MH$^+$).

5,6-Dimethoxy-indan-1,2-dione (15b)

Prepared according to the general procedure B in 95% yield as light brown solid. ESI+MS: calcd for $C_{11}H_{10}O_4$: 206.20; found: 207.0 (MH+).

4-Methyl-indan-1,2-dione (15c)

Prepared according to the general procedure B in 60% yield as yellow solid. ESI+MS: calcd for $C_{10}H_8O_2$: 160.17; found: 161.0 (MH+).

4,5-Dimethoxy-indan-1,2-dione (15d)

Prepared according to the general procedure B in 94% yield as yellow solid. ESI+MS: calcd for $C_{11}H_{10}O_4$: 206.20; found: 207.0 (MH+).

6-Methyl-indan-1,2-dione (15e)

Prepared according to the general procedure B in 61% yield as yellow solid. ESI+MS: calcd for $C_{10}H_8O_2$: 160.17; found: 161.0 (MH+).

4,7-Dimethoxy-indan-1,2-dione (15f)

Prepared according to the general procedure B in 52% yield as light brown solid. ESI+MS: calcd for $C_{11}H_{10}O_4$: 206.20; found: 207.0 (MH+).

5-Chloro-indan-1,2-dione (15g)

Prepared according to the general procedure B in 57% yield as yellow solid. ESI+MS: calcd for $C_9H_5ClO_2$: 180.59; found: 181.0 (MH+).

5-Fluoro-indan-1,2-dione (15h)

Prepared according to the general procedure B in 63% yield as yellow solid. ESI+ MS: calcd for $C_9H_5FO_2$: 164.14; found: 165.0 (MH+).

5-Methoxy-indan-1,2-dione (15i)

Prepared according to the general procedure B in 70% yield as yellow solid. ESI+MS: calcd for $C_{10}H_8O_3$: 176.17; found: 177.1 (MH+).

5-Hydroxy-indan-1,2-dione (15j)

Prepared according to the general procedure B in 64% yield as yellow solid. ESI+MS: calcd for $C_9H_6O_3$: 162.15; found: 163.0 (MH+).

General Procedure C: Pyrazine Ring Formation

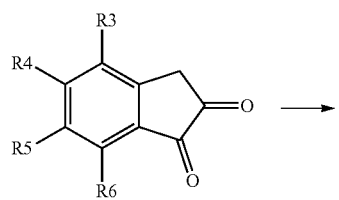

15a-f

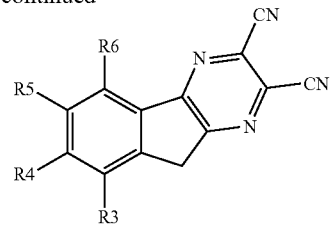

16a-f a R5 = OMe, R3 = R4 = R6 = H
b R4 = R5 = OMe, R3 = R6 = H
c R3 = Me, R4 = R5 = R6 = H
d R3 = R4 = OMe, R5 = R6 = H
e R5 = Me, R3 = R4 = R6 = H
f R3 = R6 = OMe, R4 = R5 = H

To a suspension of 15 (3 mmol) in iPrOH (15 ml) a suspension of diamino-maleodinitrile (324 mg, 3 mmol) in iPrOH (15 ml) was added. The mixture was stirred at room temperature for 24 hours, then, the precipitate was collected by filtration, washed with EtOH and dried under vacuum.

6-Methoxy-9H-indeno[1,2-b]pyrazine-2,3-dicarbonitrile (16a)

Prepared according to the general procedure C in 65% yield as brown solid. ESI+MS: calcd for $C_{14}H_8N_4O$: 248.25; found: 249.0 (MH+).

6,7-Dimethoxy-9H-indeno[1,2-b]pyrazine-2,3-dicarbonitrile (16b)

Prepared according to the general procedure C in 91% yield as light brown solid. ESI+MS: calcd for $C_{15}H_{10}N_4O_2$: 278.27; found: 279.0 (MH+).

8-Methyl-9H-indeno[1,2-b]pyrazine-2,3-dicarbonitrile (16c)

Prepared according to the general procedure C in 60% yield as light brown solid. $^1$H NMR (300 MHz, CDCl$_3$): δ 8.03 (d, 1H), 7.57-7.46 (m, 2H), 4.03 (s, 2H), 2.50 (s, 3H). ESI+MS: calcd for $C_{14}H_8N_4$: 232.25; found: 233.0 (MH+).

7,8-Dimethoxy-9H-indeno[1,2-b]pyrazine-2,3-dicarbonitrile (16d)

Prepared according to the general procedure C in 72% yield as yellow solid. $^1$H NMR (300 MHz, CDCl$_3$): δ 7.90 (d, 1H), 7.17 (d, 1H), 4.10 (s, 2H); 4.02 (s, 3H), 4.01 (s, 3H). ESI+MS: calcd for $C_{15}H_{10}N_4O_2$: 278.27; found: 279.2 (MH+).

6-Methyl-9H-indeno[1,2-b]pyrazine-2,3-dicarbonitrile (16e)

Prepared according to the general procedure C in 48% yield as light brown solid. ESI+MS: calcd for $C_{14}H_8N_4$: 232.25; found: 233.0 (MH+).

5,8-Dimethoxy-9H-indeno[1,2-b]pyrazine-2,3-dicarbonitrile (16f)

Prepared according to the general procedure C in 45% yield as light brown solid. ESI+MS: calcd for $C_{15}H_{10}N_4O_2$: 278.27; found: 278.9 (MH+).

General Procedure D: Oxidation of Methylenic Group

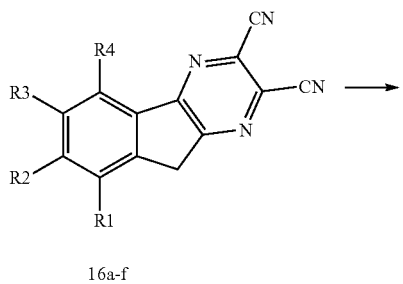

16a-f

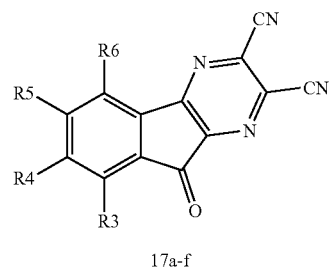

17a-f a R5 = OMe, R3 = R4 = R6 = H
b R4 = R5 = OMe, R3 = R6 = H
c R3 = Me, R4 = R5 = R6 = H
d R3 = R4 = OMe, R5 = R6 = H
e R5 = Me, R3 = R4 = R6 = H
f R3 = R6 = OMe, R4 = R5 = H

To a suspension of 16 (0.8 mmol) in AcOH (1.6 ml) a suspension of $K_2Cr_2O_7$ (434 mg, 1.44 mmol) in ACOH (0.8 ml) and water (0.2 ml) was added. The mixture was slowly heated to 100° C. and it was vigorously stirred at this temperature for 1 hour. The hot suspension was poured in water (10 ml) and the precipitate collected by filtration, washed with water and dried under vacuum.

6-Methoxy-9-oxo-9H-indeno[1,2-b]pyrazine-2,3-dicarbonitrile (17a)

Prepared according to the general procedure D in 70% yield as light brown solid. $^1$H NMR (300 MHz, CDCl$_3$) δ7.92 (d, 1H), 7.48 (d, 1H), 7.18 (dd, 1H), 4.04 (s, 3H). ESI$^+$MS: calcd for $C_{14}H_6N_4O_2$: 262.23; found: 263.0 (MH$^+$).

6,7-Dimethoxy-9-oxo-9H-indeno[1,2-b]pyrazine-2,3-dicarbonitrile (17b)

Prepared according to the general procedure D in 37% yield as red solid. $^1$H NMR (300 MHz, CDCl$_3$): δ 7.39 (s, 1H), 7.37 (s, 1H), 4.10 (s, 3H), 4.03 (s, 3H). ESI$^+$MS: calcd for $C_{15}H_8N_4O_3$: 292.26; found: 293.0 (MH$^+$).

8-Methyl-9-oxo-9H-indeno[1,2-b]pyrazine-2,3-dicarbonitrile (17c)

Prepared according to the general procedure D in 91% yield as yellow solid. $^1$H NMR (300 MHz, DMSO d$_6$ 368K): δ 7.90 (d, 1H), 7.79 (dd, 1H), 7.61 (d, 1H); 2.69 (s, 3H). ESI$^+$MS: calcd for $C_{14}H_6N_4O$: 246.23; found: 247.0 (MH$^+$).

7,8-Dimethoxy-9-oxo-9H-indeno[1,2-b]pyrazine-2,3-dicarbonitrile (17d)

Prepared according to the general procedure D in 71% yield as red solid. $^1$H NMR (300 MHz, DMSO d$_6$ 368K): δ 7.74 (d, 1H), 7.49 (bd, 1H), 4.07 (s, 3H), 3.99 (s, 3H). ESI$^+$MS: calcd for $C_{15}H_8N_4O_3$: 292.26; found: 293.0 (MH$^+$).

6-Methyl-9-oxo-9H-indeno[1,2-b]pyrazine-2,3-dicarbonitrile (17e)

Prepared according to the general procedure D in 73% yield as yellow solid. $^1$H NMR (300 MHz, DMSO d$_6$): δ 7.95 (d, 1H), 7.86 (d, 1H), 7.63 (dd, 1H), 2.52 (s, 3H). ESI$^+$MS: calcd for $C_{14}H_6N_4O$: 246.23; found: 247.0 (MH$^+$).

5,8-Dimethoxy-9-oxo-9H-indeno[1,2-b]pyrazine-2,3-dicarbonitrile (17f)

Prepared according to the general procedure D in 68% yield as brown solid. $^1$H NMR (300 MHz, CDCl$_3$): δ 7.35 (d, 1H), 7.24 (d, 1H), 4.06 (s, 3H), 4.05 (s, 3H). ESI$^+$MS: calcd for $C_{15}H_8N_4O_3$: 292.26; found: 293.0 (MH$^+$).

General Procedure E: One-Pot Pyrazine Ring Formation and Oxidation

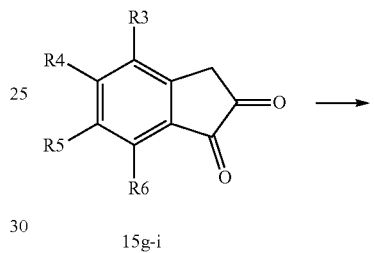

15g-i

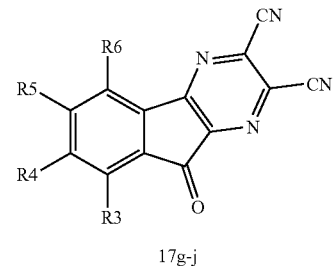

17g-j g R4 = Cl, R3 = R5 = R6 = H
h R4 = F, R3 = R5 = R6 = H
i R4 = OMe, R3 = R5 = R6 = H
j R4 = OH, R3 = R5 = R6 = H

To a suspension of 15 (3 mmol) in iPrOH (15 ml) a suspension of diamino-maleodinitrile (324 mg, 3 mmol) in iPrOH (15 ml) was added. The mixture was stirred at room temperature for 24 hours then for 48 hours at 80° C. The precipitate was collected by filtration, washed with EtOH and dried under vacuum.

7-Chloro-9-oxo-9H-indeno[1,2-b]pyrazine-2,3-dicarbonitrile (17g)

Prepared according to the general procedure E in 40% as yellow solid. $^1$H NMR (300 MHz, DMSO d$_6$): δ 8.13 (d, 1H), 8.04 (bs, 1H), 7.97 (bd, 1H). ESI$^+$MS: calcd for $C_{13}H_3ClN_4O$: 266.65; found: 266.9 (MH$^+$).

7-Fluoro-9-oxo-9H-indeno[1,2-b]pyrazine-2,3-dicarbonitrile (17h)

Prepared according to the general procedure E in 55% as pink solid. $^1$H NMR (300 MHz, CDCl$_3$): δ 8.03 (dd, 1H), 7.74 (dd, 1H), 7.42 (ddd, 1H). ESI$^+$MS: calcd for $C_{13}H_3FN_4O$: 250.19; found: 251.0 (MH$^+$).

7-Methoxy-9-oxo-9H-indeno[1,2-b]pyrazine-2,3-dicarbonitrile (17i)

Prepared according to the general procedure E in 23% as light brown solid. $^1$H NMR (300 MHz, CDCl$_3$): δ 7.92 (d, 1H), 7.48 (d, 1H), 7.18 (dd, 1H), 4.03 (s, 3H). ESI$^+$MS: calcd for C$_{14}$H$_6$N$_4$O$_2$: 262.23; found: 263.0 (MH$^+$).

7-Hydroxy-9-oxo-9H-indeno[1,2-b]pyrazine-2,3-dicarbonitrile (17j)

Prepared according to the general procedure E in 35% as orange solid. The product was not purified by precipitation but, after evaporation of the solvent, by flash chromatography (CH$_2$Cl$_2$/MeOH 9:1). $^1$H NMR (300 MHz, DMSO d$_6$): δ 11.66 (bs, 1H), 7.84 (d, 1H), 7.30 (d, 1H), 7.09 (dd, 1H). ESI$^+$MS: calcd for C$_{13}$H$_4$N$_4$O$_2$: 248.20; found: 249.0 (MH$^+$).

Synthesis of benzo[b]thiophene-2,3-dione (18)

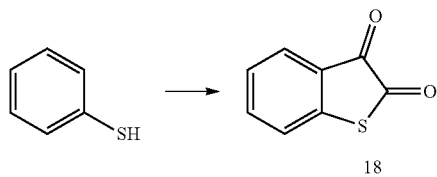 [SMILES: Sc1ccccc1 ; O=C1Sc2ccccc2C1=O]

To a solution of benzenthiol (1 ml, 9.7 mmol) in Et$_2$O (30 ml) at 0° C. oxalyl chloride (0.94 ml, 10.7 mmol) was added dropwise. The mixture was stirred at room temperature for 1.5 hour, then, the solvent was evaporated under reduced pressure. The crude was dissolved in CH$_2$Cl$_2$ (40 ml) and a solution of AlCl$_3$ (4.75 g, 35 mmol) in CH$_2$Cl$_2$ (32 ml) was added dropwise at 0° C. The mixture was stirred for 16 hours at room temperature, then, ice and 1M HCl were added until a clear mixture was obtained. After 1 hour, the phases were separated and the aqueous layer was extracted with CH$_2$Cl$_2$ (3×30 ml). The collected organic phases were dried over Na$_2$SO$_4$, filtered and evaporated, affording 18 (1.2 g, 78%) as orange solid that was used without further purification.

ESI$^+$MS: calcd for C$_8$H$_4$O$_2$S: 164.18; found: 165.1 (MH$^+$).

Synthesis of benzo[4,5]thieno[2,3-b]pyrazine-2,3-dicarbonitrile (19)

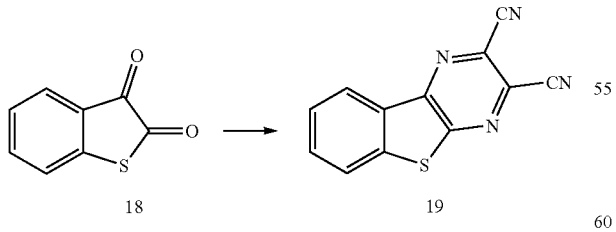

18 (300 mg, 1.83 mmol) and diaminomaleodinitrile (198 mg, 1.83 mmol) were added to boiling water (10 ml). The mixture was refluxed for 1 h then the crude precipitate was filtered, suspended in MeOH and refluxed for 10 min. After cooling at room temperature, the solid was filtered and dried under vacuum, yielding 19 (216 mg, 50%) as brown powder.

$^1$H NMR (300 MHz, DMSO d$_6$): δ 8.58 (d, 1H), 8.38 (d, 1H), 7.94 (dd, 1H), 7.80 (dd, 1H). ESI$^+$MS: calcd for C$_{12}$H$_4$N$_4$S: 236.26; found: 237.1 (MH$^+$).

Synthesis of 5,10-dioxo-5,10-dihydro-benzo[g]quinoxaline-2,3-dicarbonitrile (20)

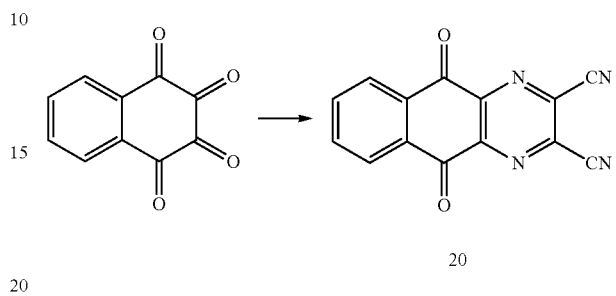

A suspension of 1,2,3,4-tetraoxo-1,2,3,4-tetrahydro-naphtaline dihydrate (214 mg, 0.95 mmol) and diamminomaleodinitrile (102 mg, 0.95 mmol) in EtOH (9.5 ml) and a catalytic amount of AcOH was stirred at room temperature for 24 hours. The precipitate was collected by filtration, washed with EtOH and dried under vacuum, obtaining 20 (65 mg, 35%) as light brown solid.

$^1$H NMR (300 MHz, DMSO d$_6$): δ 9.16 (m, 2H), 8.24 (m, 2H).

Synthesis of 2-cyano-9-oxo-9H-indeno[1,2-b]pyrazin-3-yl-cyanamide (21)

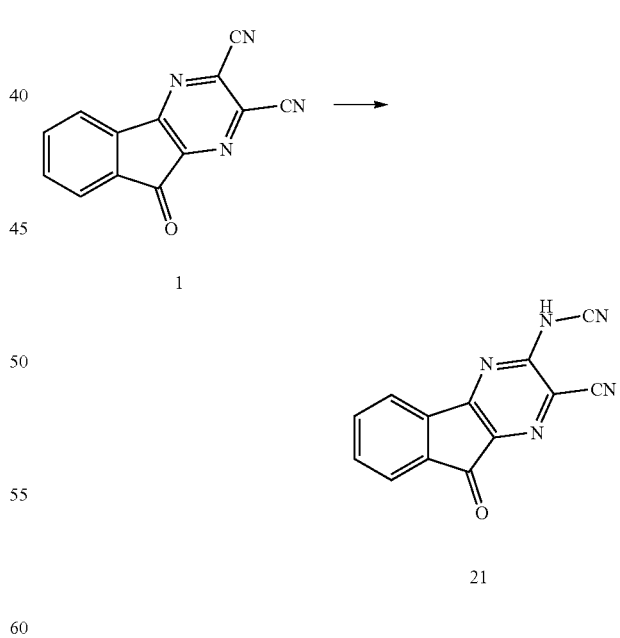

Under inert atmosphere, cyanamid (44 mg, 1.037 mmol) was dissolved in dry DMF (1 ml) and NaH (21 mg, 0.519 mmol) was added in one portion. After 20 min, a solution of 1 (96 mg, 0.415 mmol) in dry DMF (2 ml) was added dropwise. After 1 h the solvent was evaporated and the crude purified by flash chromatography (CH$_2$Cl$_2$/MeOH 8:2) affording 21 (84 mg, 82%) as orange solid.

$^1$H NMR (300 MHz, DMSO d$_6$): δ 7.85 (ddd, 1H), 7.77 (ddd, 1H), 7.76 (m, 1H), 7.67 (ddd, 1H). ESI$^+$MS: calcd for C$_{13}$H$_5$N$_5$O: 247.22; found: 248.1 (MH$^+$).

Synthesis of 3-(1-cyano-2-ethoxy-2-hydroxy-vinyl)-9-oxo-9H-indeno[1,2-b]pyrazine-2-carbonitrile (22)

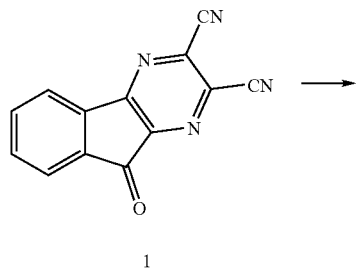

1

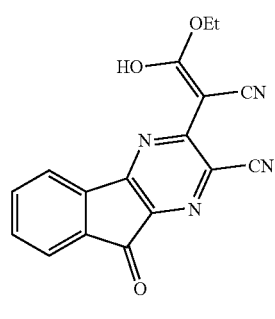

22

Ethylcyanoacetate (110 mg, 0.970 mmol) was dissolved, under inert atmosphere, in dry DMF (1 ml) and NaH (39 mg, 0.970 mmol) was added in one portion. After 30 min, a solution of 1 (150 mg, 0.646 mmol) in dry DMF (2 ml) was added dropwise. After 15 min MeOH was added and the solution stirred for 10 min. The solvents were evaporated and the crude purified by flash chromatography (EtOAc:MeOH 9:1) affording 22 as a dark red solid (200 mg, 97%).

$^1$H NMR (300 MHz, DMSO d$_6$): δ 7.78-7.55 (m, 4H), 4.11 (q, 2H), 1.22 (t, 3H). ESI$^+$MS: calcd for C$_{17}$H$_{10}$N$_4$O$_3$: 318.29; found: 319.2 (MH$^+$).

Synthesis of 3-ethylsulfanyl-9-oxo-9H-indeno[1,2-b]pyrazine-2-carbonitrile (23)

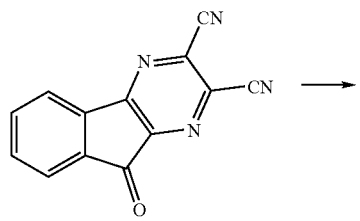

9

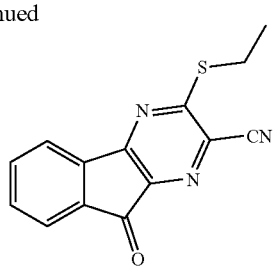

23

To a mixture of ethanethiol (62 μl, 0.84 mmol) and 1N NaOH (0.5 ml, 0.5 mmol) in THF (2.1 ml) 9 (101 mg, 0.42 mmol) was added. The mixture was stirred at room temperature for 30 min then the solvent was evaporated under reduced pressure. The residue was dissolved in H$_2$O (4 ml) and extracted with CH$_2$Cl$_2$ (2×4 ml). The collected organic phases were dried over Na$_2$SO$_4$, filtered and evaporated. The crude was purified by flash chromatography (CH$_2$Cl$_2$) affording 23 (98 mg, 87%) as orange solid.

$^1$H NMR (300 MHz, CDCl$_3$): δ 7.92 (d, 1H), 7.86 (d, 1H), 7.73 (ddd, 1H), 7.63 (ddd, 1H), 3.44 (q, 2H), 1.51 (t, 3H). ESI$^+$MS: calcd for C$_{14}$H$_9$N$_3$OS: 267.31; found: 268.1 (MH$^+$).

General Procedure F: Synthesis of Alkyloxyimines

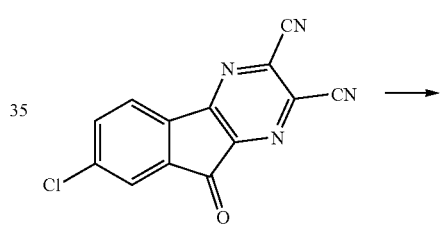

17g

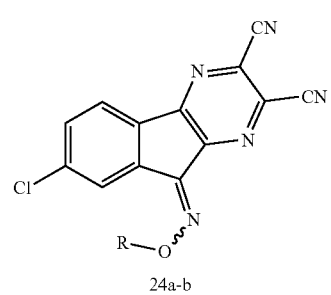

24a-b
a R = Me
b R = CH$_2$—CH═CH$_2$

To a suspension of 17g (151 mg, 0.56 mmol) in pyridine (5.6 ml) O-alkyl-hydroxylamine hydrochloride (1.68 mmol) and molecular sieves were added and the mixture was stirred at 60° C. for 1.5h. The insoluble residue was filtered, the solvent evaporated and the crude purified by flash chromatography on silica (petroleum spirit/CH$_2$Cl$_2$ 1:1).

7-Chloro-9-methoxyimino-9H-indeno[1,2-b]pyrazine-2,3-dicarbonitrile (24a)

Prepared according to the general procedure F in 65% yield as light brown solid in diastereoisomeric ratio 1:1. $^1$H NMR (300 MHz, CDCl$_3$) (mixture of syn-anti diastereoisomers): δ 8.36 (d, 1H), 8.04 (d, 1H), 7.64 (dd, 1H), 4.43 (s, 3H) and 7.94 (d, 1H), 7.89 (d, 1H), 7.54 (dd, 1H), 4.36 (s, 3H). ESI$^+$MS: calcd for C$_{14}$H$_6$ClN$_5$O: 295.69; found: 296.0 (MH$^+$).

9-Allyloxyimino-7-chloro-9H-indeno[1,2-b]pyrazine-2,3-dicarbonitrile (24b)

Prepared according to the general procedure F in 56% yield as light brown solid in diastereoisomeric ratio 1:1. $^1$H NMR (300 MHz, CDCl$_3$) (mixture of syn-anti diastereoisomers): δ 8.41 (d, 1H), 8.07 (d, 1H), 7.67 (dd, 1H), 6.22-6.03 (m, 1H), 5.47 (m, 1H), 5.36 (m, 1H), 5.15 (m, 2H) and 7.97 (d, 1H), 7.94 (d, 1H), 7.57 (dd, 1H), 6.22-6.03 (m, 1H), 5.47 (m, 1H), 5.40 (m, 1H), 5.05 (m, 2H). ESI$^+$MS: calcd for C$_{16}$H$_8$ClN$_5$O: 321.73; found: 322.1 (MH$^+$).

6-Chloro-9-oxo-9H-indeno[1,2-b]pyrazine-2,3-dicarbonitrile (25)

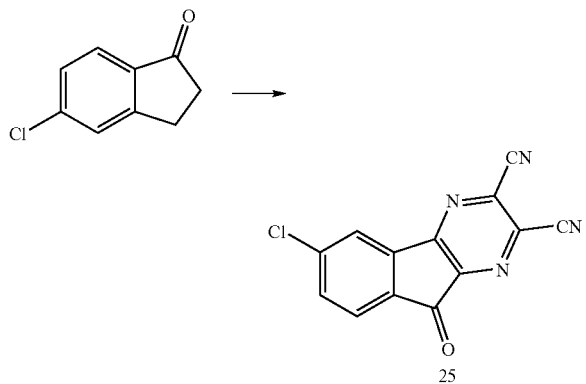

25

A mixture of 5-chloro-1-indanone (1.05 g, 6.28 mmol) and N-bromosuccinimide (2.23 g, 12.56 mmol) in DMSO (25 ml) was stirred overnight at 40° C. and 5 h at 80° C. under vacuum. Water (125 ml) was added and the mixture was extracted with CH$_2$Cl$_2$ (25 ml). The aqueous phase was saturated with brine and solid NaCl and extracted with CH$_2$Cl$_2$ (4×80 ml). The collected organic phases were dried over Na$_2$SO$_4$ and the solvent evaporated. The crude was dissolved in EtOH (63 ml), diaminomaleonitrile (678 mg, 6.28 mmol) and a catalytic amount of AcOH were added and the mixture stirred at 80° C. for 45 min. The precipitate was collected by filtration and washed with EtOH (464 mg). The filtered solution was evaporated and the crude purified by flash.

Synthesis of 2-(2-cyano-9-oxo-9H-indeno[1,2-b]pyrazin-3-yl)-acetamide (26)

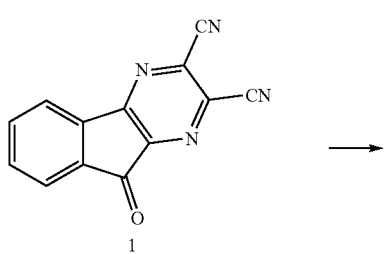

1

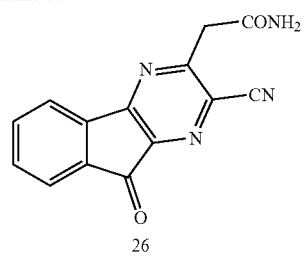

26

The procedure for the preparation of the starting material 1 was described in a previous experimental section.

tert-Butyl cyanoacetate (292 mg, 2.07 mmol) was dissolved, under inert atmosphere, in dry DMF (4 ml) and NaH (60% dispersion in mineral oil, 90 mg, 2.24 mmol) was added portionwise. After 15 min, a solution of 1 (400 mg, 1.72 mmol) in dry DMF (3 ml) was added dropwise. After 16 h MeOH was added, the solvents were evaporated and the crude purified by flash chromatography (EtOAc:MeOH 9:1) affording cyano-(2-cyano-9-oxo-9H-indeno[1,2-b]pyrazin-3-yl)-acetic acid tert-butyl ester as dark red solid.

A solution of intermediate in dioxane/H$_2$O/TFA (5:1:1, 7 ml) was stirred at 50° C. for 4 h. The precipitate was collected by filtration and crystallized from CH$_3$CN, affording 26 (172 mg, 38% over 2 steps) as pink solid. $^1$H NMR (300 MHz, DMSO d$_6$): δ 8.22 (bs, 1H), 7.94 (dd, 1H), 7.93 (bs, 1H), 7.85 (dd, 1H), 7.84 (ddd, 1H), 7.69 (ddd, 1H), 4.75 (s, 2H). ESI$^+$MS: calcd for C$_{14}$H$_8$N$_4$O$_2$: 264.25; found: 265.1 (MH$^+$).

General Procedure G: Synthesis of O-alkyloximes

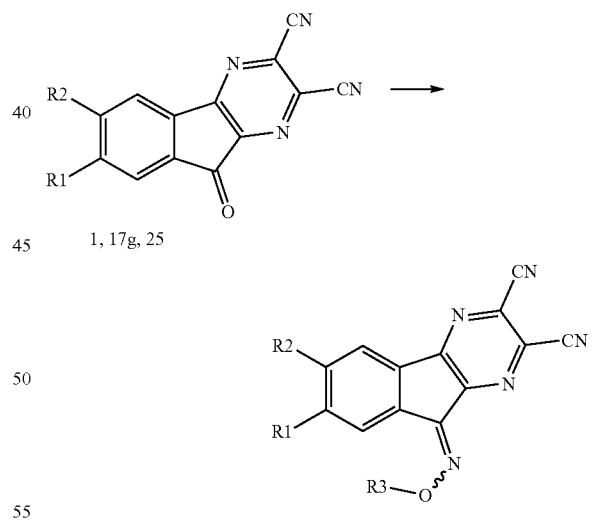

1, a R1 = R2 = H, R3 = —CH$_2$CH$_2$OPh
17g, b R1 = Cl, R2 = H, R3 = —CH$_2$CH$_2$OPh
25, c R1 = H, R2 = Cl, R3 = —CH$_2$CH=CH$_2$

To a suspension of 1, 17, g, 25 (0.72 mmol) in pyridine (7 ml) O-alkyl-hydroxylamine hydrochloride (2.16 mmol) and molecular sieves were added and the mixture was stirred at 60° C. for 2 h. The insoluble residue was filtered, the solvent evaporated and the crude purified by flash chromatography (petroleum ether/CH$_2$Cl$_2$ 1:1).

9-(2-Phenoxy-ethoxyimino)-9H-indeno[1,2-b]pyrazine-2,3-dicarbonitrile (27a)

Prepared according to the general procedure D in 46% yield as yellow solid in diastereoisomeric ratio 1:1. $^1$H NMR (300 MHz, DMSO d$_6$) (mixture of syn-anti diastereoisomers): δ 8.11 (d, 1H), 7.98 (d, 1H), 7.75 (m, 2H), 7.28 (m, 2H), 7.01 (m, 2H), 6.93 (m, 1H), 4.89 (m, 2H), 4.46 (m, 2H) and 8.40 (d, 1H), 8.21 (d, 1H), 7.82 (m, 2H), 7.28 (m, 2H), 7.01 (m, 2H), 6.93 (m, 1H), 4.94 (m, 2H), 4.46 (m, 2H). ESI$^+$MS: calcd for $C_{21}H_{13}ClN_5O_2$: 367.37; found: 368.1 (MH$^+$).

7-Chloro-9-(2-phenoxy-ethoxyimino)-9H-indeno[1,2-b]pyrazine-2,3-dicarbonitrile (27b)

Prepared according to the general procedure D in 75% yield as yellow solid in diastereoisomeric ratio 6:4. $^1$H NMR (300 MHz, CDCl$_3$) (mixture of syn-anti diastereoisomers): δ 8.00 (d, 1H), 7.96 (d, 1H), 7.61 (dd, 1H), 7.27 (m, 2H), 6.95 (m, 3H), 4.94 (m, 2H), 4.45 (m, 2H) and 8.46 (d, 1H), 8.09 (d, 1H), 7.70 (dd, 1H), 7.27 (m, 2H), 6.95 (m, 3H), 5.02 (m, 2H), 4.46 (m, 2H). ESI$^+$MS: calcd for $C_{21}H_{12}ClN_5O_2$: 401.82; found: 402.0 (MH$^+$).

9-Allyloxyimino-6-chloro-9H-indeno[1,2-b]pyrazine-2,3-dicarbonitrile (27c)

Prepared according to the general procedure D in 87% yield as light yellow solid in diastereoisomeric ratio 6:4. $^1$H NMR (300 MHz, CDCl$_3$) (mixture of syn-anti diastereoisomers): δ 8.34 (d, 1H), 8.10 (d, 1H), 7.65 (dd, 1H), 6.10 (m, 1H), 5.48 (m, 1H), 5.34 (m, 1H), 5.11 (m, 2H) and 8.01 (d, 1H), 7.88 (d, 1H), 7.58 (dd, 1H), 6.10 (m, 1H), 5.42 (m, 1H), 5.33 (m, 1H), 5.03 (m, 2H). ESI$^+$MS: calcd for $C_{16}H_8ClN_5O$: 321.73; found: 322.1 (MH$^+$).

General Procedure H: Synthesis of Substituted 1-indanones

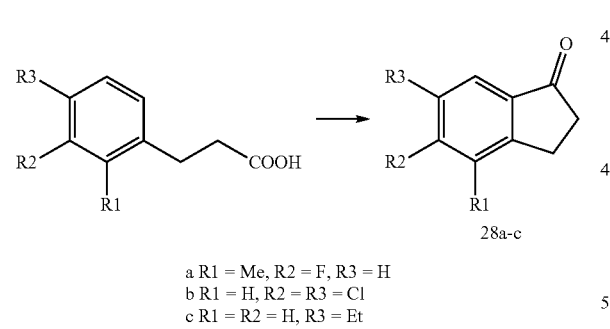

a R1 = Me, R2 = F, R3 = H
b R1 = H, R2 = R3 = Cl
c R1 = R2 = H, R3 = Et

5-Fluoro-4-methyl-indan-1-one (28a)

A solution of 3-fluoro-2-methyl benzaldehyde (1.9 g, 14.0 mmol), malonic acid (2.2 g, 21.0 mmol) and piperidine (138 μl, 1.4 mmol) in pyridine (14 ml) was refluxed for 16 h. After cooling, 6N HCl was added up to pH=1, then the precipitate was collected by filtration and washed with H$_2$O.

The dried solid was hydrogenated at 30 psi for 2 h using a Parr apparatus with 10% Pd/C (0.2 g) as catalyst and MeOH (140 ml) as solvent. The suspension was filtered through a Celite pad and the solvent was evaporated under reduced pressure.

To a solution of aryl propionic acid (2.24 g, 12.3 mmol) in CH$_2$Cl$_2$ (61 ml), oxalyl chloride (3.2 ml, 36.9 mmol) and few drops of DMF were added and the mixture was stirred for 1 h at room temperature. The solvent was evaporated and the residue was added, dissolved in CH$_2$Cl$_2$ (61 ml), to a suspension of AlCl$_3$ (4.92 g, 36.9 mmol) in CH$_2$Cl$_2$ (61 ml) cooled at 0° C. The mixture for refluxed for 16 h and then it was poured in ice. The phases were separated and the aqueous one was extracted with CH$_2$Cl$_2$ (2×50 ml). Collected organic phases were dried over Na$_2$SO$_4$, filtered and evaporated. The crude was purified by flash chromatography (petroleum ether/EtOAc 7:3) affording 28a (1.85 g, 76% over 3 steps) as white solid. $^1$H NMR (300 MHz, CDCl$_3$): δ 7.60 (dd, 1H), 7.05 (dd, 1H), 3.03 (dd, 2H), 3.72 (dd, 2H), 2.27 (d, 3H). ESI$^+$MS: calcd for $C_{10}H_9FO$: 164.18; found: 165.2 (MH$^+$).

5,6-Dichloro-indan-1-one (28b)

A mixture of 3,4-dichlorophenyl propionic acid (1.95 g, 8.9 mmol) and polyphosphoric acid (19g) was stirred at 120° C. for 8 h. Ice was added and the mixture was extracted with CH$_2$Cl$_2$ (2×20 ml). Collected organic phases were dried over Na$_2$SO$_4$, filtered and evaporated. The crude was purified by flash chromatography (petroleum ether/EtOAc 8:2) affording the expected 5,6-disubstituted indanone 28b (143 mg, 8%) as white solid. $^1$H NMR (300 MHz, CDCl$_3$): δ 7.82 (s 1H), 7.60 (bs, 1H), 3.11 (dd, 2H), 3.73 (dd, 2H). ESI$^+$MS: calcd for $C_9H_6Cl_2O$: 201.05; found: 202.1 (MH$^+$).

6-Ethyl-indan-1-one (28c)

To a slurry of polyphosphoric acid (20g) heated to 60° C. 4-ethyl-phenyl propionic acid (1.26 g, 7.1 mmol) was added portionwise. The mixture was heated to 80° C. for 2 h and then it was poured into ice. The suspension was extracted with CH$_2$Cl$_2$ (2×10 ml), the organic phase were dried over Na$_2$SO$_4$, filtered and evaporated. The product (1.13 g, 99%) was used without further purification. ESI$^+$MS: calcd for $C_{11}H_{12}O$: 160.22; found: 161.1 (MH$^+$).

General Procedure I: Synthesis of Substituted 1,2-indandiones

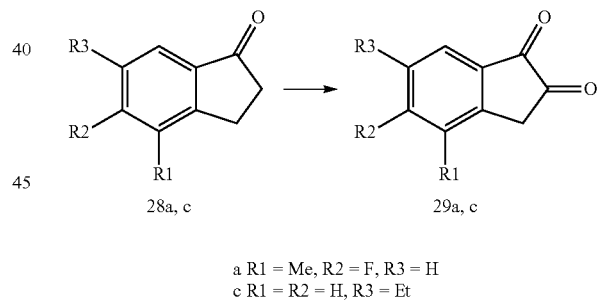

a R1 = Me, R2 = F, R3 = H
c R1 = R2 = H, R3 = Et

To a suspension of substituted 1-indanone (5 mmol) in MeOH (12 ml) warmed to 40° C. isopentyl nitrite (0.73 ml, 5.5 mmol) and HCl 37% (0.5 ml) were added. After 1 h at 40° C. the formed precipitate was collected by filtration, washed with MeOH and dried under vacuum. The solid obtained was suspended in CH$_2$O (36% aqueous, 1.6 ml) and HCl 37% (3.2 ml) and the mixture was stirred at room temperature for 16 h. Water (20 ml) was added and the suspension was extracted with CH$_2$Cl$_2$ (3×15 ml). Collected organic phases were dried over Na$_2$SO$_4$, filtered and evaporated. The crude product was used without further purification.

5-Fluoro-4-methyl-indan-1,2-dione (29a)

Prepared according to the general procedure F in 95% yield as yellow solid. ESI$^+$MS: calcd for $C_{10}H_7FO_2$: 178.16; found: 179.2 (MH$^+$).

6-Ethyl-indan-1,2-dione (29c)

Prepared according to the general procedure F in 98% yield as yellow solid. ESI⁺MS: calcd for $C_{11}H_{10}O_2$: 174.20; found: 175.1 (MH⁺).

Synthesis of 7-Fluoro-8-methyl-9-oxo-9H-indeno[1,2-b]pyrazine-2,3-dicarbonitrile (30)

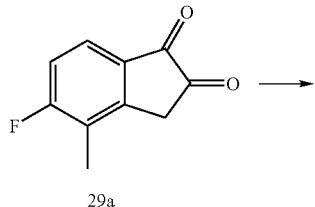

29a

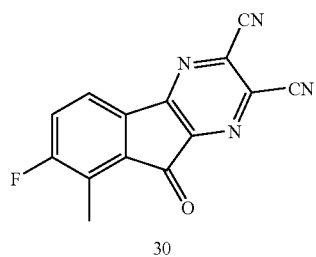

30

To a suspension of 29a (578 mg, 3.24 mmol) in MeOH (32 ml) diaminomaleodinitrile (420 mg, 3.89 mmol) and AcOH (1.6 ml) were added. The mixture was stirred at room temperature for 16 h and then the solvent was evaporated under reduced pressure. The crude was purified by flash chromatography (CH₂Cl₂) affording 7-fluoro-8-methyl-9H-indeno[1,2-b]pyrazine-2,3-dicarbonitrile as light brown solid.

To a suspension of intermediate (2.94 mmol) in 95:5 AcOH/H₂O (10 ml) K₂Cr₂O₇ (865 mg, 2.94 mmol) was added portionwise. The mixture was stirred at 60° C. for 4 h. The hot suspension was poured in water (50 ml) and the precipitate collected by filtration, washed with water and dried under vacuum. The crude was purified by flash chromatography (CH₂Cl₂/petroleum ether 7:3) affording 30 (707 mg, 83% over 2 steps) as orange solid. ¹H NMR (300 MHz, CDCl₃): δ 7.86 (dd, 1H), 7.40 (dd, 1H), 2.62 (s, 3H). ESI⁺MS: calcd for $C_{14}H_5FN_4O$: 264.22; found: 265.1 (MH⁺).

Synthesis of 6,7-dichloro-9-oxo-9H-indeno[1,2-b]pyrazine-2,3-dicarbonitrile (31)

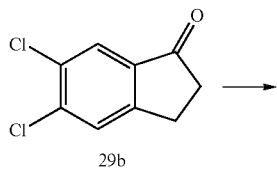

29b

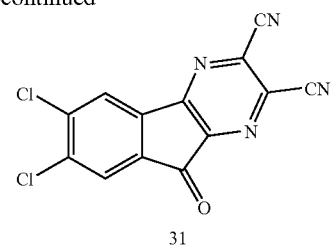

31

A mixture of 29b (161 mg, 0.80 mmol) and N-bromosuccinimide (285 mg, 1.6 mmol) in DMSO (3.2 ml) was stirred overnight: at 40° C. and 5 h at 80° C. under vacuum. Brine (7 ml) was added and the mixture was extracted with CH₂Cl₂ (3×5 ml). The collected organic phases were dried over Na₂SO₄ and the solvent evaporated. The crude was dissolved in EtOH (8 ml), diaminomaleonitrile (112 mg, 1.04 mmol) and a catalytic amount of AcOH were added and the mixture stirred at 80° C. for 2 h. The solvent was evaporated and the crude purified by flash chromatography (CH₂Cl₂/petroleum ether 1:1) affording 31 (30 mg, 13% over 2 steps) as yellow solid. ¹H NMR (300 MHz, CDCl₃): δ 8.07 (s, 1H), 7.96 (s, 1H). ESI⁺MS: calcd for $C_{13}H_2Cl_2N_4O$: 301.09; found: 301.2 (MH⁺).

Synthesis of 6-ethyl-9-oxo-9H-indeno[1,2-b]pyrazine-2,3-dicarbonitrile (32)

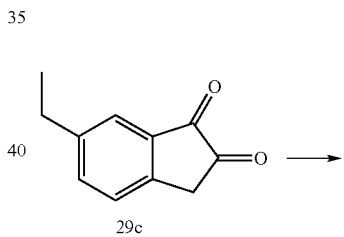

29c

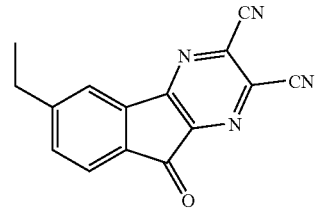

32

A suspension of 29c (298 mg, 1.71 mmol) and diaminomaleonitrile (185 mg, 1.71 mmol) in iPrOH (17 ml) was stirred at 80° C. for 20 h. The solvent was evaporated under reduced pressure and the crude was purified by flash chromatography (CH₂Cl₂). The obtained product was purified by preparative HPLC, obtaining 32 as yellow solid as 7:3 regioisomeric mixture with the 7-ethyl analogue. ¹H NMR (300 MHz, CDCl₃): main product: δ 7.95 (d, 1H), 7.80 (m, 1H), 7.67 (bd, 1H), 2.83 (q, 2H), 1.33 (t, 3H); minority product: δ 7.89 (d, 1H), 7.89 (m, 1H), 7.56 (bd, 1H), 2.86 (q, 2H), 1.36 (t, 3H). ESI⁺MS: calcd for $C_{15}H_8N_4O$: 260.26; found: 261.1 (MH⁺).

Synthesis of 2-cyano-9-[hydroxyimino]-9H-indeno[1,2-b]pyrazine-3-carboxylic acid amide (33)

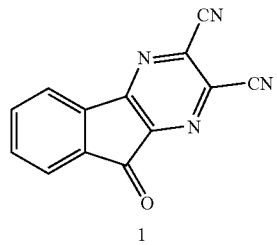

1

To a solution of 1 (4.89 g, 21.0 mmol) in CH₃CN (140 ml) hydroxylamine (50% wt. in water, 2.6 ml, 42 mmol) was added at 0° C. The mixture was stirred at this temperature for 2.5 h, then the formed precipitate was collected by filtration and dried under vacuum, affording 33 (5.41 g, 97%) as light brown solid. ¹H NMR (300 MHz, DMSO d₆): δ 10.96 (s, 1H), 8.11 (d, 1H), 7.89 (dd, 1H), 7.88 (d, 1H), 7.74 (dd, 1H), 6.32 (bs, 2H). ESI⁺MS: calcd for $C_{13}H_7N_5O_2$: 265.23; found: 265.9 (MH⁺).

General Procedure J: Synthesis of 9-alkyloxyimino-9H-indeno[1,2-b]pyrazine-3-carboxylic acid amide

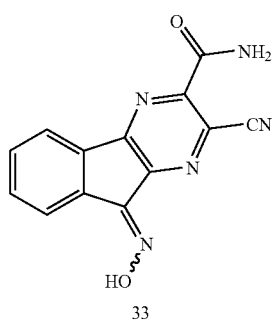

33

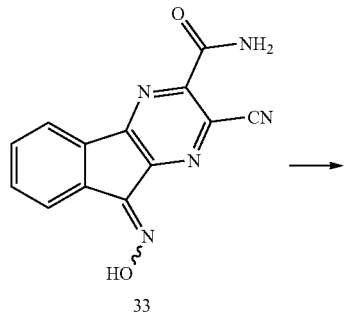

33

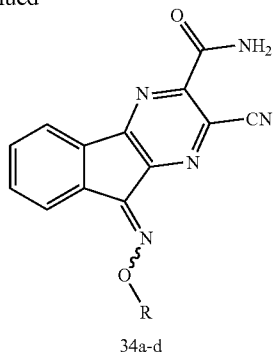

34a-d a R = —CH₂CH═CH₂
b R = Et
c R = —CH₂CH₂OCH₃
d R = Me

A suspension of 33 (610 mg, 2.3 mmol), Cs₂CO₃ (1.5 g, 4.6 mmol), KI (1.14 g, 6.9 mmol) and alkyl bromide (6.9 mmol) in DMF (12 ml) was stirred at 50° C. overnight. The solvent was evaporated under reduced pressure and the crude was purified by flash chromatography (CH₂Cl₂/MeOH 95:5).

9-Allyloxyimino-2-cyano-9H-indeno[1,2-b]pyrazine-3-carboxylic acid amide (34a)

Prepared according to the general procedure G in 35% yield as orange solid in diastereoisomeric ratio 55:45. ¹H NMR (300 MHz, DMSO d₆): δ 8.68 (bs, 2H), 8.00 (d, 1H), 7.90-7.78 (m, 2H), 7.65 (dd, 1H), 6.16-6.01 (m, 1H), 5.42 (m, 1H), 5.28 (m, 1H), 4.78 (ddd, 2H) and 8.56 (bs, 2H), 7.90-7.78 (m, 3H), 7.66 (dd, 1H), 6.16-6.01 (m, 1H), 5.36 (m, 1H), 5.24 (m, 1H), 4.75 (ddd, 2H). ESI⁺MS: calcd for $C_{16}H_{11}N_5O_2$: 305.30; found: 306.1 (MH⁺).

2-Cyano-9-ethoxyimino-9H-indeno[1,2-b]pyrazine-3-carboxylic acid amide (34b)

Prepared according to the general procedure G in 28% yield as yellow solid in diastereoisomeric ratio 6:4. ¹H NMR (300 MHz, CDCl₃): δ 8.05 (d, 1H), 7.77 (d, 1H), 7.67 (m, 1H), 7.52 (m, 1H), 4.48 (q, 2H), 1.42 (t, 3H) and 7.87 (d, 1H), 7.77 (d, 1H), 7.67 (m, 1H), 7.52 (m, 1H), 4.42 (q, 2H), 1.39 (t, 3H). ESI⁺MS: calcd for $C_{15}H_{11}N_5O_2$: 293.29; found: 294.1 (MH⁺).

2-Cyano-9-(2-methoxy-ethoxyimino)-9H-indeno[1,2-b]pyrazine-3-carboxylic acid amide (34c)

Prepared according to the general procedure G in 48% yield as light brown solid in diastereoisomeric ratio 6:4. ¹H NMR (300 MHz, DMSO d₆): δ 8.63 (bs, 2H), 7.89-7.77 (m, 3H), 7.65 (dd, 1H), 4.36 (m, 2H), 3.67 (m, 2H), 3.31 (s, 3H) and 7.99 (bs, 2H), 7.89-7.77 (m, 3H), 7.65 (dd, 1H), 4.33 (m, 2H), 3.67 (m, 2H), 3.30 (s, 3H). ESI⁺MS: calcd for $C_{16}H_{13}N_5O_3$: 323.31; found: 324.1 (MH⁺).

2-Cyano-9-methoxyimino-9H-indeno[1,2-b]pyrazine-3-carboxylic acid amide (34d)

Prepared according to the general procedure G (the reaction mixture was stirred 48 h at room temperature) in 25% yield as orange solid in diastereoisomeric ratio 6:4. ¹H NMR (300 MHz, DMSO d₆): δ 8.10 (m, 1H), 7.89 (m, 2H), 7.74 (m, 1H), 6.61 (bs, 2H), 3.93 (s, 3H) and 8.01 (d, 1H), 7.89 (m, 2H), 7.74 (m, 1H), 6.37 (bs, 2H), 3.89 (s, 3H). ESI+MS: calcd for $C_{14}H_9N_5O_2$: 279.26; found: 280.1 (MH+).

Synthesis of 2-cyano-9-acetoxyimino-9H-indeno[1,2-b]pyrazine-3-carboxylic acid amide (35)

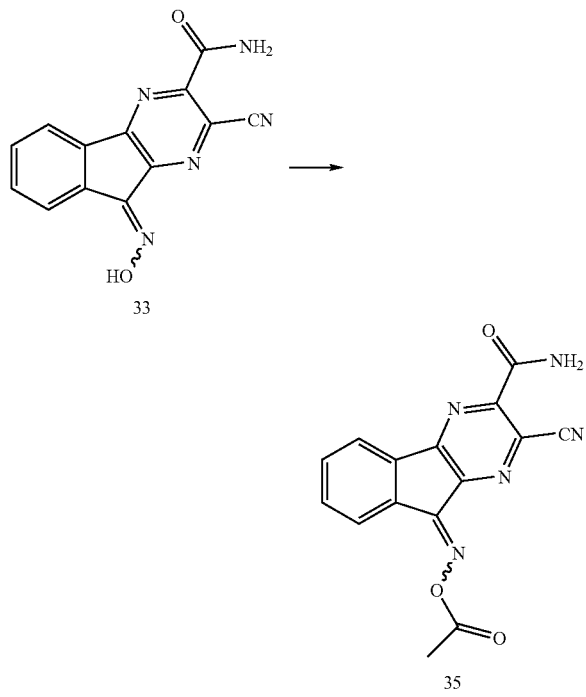

To a solution of 33 (1.0 g, 3.77 mmol) in dry pyridine (30 ml) cooled at 0° C., acetyl chloride (0.8 ml, 11.3 mmol) was added dropwise and the mixture was stirred 16 h at room temperature. Water (40 ml) was added and the precipitate was collected by filtration. The crude was purified by flash chromatography ($CH_2Cl_2$/acetone/MeOH 8:2:0.5) and triturated with $Et_2O/CH_2Cl_2$/MeOH, affording 35 (251 mg, 21%) as yellow solid as single isomer. $^1$H NMR (300 MHz, DMSO $d_6$): δ 8.12 (d, 1H), 7.91 (m, 2H), 7.77 (ddd, 1H), 7.43 (bs, 2H), 2.27 (s, 3H). ESI+MS: calcd for $C_{15}H_9N_5O_3$: 307.27; found: 308.1 (MH+).

Synthesis of 2-cyano-9-oxo-9H-indeno[1,2-b]pyrazine-3-carboxylic acid amide (36)

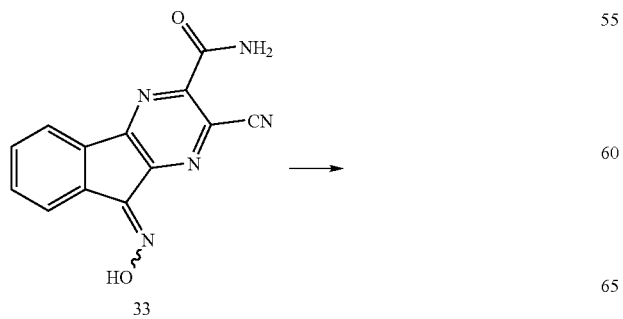

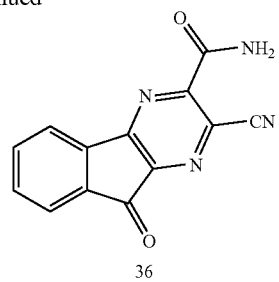

A suspension of 33 (522 mg, 1.97 mmol) and [bis(trifluoroacetoxy)iodo]benzene (1.69 g, 3.9 mmol) in $CH_3CN/H_2O$ (9:1, 20 ml) was stirred 24 h at room temperature. The solid was collected by filtration and washed with $CH_3CN$. The residue was dissolved in DMSO (2 ml) and precipitated by addition of $H_2O$. The obtained solid was filtered and dried under vacuum, affording 36 (286 mg, 58%) as light brown solid. $^1$H NMR (300 MHz, DMSO $d_6$): δ 8.65 (bs, 1H), 8.31 (bs, 1H), 8.09 (dd, 1H), 7.93 (m, 2H), 7.77 (ddd, 1H). ESI+MS: calcd for $C_{13}H_6N_4O_2$: 250.22; found: 251.1 (MH+).

Synthesis of (3-carbamoyl-2-cyano-indeno[1,2-b]pyrazin-9-ylideneaminooxy)-acetic acid ethyl ester (37)

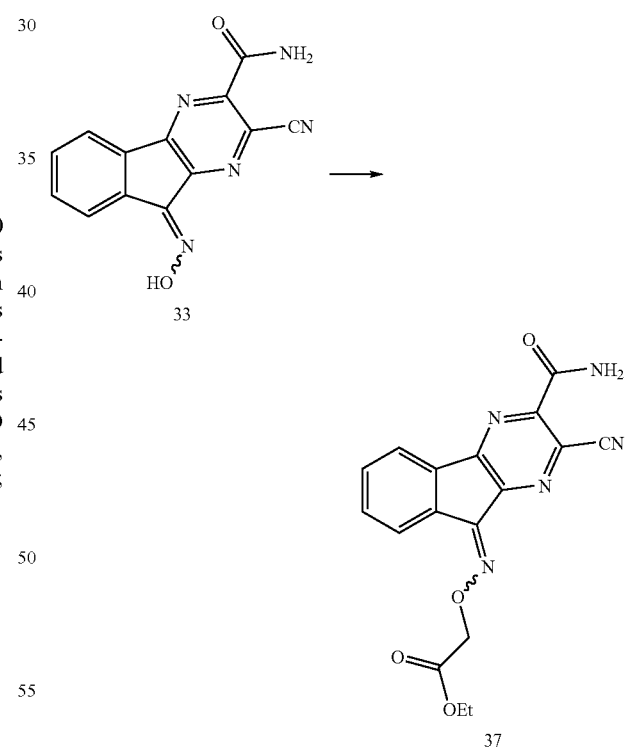

To a suspension of 33 (300 mg, 1.1 mmol) and $Cs_2CO_3$ (405 mg, 1.2 mmol) in DMF (15 ml), ethyl bromoacetate (0.14 ml, 1.26 mmol) was added dropwise and the mixture was stirred at 70° C. for 24 h. The suspension was cooled at room temperature, $H_2O$ (30 ml) was added and the mixture was extracted with $CH_2Cl_2$ (70 ml). The organic phase was dried over $Na_2SO_4$ and the volatile solvent was evaporated under reduced pressure. A 1:1 mixture of n-hexane/iPr$_2$O was added and after 2 h the obtained solid was collected by filtration. The crude was purified by flash chromatography (CH$_2$Cl$_2$/MeOH 85:15) affording 37 (85 mg, 22%) as green-brown solid. $^1$H NMR (300 MHz, DMSO d$_6$): δ 8.78 (bs, 1H), 8.73 (bs, 1H), 8.00 (dd, 1H), 7.82 (m, 2H), 7.67 (ddd, 1H), 4.87 (s, 2H), 4.19 (q, 2H), 1.25 (t, 3H). ESI$^+$MS: calcd for C$_{17}$H$_{13}$N$_5$O$_4$: 351.32; found: 352.1 (MH$^+$).

Synthesis of (3-carbamoyl-2-cyano-indeno[1,2-b]pyrazin-9-ylideneaminooxy)-acetic acid (38)

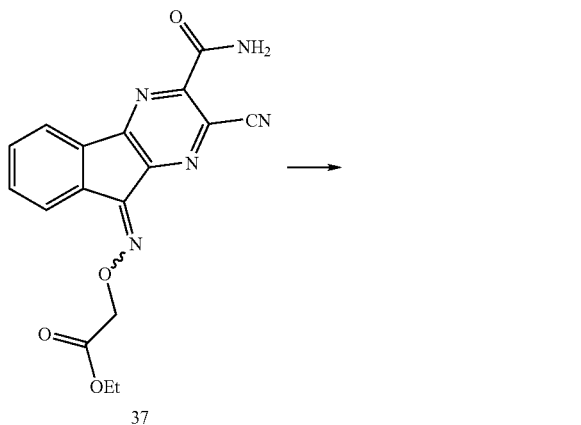

To a solution of 37 (70 mg, 0.2 mmol) in THF/H$_2$O (1:1, 15 ml) LiOH.H$_2$O (41 mg, 1.0 mmol) was added and the mixture was stirred at room temperature. After 2 h 2N HCl was added up to pH=5. The solvent was removed under reduced pressure and the crude was purified by flash chromatography (CH$_2$Cl$_2$/MeOH/AcOH 90:10:1) affording 38 (41 mg, 63%) as yellow solid. ESI$^+$MS: calcd for C$_{15}$H$_9$N$_5$O$_4$: 323.27; found: 324.3 (MH$^+$).

Synthesis of (2-bromo-acetylamino)-acetic acid ethyl ester (39)

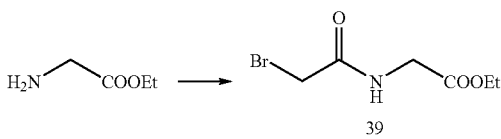 [SMILES: CCOC(=O)CN ; CCOC(=O)CNC(=O)CBr]

To a mixture of glycine ethyl ester hydrochloride (2.0 g, 14.3 mmol) and K$_2$CO$_3$ (2.1 g, 15.2 mmol) in CH$_2$Cl$_2$ (35 ml) cooled at 0-5° C. bromoacetyl bromide (1.36 ml, 15.6 mmol) was added dropwise. The suspension was stirred at room temperature and after 3 h H$_2$O (20 ml) was added. The phases were separated and the organic one was washed with a saturated solution of NaHCO$_3$ (20 ml) and H$_2$O (20 ml) and dried over Na$_2$SO$_4$. The solvent was evaporated obtaining 39 as white solid (1.2 g, 40%). ESI$^+$MS: calcd for C$_6$H$_{10}$BrNO$_3$: 224.06; found: 224.0 and 226.0 (MH$^+$).

Synthesis of [2-(3-carbamoyl-2-cyano-indeno[1,2-b]pyrazin-9-ylideneaminooxy)-acetylamino]-acetic acid ethyl ester (40)

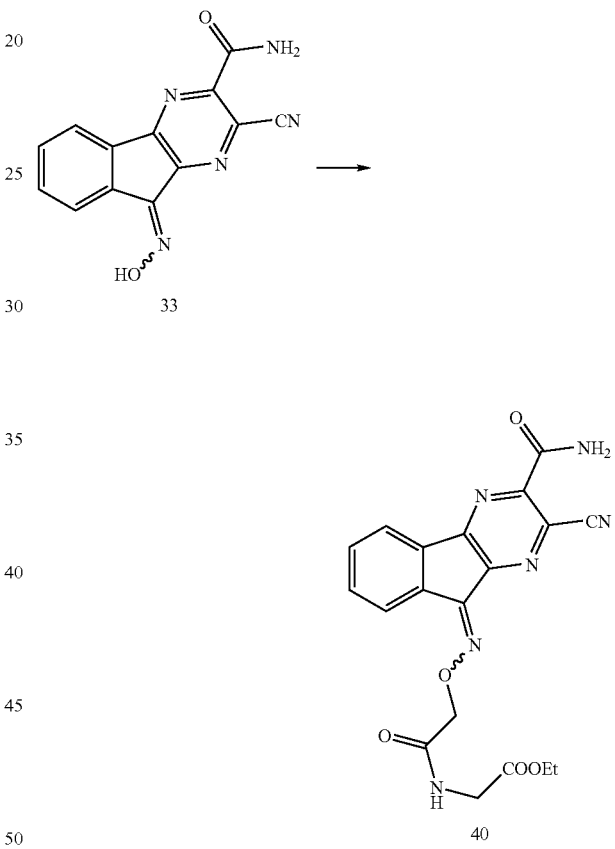

To a suspension of 33 (212 mg, 0.80), Cs$_2$CO$_3$ (260 mg, 0.80) in DMF (15 ml), 39 (200 mg, 0.89 mmol) was added portionwise and the mixture was stirred at room temperature for 2 days. H$_2$O (30 ml) was added and the suspension was extracted with CH$_2$Cl$_2$ (70 ml). The organic phase was dried over Na$_2$SO$_4$ and the solvent was evaporated under reduced pressure. The crude was purified by flash chromatography (CH$_2$Cl$_2$/MeOH 9:1) affording 40 (56 mg, 17%) as yellow-brown solid. $^1$H NMR (300 MHz, DMSO d$_6$): δ 8.78 (m, 2H), 8.12 (bs, 1H), 8.05-7.78 (m, 3H), 7.67 (m, 1H), 4.72 and 4.69 (s, 2H), 4.10 (q, 2H), 3.92 and 3.90 (s, 2H), 1.19 (t, 3H). ESI$^+$MS: calcd for C$_{19}$H$_{16}$N$_6$O$_5$: 408.38; found: 409.1 (MH$^+$).

Synthesis of [2-(3-carbamoyl-2-cyano-indeno[1,2-b]pyrazin-9-ylideneaminooxy)-acetylamino]-acetic acid (41)

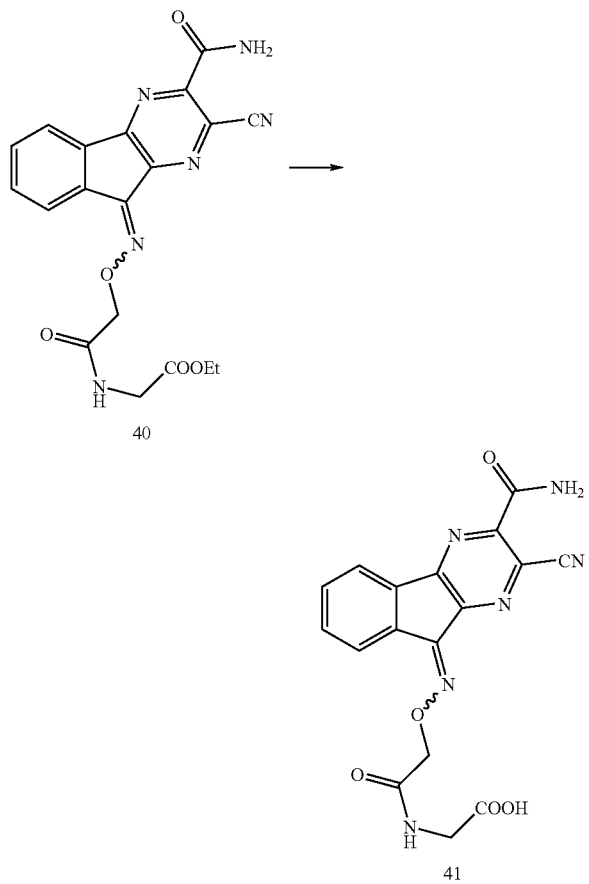

To a solution of 40 (60 mg, 0.15 mmol) in THF/H$_2$O (1:1, 15 ml) LiOH.H$_2$O (30 mg, 0.71 mmol) was added. The mixture was stirred at room temperature and after 2 h 2N HCl was added up to pH=5. The solvent was removed under reduced pressure and a 1:1 mixture of CH$_2$Cl$_2$/MeOH (10 ml) was added. The solution was cooled at 0° C. and the precipitate was collected by filtration, affording 41 (40 mg, 70%) as green solid. $^1$H NMR (300 MHz, DMSO d$_6$+TFA): δ 8.35 (t, 1H), 8.13 (dd, 1H), 7.91 (m, 2H), 7.78 (ddd, 1H), 4.92 (s, 2H), 3.87 (d, 2H). ESI$^+$MS: calcd for C$_{17}$H$_{12}$N$_6$O$_5$: 380.32; found: 381.4 (MH$^+$).

Synthesis of 7-chloro-3-hydroxy-9-oxo-9H-indeno[1,2-b]pyrazine-2-carbonitrile (42)

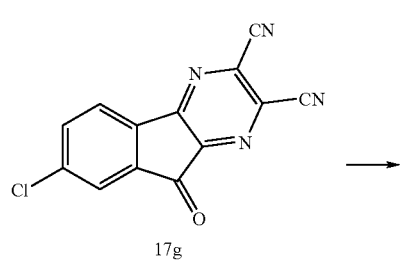

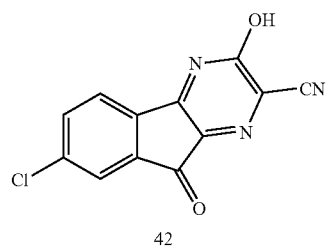

To a suspension of 50 mg (0.19 mmol) 17g and 2.2 mg (5 Mol-%) Na$_2$MoO$_4$ in 2 ml DMSO was added dropwise 82 μl (0.95 mmol) of an aqueous solution of H$_2$O$_2$ (35%). The colour turned to red, and the mixture was stirred for 48 h at room temperature. After addition of 20 mL Dichloromethane, the resulting solution was washed with water and sat. brine (3×5 ml). After drying, filtration and evaporation, the crude product was purified by chromatography (DCM/MeOH 8/2) to yield 35 mg (70%) compound 42 as yellow-orange powder. $^1$H-NMR (d$_6$-DMSO, 300 MHz): δ (ppm)=7.55 (s, 1H); 7.64 (m, 2H). ESI$^-$MS: calcd for C$_{12}$H$_4$ClN$_3$O$_2$: 257.64; found: 255.9 (M-H$^+$).

Synthesis of 9-[(aminocarbonyl)hydrazono]-7-chloro-9H-indeno[1,2-b]pyrazine-2,3-dicarbonitrile (43)

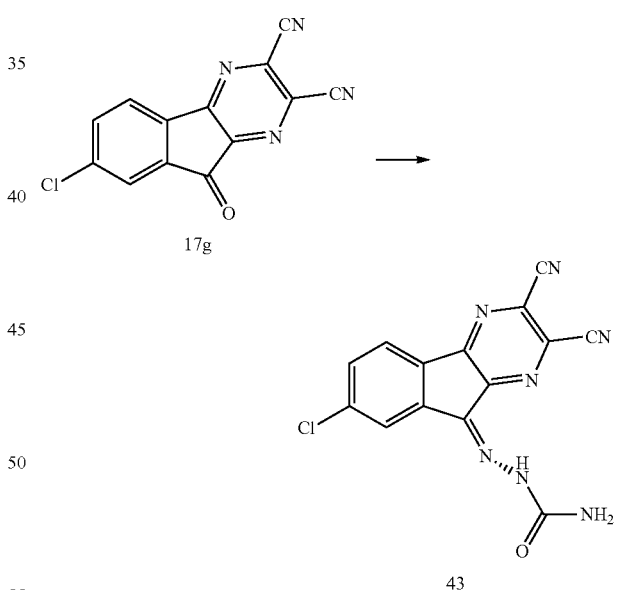

A mixture of 600 mg (2.25 mmol) 17g and 329 mg (2.92 mmol) semicarbazide hydrochloride in 20 ml acetonitrile was heated 14 h under reflux. After that time, TLC indicated complete conversion of the starting product. After evaporation of the solvent, the crude product was recrystallised from aqueous ethanol, and compound 43 was obtained in slightly greenish crystals (90%). $^1$H-NMR (d$_6$-DMSO, 400 MHz): δ (ppm)=7.40 (sl, 1H); 7.70 (sl, 1H); 7.71 (d, J=8 Hz, 1H); 8.17 (d, J=8 Hz, 1H); 8.89 (s, 1H); 10.95 (s, 1H). ESI$^+$MS: calcd for C$_{14}$H$_6$ClN$_7$O: 323.70; found: 324 (MH$^+$).

Representative Cysteine Proteases

USP5 Activity Assay

USP5 was diluted in USP buffer (50 mM Tris HCl; 0.5 mM EDTA; 5 mM DTT; 0.01% Triton X-100; Bovine Serum Albumin 0.05 mg·ml$^{-1}$ pH7.6). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for USP5 was 400 nM Ub-AMC (Boston Biochem). The concentrations of the enzyme (USP5) in specificity assays was 300 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/− standard deviation) were analyzed as % of control (no compound) and plotted as percentage versus the Log of the compound concentration using GraphPad (Prism). Data were fitted to a sigmoidal model (variable slope).

Cloning & Purification of USP7

The cDNA encoding USP7 was obtained by PCR amplification from placenta mRNA. USP7 cDNA was subcloned by PCR into a baculovirus expression vector (pFastBac-HT; Invitrogen). A cDNA encoding a mutated USP7 was generated by mutagenic PCR. The corresponding protein encodes a cysteine to alanine substitution at residue 223. The sequences were ascertained by sequencing of the entire open reading frame. Bacmids encoding USP7 were generated following DH10bac transposition. The corresponding bacmids were transfected into insect cells (Sf9). Viruses were recovered from culture supernatant and amplified twice. Insect cells (Sf9 or High Five; Invitrogen) were infected for 72 hours. Total cell lysates were harvested and lyzed in lysis buffer (Tris HCl 50 mM pH7.6; 0.75% NP40; 500 mM NaCl; 10% glycerol; 1 mM DTT; 10 mM imidazole; Protease Inhibitor Cocktail; AEBSF 20 µg·ml$^{-1}$; Aprotinin 10 µg·ml$^{-1}$). Proteins were affinity purified on metal affinity resins (Talon Metal affinity resin; BD Biosciences). Bound materials were extensively washed in wash buffer (50 mM Sodium Phosphate pH7.0; 300 mM NaCl; 10 mM imidazole; 0.5% Triton X-100; 10% glycerol) and eluted from the resin in 250 mM imidazole-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

USP7 Activity Assay

USP7 was diluted in USP buffer (50 mM Tris HCl; 0.5 mM EDTA; 5 mM DTT; 0.01% Triton X-100; Bovine Serum Albumin 0.05 mg·ml$^{-1}$ pH7.6). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for USP7 was 400 nM Ub-AMC (Chem. Biol., 2003, 10, p. 837-846) (Boston Biochem). The concentrations of the enzyme (USP7) in specificity assays was 152 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/−standard deviation) were analyzed as % of control (no compound) and plotted as percentage versus the Log of the compound concentration using GraphPad (Prism). Data were fitted to a sigmoidal model (variable slope).

Cloning & Purification of USP8

The cDNA encoding USP8 was obtained by PCR amplification from placenta mRNA. USP8 cDNA was subcloned by PCR into a baculovirus expression vector (pFastBac-HT; Invitrogen). A cDNA encoding a mutated USP8 was generated by mutagenic PCR. The corresponding protein encodes a cysteine to alanine substitution at residue 786. The sequences were ascertained by sequencing of the entire open reading frame. Bacmids encoding USP7 were generated following DH10bac transposition. The corresponding bacmids were transfected into insect cells (Sf9). Viruses were recovered from culture supernatant and amplified twice. Insect cells (Sf9 or High Five; Invitrogen) were infected for 72 hours. Total cell lysates were harvested and lyzed in lysis buffer (Tris HCl 50 mM pH7.6; 0.75% NP40; 500 mM NaCl; 10% glycerol; 1 mM DTT; 10 mM imidazole; Protease Inhibitor Cocktail; AEBSF 20 µg·ml$^{-1}$; Aprotinin 10 µg·ml$^{-1}$). Proteins were affinity purified on metal affinity resins (Talon Metal affinity resin; BD Biosciences). Bound materials were extensively washed in wash buffer (50 mM Sodium Phosphate pH 7.0; 300 mM NaCl; 10 mM imidazole; 0.5% Triton X-100; 10% glycerol) and eluted from the resin in 250 mM imidazole-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

USP8 Activity Assay

USP8 was diluted in USP buffer (50 mM Tris HCl; 0.5 mM EDTA; 5 mM DTT; 0.01% Triton X-100; Bovine Serum Albumin 0.05 mg·ml$^{-1}$ pH8.8). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for USP8 was 400 nM Ub-AMC (Boston Biochem). The concentrations of the enzyme (USP8) in specificity assays was 630 µM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/− standard deviation) were analyzed as % of control (no compound) and plotted as percentage versus the Log of the compound concentration using GraphPad (Prism). Data were fitted to a sigmoidal model (variable slope).

UCH-L3 Activity Assay

Uch-L3 was diluted in USP buffer (50 mM Tris HCl; 0.5 mM EDTA; 5 mM DTT; 0.01% Triton X-100; Bovine Serum Albumin 0.05 mg·ml$^{-1}$ pH7.6). Compounds stocks (100 mM) were stored at −20° C. in DMSO. Compounds were tested at the following final concentrations: 100 μM; 33.3 μM; 11.1 μM; 3.7 μM; 1.23 μM; 412 nM; 137 nM; 45.7 nM; 15.2 nM; 5 nM.

Reactions were performed as duplicates in Black LJL 96 well plates (HE microplates; Molecular Devices; 20 μl final reaction volume). The substrate concentration for Uch-L3 was 400 nM Ub-AMC (Boston Biochem). The concentration of the enzyme (Uch-L3) in specificity assays was 13 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). δ Emission 380 nm; δ Excitation=460 nm. Data (mean values+/− standard deviation) were analyzed as % of control (no compound) and plotted as percentage versus the Log of the compound concentration using GraphPad (Prism). Data were fitted to a sigmoidal model (variable slope).

Caspase 3 Activity Assay

Caspase 3 was diluted in Caspase 3 buffer (100 mM Hepes pH 7.5; 10% sucrose; 0.1% CHAPS). Compounds stocks (100 mM) were stored at −20° C. in DMSO. Compounds were tested at the following final concentrations: 100 μM; 33.3 μM; 11.1 μM; 3.7 μM; 1.23 μM; 412 nM; 137 nM; 45.7 nM; 15.2 nM; 5 nM. Reactions were performed as duplicates in Black LJL 96 well plates (HE microplates; Molecular Devices; 20 μl final reaction volume). The substrate concentration for caspase 3 specificity assay was 500 nM (Ac-DEVD-AMC; Promega). The concentration of the enzyme (Caspase 3) in specificity assays was 3.2 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). δ Emission 380 nm; δ Excitation=460 nm. Data (mean values+/− standard deviation) were analyzed as % of control (no compound) and plotted as percentage versus the Log of the compound concentration using GraphPad (Prism). Data were fitted to a sigmoidal model (variable slope).

Cathepsin B Activity Assay

Cathepsin B was diluted in Cathepsin B buffer (20 mM Tris HCl pH 6.8; 1 mM EDTA; 1 mM DTT). Compounds stocks (100 mM) were stored at −20° C. in DMSO. Compounds were tested at the following final concentrations: 100 μM; 33.3 μM; 11.1 μM; 3.7 μM; 1.23 μM; 412 nM; 137 nM; 45.7 nM; 15.2 nM; 5 nM. Reactions were performed as duplicates in Black LJL 96 well plates (HE microplates; Molecular Devices; 20 μl final reaction volume). The substrate concentration for cathepsin B specificity assay was 36 μM (z-RR-AMC; Calbiochem). The concentration of the enzyme (Cathepsin B) in specificity assays was 3.6 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). δ Emission 380 nm; 6 Excitation=460 nm. Data (mean values+/− standard deviation) were analyzed as % of control (no compound) and plotted as percentage versus the Log of the compound concentration using GraphPad (Prism). Data were fitted to a sigmoidal model (variable slope).

Cell Viability and Proliferation Methods

HCT116 Cell Viability and Proliferation Assay

HCT116 colon cancer cells were obtained from ATCC (American Type Culture Collection), and maintained in Mc Coy's 5A medium containing 10% FBS, 3 mM glutamine and 1% penicillin/streptomycin. Cells were incubated at 37° C. in a humidified atmosphere containing 5% $CO_2$.

Cell viability was assayed using the MTS technique in 96-well culture plates (CellTiter 96® Aqueous Non-Radioactive Cell Proliferation Assay, Promega) according to the manufacturer's instructions. MTS (3-(4,5-dimethylthiazol-2-yl)-5-(3-carboxymethoxyphenyl)-2-(4-sulfophenyl)-2H-tetrazolium) is a MTT-derived tetrazolium that is reduced in metabolically active cells into a soluble, cell-permeant formazan. The amount of formazan, detected by its absorbance at 492 nm is proportional to the number of living, metabolically active cells.

$10^3$ HCT116 cells were seeded per well. 24 hours later, the medium was changed and the cells treated in triplicate with the following concentrations of each compound: 10 μM-3.33 μM-1.11 μM-370 nM-123 nM-41 nM-14 nM and 5 nM. The compounds were diluted in 100% DMSO, whose final concentration on cells was kept at 0.5%.

Cells were incubated with the compounds for 72 hours, and their viability then assayed by the addition of MTS for 2 hours. Absorbance at 492 nm was measured directly from the 96-well culture plates. GI50 (Growth Inhibition 50) concentrations for each compound were calculated using a sigmoidal variable slope fit (Prism 4.0, Graphpad Softwares). Values represent mean of 3 independent experiments.

PC3 Cell Viability and Proliferation Assay

PC-3 prostate cancer cells were obtained from ATCC, and maintained in F-12K medium containing 7% FBS and 1% penicillin/streptomycin. Cells were incubated at 37° C. in a humidified atmosphere containing 5% $CO_2$.

Cell viability was assayed using the MTS technique in 96-well culture plates (CellTiter 96® Aqueous Non-Radioactive Cell Proliferation Assay, Promega) according to the manufacturer's instructions. MTS (3-(4,5-dimethyl-thiazol-2-yl)-5-(3-carboxymethoxyphenyl)-2-(4-sulfophenyl)-2H-tetrazolium) is a MTT-derived tetrazolium that is reduced in metabolically active cells into a soluble, cell-permeant formazan. The amount of formazan, detected by its absorbance at 492 nm is proportional to the number of living, metabolically active cells.

$2 \times 10^3$ PC3 cells were seeded per well. 24 hours later, the medium was changed and the cells treated in triplicate with the following concentrations of each compound: 10 μM-3.33 μM-1.11 μM-370 nM-123 nM-41 nM-14 nM and 5 nM. The compounds were diluted in 100% DMSO, whose final concentration on cells was kept at 0.5%.

Cells were incubated with the compounds for 72 hours, and their viability then assayed by the addition of MTS for 2 hours. Absorbance at 492 nm was measured directly from the 96-well culture plates. GI50 (Growth Inhibition 50) concentrations for each compound were calculated using a sigmoidal variable slope fit (Prism 4.0, Graphpad Softwares). Values represent mean of 3 independent experiments.

Results
1. Inhibition of Cysteine Protease Activities

| *USPS | |
|---|---|
| Experimental N° | USP 5 |
| Example 1 | 1.3 μM |
| Example 2 | AF |
| Example 3 | >100 μM |
| Example 4 | >100 μM |
| Example 5 | >100 μM |
| Example 6 | 9.1 μM |
| Example 7 | >100 μM |
| Example 8 | >100 μM |
| Example 9 | >100 μM |
| Example 10 | >100 μM |
| Example 11 | 2.1 μM |
| Example 12 | 45 μM |
| Example 13a | 19.5 μM |
| Example 13b | >100 μM |
| Example 13C | >100 μM |
| Example 13d | >100 μM |
| Example 13e | 32 μM |
| Example 14 | 1.9 μM |
| Example 16b | >100 μM |
| Example 16c | >100 μM |
| Example 17a | 29 μM |
| Example 17b | >100 μM |
| Example 17c | 60 μM |
| Example 17d | 2.5 μM |
| Example 17e | 7.8 μM |
| Example 17f | 3.3 μM |
| Example 17g | 0.16 μM |
| Example 17h | 1.0 μM |
| Example 17i | 23 μM |
| Example 17j | >100 μM |
| Example 19 | >100 μM |
| Example 20 | >100 μM |
| Example 21 | >100 μM |
| Example 22 | >100 μM |
| Example 23 | >100 μM |
| Example 26 | 60 μM |
| Example 27a | >100 μM |
| Example 27b | >100 μM |
| Example 27c | 1.7 μM |
| Example 30 | 1.61 μM |
| Example 31 | 0.329 μM |
| Example 32 | 1.67 μM |
| Example 33 | 2.1 μM |
| Example 34a | 0.143 μM |
| Example 34b | 0.523 μM |
| Example 34c | 0.606 μM |
| Example 34d | 0.113 μM |
| Example 35 | 0.161 μM |
| Example 36 | 0.208 μM |
| Example 37 | 0.799 μM |
| Example 38 | 1.849 μM |
| Example 40 | 1.133 μM |
| Example 41 | 1.887 μM |
| Example 42 | >100 μM |
| Example 43 | >100 μM |

AF: Autofluorescent

| *USPS | |
|---|---|
| Experimental N° | USP 7 |
| Example 1 | 3.5 μM |
| Example 2 | AF |
| Example 3 | >100 μM |
| Example 4 | >100 μM |
| Example 5 | >100 μM |
| Example 6 | 21.8 μM |
| Example 7 | >100 μM |
| Example 8 | >100 μM |
| Example 9 | >100 μM |
| Example 10 | >100 μM |
| Example 11 | 13 μM |
| Example 12 | >100 μM |
| Example 13a | >100 μM |
| Example 13b | >100 μM |
| Example 13C | >100 μM |
| Example 13d | >100 μM |
| Example 13e | >100 μM |
| Example 14 | 4.1 μM |
| Example 16b | >100 μM |
| Example 16c | >100 μM |
| Example 17a | >100 μM |
| Example 17b | 10.2 μM |
| Example 17c | >100 μM |
| Example 17d | 18 μM |
| Example 17e | 7.2 μM |
| Example 17f | 12.7 μM |
| Example 17g | 0.53 μM |
| Example 17h | 4.3 μM |
| Example 17i | >100 μM |
| Example 17j | 66 μM |
| Example 19 | >100 μM |
| Example 20 | >100 μM |
| Example 21 | >100 μM |
| Example 22 | >100 μM |
| Example 23 | >100 μM |
| Example 26 | >100 μM |
| Example 27a | >100 μM |
| Example 27b | >100 μM |
| Example 27c | 3.5 μM |
| Example 30 | 2.22 μM |
| Example 31 | 0.591 μM |
| Example 32 | 2.59 μM |
| Example 33 | 13 μM |
| Example 34a | 0.50 μM |
| Example 34b | 2.51 μM |
| Example 34c | 2.88 μM |
| Example 34d | 0.396 μM |
| Example 35 | 0.506 μM |
| Example 36 | 1.266 μM |
| Example 37 | 2.328 μM |
| Example 38 | 4.025 μM |
| Example 40 | 2.797 μM |
| Example 41 | 4.281 μM |

-continued

| Experimental N° | USP 7 |
|---|---|
| Example 42 | >100 μM |
| Example 43 | >100 μM |

| Experimental N° | USP 8 |
|---|---|
| Example 1 | 0.29 μM |
| Example 2 | AF |
| Example 3 | 31 μM |
| Example 4 | >100 μM |
| Example 5 | 53 μM |
| Example 6 | 8.4 μM |
| Example 7 | 48 μM |
| Example 8 | >100 μM |
| Example 9 | 16.2 μM |
| Example 10 | 13 μM |
| Example 11 | 0.73 μM |
| Example 12 | 7.0 μM |
| Example 13a | 0.98 μM |
| Example 13b | 0.56 μM |
| Example 13C | 0.85 μM |
| Example 13d | 0.28 μM |
| Example 13e | 0.24 μM |
| Example 14 | 0.35 μM |
| Example 16b | 72 μM |
| Example 16c | >100 μM |
| Example 17a | 4.0 μM |
| Example 17b | 2.5 μM |
| Example 17c | 3.1 μM |
| Example 17d | 0.71 μM |
| Example 17e | 0.93 μM |
| Example 17f | 0.81 μM |
| Example 17g | 0.096 μM |
| Example 17h | 0.25 μM |
| Example 17i | 2.1 μM |
| Example 17j | >100 μM |
| Example 19 | >100 μM |
| Example 20 | >100 μM |
| Example 21 | >100 μM |
| Example 22 | >100 μM |
| Example 23 | 46 μM |
| Example 26 | 11 μM |
| Example 27a | 2.3 μM |
| Example 27b | 11.3 μM |
| Example 27c | 0.201 μM |
| Example 30 | 0.316 μM |
| Example 31 | 0.076 μM |
| Example 32 | 0.111 μM |
| Example 33 | 0.733 μM |
| Example 34a | 0.058 μM |
| Example 34b | 0.063 μM |
| Example 34c | 0.071 μM |
| Example 34d | 0.029 μM |
| Example 35 | 0.027 μM |
| Example 36 | 0.205 μM |
| Example 37 | 0.200 μM |
| Example 38 | 0.272 μM |
| Example 40 | 0.155 μM |
| Example 41 | 0.118 μM |
| Example 42 | >100 μM |
| Example 43 | 0.814 μM |

AF: Autofluorescent

| UCH-L3 | |
|---|---|
| Experimental N° | Uch-L3 |
| Example 1 | 0.76 μM |
| Example 2 | AF |
| Example 3 | 13 μM |

-continued

| UCH-L3 | |
|---|---|
| Experimental N° | Uch-L3 |
| Example 4 | >100 μM |
| Example 5 | 24 μM |
| Example 6 | 1.1 μM |
| Example 7 | 52 μM |
| Example 8 | >100 μM |
| Example 9 | 8.8 μM |
| Example 10 | 20 μM |
| Example 11 | 0.60 μM |
| Example 12 | 1.3 μM |
| Example 13a | 2.2 μM |
| Example 13b | 10 μM |
| Example 13C | >100 μM |
| Example 13d | 1.3 μM |
| Example 13e | 0.54 μM |
| Example 14 | 0.39 μM |
| Example 16b | 49 μM |
| Example 16c | >100 μM |
| Example 17a | 7.0 μM |
| Example 17b | 5.4 μM |
| Example 17c | 2.0 μM |
| Example 17d | 0.77 μM |
| Example 17e | 2.1 μM |
| Example 17f | 0.60 μM |
| Example 17g | 0.070 μM |
| Example 17h | 0.33 μM |
| Example 17i | 3.1 μM |
| Example 17j | 8 μM |
| Example 19 | >100 μM |
| Example 20 | 39.6 μM |
| Example 21 | >100 μM |
| Example 22 | 22 μM |
| Example 23 | 86 μM |
| Example 26 | 1.6 μM |
| Example 27a | 10.5 μM |
| Example 27b | 1.7 μM |
| Example 27c | 0.502 μM |
| Example 30 | 0.339 μM |
| Example 31 | 0.104 μM |
| Example 32 | 0.258 μM |
| Example 33 | 0.596 μM |
| Example 34a | 0.032 μM |
| Example 34b | 0.099 μM |
| Example 34c | 0.109 μM |
| Example 34d | 0.037 μM |
| Example 35 | 0.048 μM |
| Example 36 | 0.178 μM |
| Example 37 | 0.393 μM |
| Example 38 | 0.758 μM |
| Example 40 | 0.245 μM |
| Example 41 | 0.328 μM |
| Example 42 | >100 μM |
| Example 43 | 13.5 μM |

AF: Autofluorescent

| Caspase 3 | |
|---|---|
| Experimental N° | Casp3 |
| Example 1 | 0.69 μM |
| Example 2 | AF |
| Example 3 | >100 μM |
| Example 4 | >100 μM |
| Example 5 | >100 μM |
| Example 6 | 9.3 μM |
| Example 7 | >100 μM |
| Example 8 | >100 μM |
| Example 9 | >100 μM |
| Example 10 | >100 μM |
| Example 11 | 2.3 μM |
| Example 12 | 5.6 μM |
| Example 13a | 52 μM |

-continued

Caspase 3

| Experimental N° | Casp3 |
|---|---|
| Example 13b | >100 μM |
| Example 13C | >100 μM |
| Example 13d | >100 μM |
| Example 13e | >100 μM |
| Example 14 | 1.3 μM |
| Example 16b | >100 μM |
| Example 16c | >100 μM |
| Example 17a | 10 μM |
| Example 17b | 51 μM |
| Example 17c | 13 μM |
| Example 17d | 1.8 μM |
| Example 17e | 3.3 μM |
| Example 17f | 2.0 μM |
| Example 17g | 0.29 μM |
| Example 17h | 1.0 μM |
| Example 17i | 2.0 μM |
| Example 17j | 47 μM |
| Example 19 | >100 μM |
| Example 20 | >100 μM |
| Example 21 | >100 μM |
| Example 22 | >100 μM |
| Example 23 | >100 μM |
| Example 26 | 100 μM |
| Example 27a | >100 μM |
| Example 27b | >100 μM |
| Example 27c | 2.83 μM |
| Example 30 | 1.07 μM |
| Example 31 | 0.158 μM |
| Example 32 | 3.6 μM |
| Example 33 | 2.3 μM |
| Example 34a | 0.245 μM |
| Example 34b | 0.624 μM |
| Example 34c | 1.22 μM |
| Example 34d | 0.131 μM |
| Example 35 | 0.120 μM |
| Example 36 | 0.402 μM |
| Example 37 | 1.16 μM |
| Example 38 | 3.938 μM |
| Example 40 | 0.857 μM |
| Example 41 | 1.983 μM |
| Example 42 | >100 μM |
| Example 43 | 64.9 μM |

AF: Autofluorescent

Cathepsine B

| Experimental N° | cathepB |
|---|---|
| Example 1 | 12 μM |
| Example 2 | AF |
| Example 3 | >100 μM |
| Example 4 | >100 μM |
| Example 5 | >100 μM |
| Example 6 | >100 μM |
| Example 7 | >100 μM |
| Example 8 | >100 μM |
| Example 9 | >100 μM |
| Example 10 | >100 μM |
| Example 11 | 11.1 μM |
| Example 12 | 21 μM |
| Example 13a | >100 μM |
| Example 13b | >100 μM |
| Example 13C | >100 μM |
| Example 13d | >100 μM |
| Example 13e | >100 μM |
| Example 14 | 74 μM |
| Example 16b | >100 μM |
| Example 16c | >100 μM |
| Example 17b | >100 μM |
| Example 17c | >100 μM |
| Example 17d | 87 μM |

-continued

Cathepsine B

| Experimental N° | cathepB |
|---|---|
| Example 17e | 20 μM |
| Example 17f | 52.6 μM |
| Example 17g | 1.5 μM |
| Example 17h | 6.0 μM |
| Example 17i | 32 μM |
| Example 17j | 40 μM |
| Example 19 | >100 μM |
| Example 20 | >100 μM |
| Example 21 | >100 μM |
| Example 22 | >100 μM |
| Example 23 | >100 μM |
| Example 26 | >100 μM |
| Example 27a | >100 μM |
| Example 27b | >100 μM |
| Example 32 | 69 μM |
| Example 33 | 1.11 μM |
| Example 34a | 3.5 μM |
| Example 34b | >100 μM |
| Example 34c | >100 μM |
| Example 34d | 1.11 μM |
| Example 35 | 11.5 μM |
| Example 42 | >100 μM |
| Example 43 | >100 μM |

AF: Autofluorescent

2. Inhibition of Cell Viability and Proliferation

| Experimental N° | HCT116 D3 GI50 |
|---|---|
| Example 1 | 0.15 μM |
| Example 2 | >10 μM |
| Example 3 | >10 μM |
| Example 4 | >10 μM |
| Example 5 | >10 μM |
| Example 6 | >10 μM |
| Example 7 | >10 μM |
| Example 8 | >10 μM |
| Example 9 | >10 μM |
| Example 10 | 3.4 μM |
| Example 11 | 1.60 μM |
| Example 12 | 6.5 μM |
| Example 13a | 0.39 μM |
| Example 13b | 0.58 μM |
| Example 13c | 0.75 μM |
| Example 13d | 1.18 μM |
| Example 13e | 0.54 μM |
| Example 14 | 0.43 μM |
| Example 16b | 2.85 μM |
| Example 16c | 1.47 μM |
| Example 17a | 0.61 μM |
| Example 17b | 0.53 μM |
| Example 17c | 0.39 μM |
| Example 17d | 0.68 μM |
| Example 17e | 0.30 μM |
| Example 17f | 0.93 μM |
| Example 17g | 0.32 μM |
| Example 17h | 0.16 μM |
| Example 17i | 0.56 μM |
| Example 17j | >10 μM |
| Example 19 | 10 μM |
| Example 20 | 0.78 μM |
| Example 21 | >10 μM |
| Example 22 | >10 μM |
| Example 23 | >10 μM |
| Example 24a | 0.50 μM |
| Example 24b | 0.94 μM |
| Example 25 | 0.19 μM |
| Example 26 | >10 μM |
| Example 27a | 0.549 μM |
| Example 27b | 0.294 μM |
| Example 27c | 0.421 μM |

| Experimental N° | HCT116 D3 GI50 |
|---|---|
| Example 30 | 0.705 μM |
| Example 31 | 0.753 μM |
| Example 32 | 0.385 μM |
| Example 33 | 1.6 μM |
| Example 34a | 0.496 μM |
| Example 34b | 0.469 μM |
| Example 34c | 0.378 μM |
| Example 34d | 0.916 μM |
| Example 35 | 1.35 μM |
| Example 36 | 4.25 μM |
| Example 37 | 0.652 μM |
| Example 38 | >10 μM |
| Example 40 | 4.60 μM |
| Example 41 | >10 μM |
| Example 42 | >10 μM |
| Example 43 | 0.512 μM |

| Experimental N° | PC3 D3 GI50 |
|---|---|
| Example 1 | 0.61 μM |
| Example 2 | >10 μM |
| Example 3 | >10 μM |
| Example 4 | >10 μM |
| Example 5 | >10 μM |
| Example 6 | >10 μM |
| Example 7 | >10 μM |
| Example 8 | >10 μM |
| Example 9 | >10 μM |
| Example 10 | 4.4 μM |
| Example 11 | 1.24 μM |
| Example 12 | 4.4 μM |
| Example 13a | 0.43 μM |
| Example 13b | 0.54 μM |
| Example 13C | 0.70 μM |
| Example 13d | 1.54 μM |
| Example 13e | 0.53 μM |
| Example 14 | 0.51 μM |
| Example 16b | 2.78 μM |
| Example 16c | 3.37 μM |
| Example 17a | 1.40 μM |
| Example 17b | 0.92 μM |
| Example 17c | 0.93 μM |
| Example 17d | 0.91 μM |
| Example 17e | 1.32 μM |
| Example 17f | 0.80 μM |
| Example 17g | 1.11 μM |
| Example 17h | 0.57 μM |
| Example 17i | 1.27 μM |
| Example 17j | >10 μM |
| Example 19 | 4.2 μM |
| Example 20 | 1.26 μM |
| Example 21 | >10 μM |
| Example 22 | >10 μM |
| Example 23 | >10 μM |
| Example 24a | 0.39 μM |
| Example 24b | 0.62 μM |
| Example 25 | 1.4 μM |
| Example 26 | >10 μM |
| Example 27a | 1.003 μM |
| Example 27b | 0.259 μM |
| Example 27c | 0.803 μM |
| Example 30 | 0.854 μM |
| Example 31 | 2.43 μM |
| Example 32 | 1.426 μM |
| Example 33 | 1.2 μM |
| Example 34a | 0.511 μM |
| Example 34b | 0.479 μM |
| Example 34c | 0.362 μM |
| Example 34d | 1.20 μM |
| Example 35 | 1.28 μM |
| Example 42 | >10 μM |
| Example 43 | 0.655 μM |

The invention claimed is:

1. A compound of formula (I):

$$(I)$$

wherein:
m is 0, 1 or 2, wherein when m=0, —(X(R$_2$)$_{m'}$)$_m$— is none so as to form a single bond;
n is 0, 1 or 2, wherein when n=0, —(Y(R$_7$)$_{n'}$)$_n$— is none so as to form a single bond;
m' and n' are independently 1 or 2;
X is a carbon atom;
Y is a carbon atom;
wherein m+n=1;
=== is either a single or double bond, as appropriate;
— is either none or a single bond, as appropriate;
R1 is chosen from the group consisting of H, CN, Hal, OAlk, OH, NRCN, C(CN)=C(OH)(OAlk), SR, NRR', (Alk)$_p$-C(O)NRR', Heterocycle, Aryl, Heteroaryl, where Alk, Aryl, Heteroaryl, heterocycle are optionally substituted by Hal, NRR', CN, OH, CF$_3$, Aryl, Heteroaryl, OAlk,
where p is 0 or 1;
R3, R4, R5, R6 are each identical or different and are independently chosen from the group consisting of H, OAlk, Alk, Hal, NRR', CN, OH, CF$_3$, Aryl, Heteroaryl;
R$_2$ is chosen from the group consisting of H, O, OH, N—OH, N—OAlk, N—O-Aryl, N—O-Alk-Aryl, N—NR—CONRR', N—O—CO-Alk, or 2 R$_2$ bound at the same X form together with that X an heterocycle; wherein said Alk, Aryl or heterocycle are optionally substituted by OAlk, Alk, Hal, NRR', CN, OH, CF$_3$, OAryl, —CO—(NR-Alk-CO)$_{p'}$—OAlk, —CO(NR-Alk-CO)$_{p'}$—OH,
where p' is 0 or 1;
R$_7$ is chosen from the group consisting of H, O, OH, N—OH, N—OAlk, N—O-Aryl, N—O-Alk-Aryl, N—NR—CONRR', N—O—CO-Alk, or 2 R$_7$ bound at the same Y form together with that Y an heterocycle; wherein said Alk, Aryl or heterocycle are optionally substituted by OAlk, Alk, Hal, NRR', CN, OH, CF$_3$, OAryl, —CO—(NR-Alk-CO)$_{p'}$—OAlk, —CO(NR-Alk-CO)$_{p'}$—OH,
where p' is 0 or 1;
R and R' are each identical or different and are independently chosen from the group consisting of H, Alk, wherein Alk is optionally substituted by Hal, NRR', CN, OH, CF$_3$, Aryl, Heteroaryl;

wherein:
the aryl is an aromatic monocyclic or multicyclic hydrocarbon ring system of 6 to 14 carbon atoms,
the heteroaryl is a 5 to 10 membered aromatic monocyclic or bicyclic, wherein the ring comprises from one to three heteroatoms individually selected from the group consisting of nitrogen, oxygen and sulphur; and
the heterocycle is a saturated, partially unsaturated, non-aromatic stable 5 to 10 membered monocyclic or bicyclic ring, wherein the ring comprises from one to three heteroatoms individually selected from the group consisting of oxygen, nitrogen, sulphur, phosphorus and selenium,
or a pharmaceutically acceptable salt thereof
with the exception of compounds where:
R3, R4, R5, R6=H, R1=CN, —($X(R_2)_{m'})_m$— represents a single bond, and —($Y(R_7)_{n'})_n$— represents —C(=O)—, or —$CH_2$—
R3, R5, R6=H, R4=OMe, R1=CN, —($X(R_2)_{m'})_m$— represents a single bond, and —($Y(R_7)_{n'})_n$— represents —C(=O)—, or
R3, R4, R6=H, R5=OMe, R1=CN, —($X(R_2)_{m'})_m$— represents a single bond, and —($Y(R_7)_{n'})_n$— represents —C(=O)—, or
R3, R4, R5, R6=H, R1=$NH_2$, —($X(R_2)_{m'})_m$— represents a single bond, and —($Y(R_7)_{n'})_n$— represents —$CH_2$— or —$CH_2$—$CH_2$—; or,
R3, R4, R5, R6=H, R1=$NH_2$, —($X(R_2)_{m'})_m$— represents —$CH_2$— or —$CH_2$—$CH_2$— and —($Y(R_7)_{n'})_n$— represents a single bond.

2. Compound according to claim 1 with the further exception of the following compound: R3, R4, R5, R6=H, R1=CN, —($X(R_2)_{m'})_m$— represents a single bond, and —($Y(R_7)_{n'})_n$— represents —C(=N—OH)—.

3. Compound according to claim 1, wherein:
R1 is chosen from the group consisting of H, CN, Hal, OAlk, OH, NRCN, C(CN)=C(OH)(OAlk), NRR', $(Alk)_p$-C(O)NRR', Heterocycle, where Alk is optionally substituted by OAlk and where Heterocycle is optionally substituted by Hal where p is 0 or 1;
R3, R4, R5, R6 are each identical or different and are independently chosen from the group consisting of H, OAlk, Alk, Hal;
—($Y(R_7)_{n'})_n$— is a single bond or Y represents a carbon atom;
$R_2$ is chosen from the group consisting of H, O;
$R_7$ is chosen from the group consisting of H, O, OH, N—OH, N-OAlk, N—O-Aryl, N—O-Alk-Aryl, N—O-AlkOAryl, N—O-Alk-CO(NR-Alk-CO)p'-OAlk, N—O-Alk-CO(NR-Alk-CO)p'-OH, —N—NR—CONRR', N—CO-Alk, or 2 $R_7$ bound at the same Y form together with that Y an heterocycle
where p' is 0 or 1;
R and R' are each identical or different and are independently chosen from the group consisting of H, Alk.

4. Compound according to claim 1, wherein —($X(R_2)_{m'})_m$— represents a single bond, n is 1, n' is 1, Y is a carbon atom.

5. Compound according to claim 1, wherein R1 is chosen from the group consisting of H, CN, Hal, OAlk, OH, NRCN, C(CN)=C(OH)(OAlk), SR, NRR', C(O)NRR', Heterocycle, where Alk is optionally substituted by OAlk and where Heterocycle is optionally substituted by Hal.

6. Compound according to claim 1, wherein R3, R4, R5, R6 are each identical or different and are independently chosen from the group consisting of H, OAlk, Alk, Hal.

7. Compound according to claim 1, wherein $R_7$ is chosen from the group consisting of O, N—OH, N-OAlk, N—O-Aryl, N—O-Alk-Aryl.

8. Compound according to claim 1, wherein R and R' are each identical or different and are independently chosen from the group consisting of H, Alk.

9. Compound according to claim 1 selected from the group consisting of:
9-hydroxy-3-methoxy-9H-indeno[1,2-b]pyrazine-2-carbonitrile
3-methoxy-9-oxo-9H-indeno[1,2-b]pyrazine-2-carbonitrile
3-dimethylamino-9-oxo-9H-indeno[1,2-b]pyrazine-2-carbonitrile
3-(2-methoxy-ethoxy)-9-oxo-9H-indeno[1,2-b]pyrazine-2-carbonitrile
3-hydroxy-9-oxo-9H-indeno[1,2-b]pyrazine-2-carbonitrile
3-amino-9-oxo-9H-indeno[1,2-b]pyrazine-2-carbonitrile
3-(4,4-difluoro-piperidin-1-yl)-9-oxo-9H-indeno[1,2-b]pyrazine-2-carbonitrile
3-chloro-9-oxo-9H-indeno[1,2-b]pyrazine-2-carbonitrile
9-(1',3'-dioxolan-2'-yl)-9H-indeno[1,2-b]pyrazine-2,3-dicarbonitrile
2-cyano-9-[hydroxyimino]-9H-indeno[1,2-b]pyrazine-3-carboxylic acid amide
9-(methoxyimino)-9H-indeno[1,2-b]pyrazine-2,3-dicarbonitrile
9-(Allyloxyimino)-9H-indeno[1,2-b]pyrazine-2,3-dicarbonitrile
9-Benzyloxyimino-9H-indeno[1,2-b]pyrazine-2,3-dicarbonitrile
9-Ethoxyimino-9H-indeno[1,2-b]pyrazine-2,3-dicarbonitrile
9-Phenoxyimino-9H-indeno[1,2-b]pyrazine-2,3-dicarbonitrile
6-Methoxy-9H-indeno[1,2-b]pyrazine-2,3-dicarbonitrile
6,7-Dimethoxy-9H-indeno[1,2-b]pyrazine-2,3-dicarbonitrile
8-Methyl-9H-indeno[1,2-b]pyrazine-2,3-dicarbonitrile
7,8-Dimethoxy-9H-indeno[1,2-b]pyrazine-2,3-dicarbonitrile
6-Methyl-9H-indeno[1,2-b]pyrazine-2,3-dicarbonitrile
5,8-Dimethoxy-9H-indeno[1,2-b]pyrazine-2,3-dicarbonitrile
6-Methoxy-9-oxo-9H-indeno[1,2-b]pyrazine-2,3-dicarbonitrile
6,7-Dimethoxy-9-oxo-9H-indeno[1,2-b]pyrazine-2,3-dicarbonitrile
8-Methyl-9-oxo-9H-indeno[1,2-b]pyrazine-2,3-dicarbonitrile
7,8-Dimethoxy-9-oxo-9H-indeno[1,2-b]pyrazine-2,3-dicarbonitrile
6-Methyl-9-oxo-9H-indeno[1,2-b]pyrazine-2,3-dicarbonitrile
5,8-Dimethoxy-9-oxo-9H-indeno[1,2-b]pyrazine-2,3-dicarbonitrile
7-Chloro-9-oxo-9H-indeno[1,2-b]pyrazine-2,3-dicarbonitrile
7-Fluoro-9-oxo-9H-indeno[1,2-b]pyrazine-2,3-dicarbonitrile
7-Hydroxy-9-oxo-9H-indeno[1,2-b]pyrazine-2,3-dicarbonitrile
9-[hydroxyimino]-9H-indeno[1,2-b]pyrazine-2,3-dicarbonitrile
2-cyano-9-oxo-9H-indeno[1,2-b]pyrazin-3-yl-cyanamide 3-(1-cyano-2-ethoxy-2-hydroxy-vinyl)-9-oxo-9H-indeno[1,2-b]pyrazine-2-carbonitrile
3-ethylsulfanyl-9-oxo-9H-indeno[1,2-b]pyrazine-2-carbonitrile
7-Chloro-9-methoxyimino-9H-indeno[1,2-b]pyrazine-2,3-dicarbonitrile
9-Allyloxyimino-7-chloro-9H-indeno[1,2-b]pyrazine-2,3-dicarbonitrile
6-Chloro-9-oxo-9H-indeno[1,2-b]pyrazine-2,3-dicarbonitrile
2-(2-cyano-9-oxo-9H-indeno[1,2-b]pyrazin-3-yl)-acetamide
9-(2-Phenoxy-ethoxyimino)-9H-indeno[1,2-b]pyrazine-2,3-dicarbonitrile
7-Chloro-9-(2-phenoxy-ethoxyimino)-9H-indeno[1,2-b]pyrazine-2,3-dicarbonitrile
9-Allyloxyimino-6-chloro-9H-indeno[1,2-b]pyrazine-2,3-dicarbonitrile
7-Fluoro-8-methyl-9-oxo-9H-indeno[1,2-b]pyrazine-2,3-dicarbonitrile
6,7-dichloro-9-oxo-9H-indeno[1,2-b]pyrazine-2,3-dicarbonitrile
6-ethyl-9-oxo-9H-indeno[1,2-b]pyrazine-2,3-dicarbonitrile
2-cyano-9-[hydroxyimino]-9H-indeno[1,2-b]pyrazine-3-carboxylic acid amide
9-Allyloxyimino-2-cyano-9H-indeno[1,2-b]pyrazine-3-carboxylic acid amide2-Cyano-9-ethoxyimino-9H-indeno[1,2-b]pyrazine-3-carboxylic acid amide
2-Cyano-9-(2-methoxy-ethoxyimino)-9H-indeno[1,2-b]pyrazine-3-carboxylic acid amide
2-Cyano-9-methoxyimino-9H-indeno[1,2-b]pyrazine-3-carboxylic acid amide
2-cyano-9-acetoxyimino-9H-indeno[1,2-b]pyrazine-3-carboxylic acid amide
2-cyano-9-oxo-9H-indeno[1,2-b]pyrazine-3-carboxylic acid amide
(3-carbamoyl-2-cyano-indeno[1,2-b]pyrazin-9-ylideneaminooxy)-acetic acid ethyl ester
(3-carbamoyl-2-cyano-indeno[1,2-b]pyrazin-9-ylideneaminooxy)-acetic acid
[2-(3-carbamoyl-2-cyano-indeno[1,2-b]pyrazin-9-ylideneaminooxy)-acetylamino]-acetic acid ethyl ester
[2-(3-carbamoyl-2-cyano-indeno[1,2-b]pyrazin-9-ylideneaminooxy)-acetylamino]-acetic acid
7-chloro-3-hydroxy-9-oxo-9H-indeno[1,2-b]pyrazine-2-carbonitrile
9-[(aminocarbonyl)hydrazono]-7-chloro-9H-indeno[1,2-b]pyrazine-2,3-dicarbonitrile
or a pharmaceutically acceptable salt thereof.

10. Compound according to claim 1 selected from the group consisting of:
9-hydroxy-3-methoxy-9H-indeno[1,2-b]pyrazine-2-carbonitrile
3-methoxy-9-oxo-9H-indeno[1,2-b]pyrazine-2-carbonitrile
3-dimethylamino-9-oxo-9H-indeno[1,2-b]pyrazine-2-carbonitrile
3-(2-methoxy-ethoxy)-9-oxo-9H-indeno[1,2-b]pyrazine-2-carbonitrile
3-hydroxy-9-oxo-9H-indeno[1,2-b]pyrazine-2-carbonitrile
3-amino-9-oxo-9H-indeno[1,2-b]pyrazine-2-carbonitrile
3-(4,4-difluoro-piperidin-1-yl)-9-oxo-9H-indeno[1,2-b]pyrazine-2-carbonitrile
3-chloro-9-oxo-9H-indeno[1,2-b]pyrazine-2-carbonitrile
9-(1',3'-dioxolan-2'-yl)-9H-indeno[1,2-b]pyrazine-2,3-dicarbonitrile
2-cyano-9-[hydroxyimino]-9H-indeno[1,2-b]pyrazine-3-carboxylic acid amide
9-(methoxyimino)-9H-indeno[1,2-b]pyrazine-2,3-dicarbonitrile
9-(Allyloxyimino)-9H-indeno[1,2-b]pyrazine-2,3-dicarbonitrile
9-Benzyloxyimino-9H-indeno[1,2-b]pyrazine-2,3-dicarbonitrile
9-Ethoxyimino-9H-indeno[1,2-b]pyrazine-2,3-dicarbonitrile
9-Phenoxyimino-9H-indeno[1,2-b]pyrazine-2,3-dicarbonitrile
6-Methoxy-9H-indeno[1,2-b]pyrazine-2,3-dicarbonitrile
6,7-Dimethoxy-9H-indeno[1,2-b]pyrazine-2,3-dicarbonitrile
8-Methyl-9H-indeno[1,2-b]pyrazine-2,3-dicarbonitrile
7,8-Dimethoxy-9H-indeno[1,2-b]pyrazine-2,3-dicarbonitrile
6-Methyl-9H-indeno[1,2-b]pyrazine-2,3-dicarbonitrile
5,8-Dimethoxy-9H-indeno[1,2-b]pyrazine-2,3-dicarbonitrile
6-Methoxy-9-oxo-9H-indeno[1,2-b]pyrazine-2,3-dicarbonitrile
6,7-Dimethoxy-9-oxo-9H-indeno[1,2-b]pyrazine-2,3-dicarbonitrile
8-Methyl-9-oxo-9H-indeno[1,2-b]pyrazine-2,3-dicarbonitrile
7,8-Dimethoxy-9-oxo-9H-indeno[1,2-b]pyrazine-2,3-dicarbonitrile
6-Methyl-9-oxo-9H-indeno[1,2-b]pyrazine-2,3-dicarbonitrile
5,8-Dimethoxy-9-oxo-9H-indeno[1,2-b]pyrazine-2,3-dicarbonitrile
7-Chloro-9-oxo-9H-indeno[1,2-b]pyrazine-2,3-dicarbonitrile
7-Fluoro-9-oxo-9H-indeno[1,2-b]pyrazine-2,3-dicarbonitrile
7-Hydroxy-9-oxo-9H-indeno[1,2-b]pyrazine-2,3-dicarbonitrile
2-cyano-9-oxo-9H-indeno[1,2-b]pyrazin-3-yl-cyanamide
3-(1-cyano-2-ethoxy-2-hydroxy-vinyl)-9-oxo-9H-indeno[1,2-b]pyrazine-2-carbonitrile
3-ethylsulfanyl-9-oxo-9H-indeno[1,2-b]pyrazine-2-carbonitrile
7-Chloro-9-methoxyimino-9H-indeno[1,2-b]pyrazine-2,3-dicarbonitrile
9-Allyloxyimino-7-chloro-9H-indeno[1,2-b]pyrazine-2,3-dicarbonitrile
6-Chloro-9-oxo-9H-indeno[1,2-b]pyrazine-2,3-dicarbonitrile
2-(2-cyano-9-oxo-9H-indeno[1,2-b]pyrazin-3-yl)-acetamide
9-(2-Phenoxy-ethoxyimino)-9H-indeno[1,2-b]pyrazine-2,3-dicarbonitrile 7-Chloro-9-(2-phenoxy-ethoxyimino)-9H-indeno[1,2-b]pyrazine-2,3-dicarbonitrile
9-Allyloxyimino-6-chloro-9H-indeno[1,2-b]pyrazine-2,3-dicarbonitrile
7-Fluoro-8-methyl-9-oxo-9H-indeno[1,2-b]pyrazine-2,3-dicarbonitrile
6,7-dichloro-9-oxo-9H-indeno[1,2-b]pyrazine-2,3-dicarbonitrile
6-ethyl-9-oxo-9H-indeno[1,2-b]pyrazine-2,3-dicarbonitrile
2-cyano-9-[hydroxyimino]-9H-indeno[1,2-b]pyrazine-3-carboxylic acid amide 9-Allyloxyimino-2-cyano-9H-indeno[1,2-b]pyrazine-3-carboxylic acid amide2-Cyano-9-ethoxyimino-9H-indeno[1,2-b]pyrazine-3-carboxylic acid amide 2-Cyano-9-(2-methoxy-ethoxyimino)-9H-indeno[1,2-b]pyrazine-3-carboxylic acid amide 2-Cyano-9-methoxyimino-9H-indeno[1,2-b]pyrazine-3-carboxylic acid amide 2-cyano-9-acetoxyimino-9H-indeno[1,2-b]pyrazine-3-carboxylic acid amide 2-cyano-9-oxo-9H-indeno[1,2-b]pyrazine-3-carboxylic acid amide (3-carbamoyl-2-cyano-indeno[1,2-b]pyrazin-9-ylidene-aminooxy)-acetic acid ethyl ester (3-carbamoyl-2-cyano-indeno[1,2-b]pyrazin-9-ylidene-aminooxy)-acetic acid

[2-(3-carbamoyl-2-cyano-indeno[1,2-b]pyrazin-9-ylideneaminooxy)-acetylamino]-acetic acid ethyl ester

[2-(3-carbamoyl-2-cyano-indeno[1, 2-b]pyrazin-9-ylideneaminooxy)-acetylamino]-acetic acid 7-chloro-3-hydroxy-9-oxo-9H-indeno[1,2-b]pyrazine-2-carbonitrile 9-[(aminocarbonyl)hydrazono]-7-chloro-9H-indeno[1,2-b]pyrazine-2,3-dicarbonitrile or a pharmaceutically acceptable salt thereof.

11. Compound according to claim 1 selected from the group consisting of:

2-cyano-9-[hydroxyimino]-9H-indeno[1,2-b]pyrazine-3-carboxylic acid amide 9-(methoxyimino)-9H-indeno[1,2-b]pyrazine-2,3-dicarbonitrile 9-Benzyloxyimino-9H-indeno[1,2-b]pyrazine-2,3-dicarbonitrile 9-Ethoxyimino-9H-indeno[1,2-b]pyrazine-2,3-dicarbonitrile 9-Phenoxyimino-9H-indeno[1,2-b]pyrazine-2,3-dicarbonitrile 8-Methyl-9-oxo-9H-indeno[1,2-b]pyrazine-2,3-dicarbonitrile 6-Methyl-9-oxo-9H-indeno[1,2-b]pyrazine-2,3-dicarbonitrile 5,8-Dimethoxy-9-oxo-9H-indeno[1,2-b]pyrazine-2,3-dicarbonitrile 7-Chloro-9-oxo-9H-indeno[1,2-b]pyrazine-2,3-dicarbonitrile 7-Fluoro-9-oxo-9H-indeno[1,2-b]pyrazine-2,3-dicarbonitrile 2-cyano-9-oxo-9H-indeno[1,2-b]pyrazine-3-carboxylic acid amide or a pharmaceutically acceptable salt thereof.

12. A pharmaceutical composition comprising a compound of formula (I)

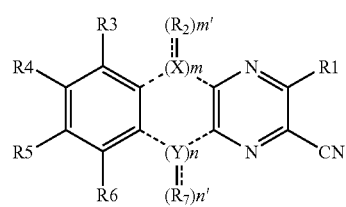

(I)

wherein:

m is 0; 1 or 2, wherein when m=0, —$(X(R_2)_{m'})_m$— is none so as to form an open ring or a single bond;

n is 0, 1 or 2, wherein when n=0, —$(Y(R_7)_{n'})_n$— is none so as to form an open ring or a single bond;

m' and n' are independently 1 or 2;

X is a carbon atom;

Y is a carbon atom;

wherein m+n=1;

=== is either a single or double bond, as appropriate;

— is either none or a single bond, as appropriate;

R1 is chosen from the group consisting of H, CN, Hal, OAlk, OH, NRCN, C(CN)=C(OH)(OAlk), NRR', -(Alk)$_p$-C(O)NRR', Heterocycle, Aryl, Heteroaryl, where Alk, Aryl, Heteroaryl, Heterocycle are optionally substituted by Hal, NRR', CN, OH, $CF_3$, Aryl, Heteroaryl, OAlk, and p is 0 or 1;

R3, R4, R5, R6 are each identical or different and are independently chosen from the group consisting of H, OAlk, Alk, Hal, NRR', CN, OH, $CF_3$, Aryl, Heteroaryl;

$R_2$ is chosen from the group consisting of H, O, OH, N—OH, N-Aryl, N-OAlk, N—O-Aryl, N—O-Alk-Aryl, N—NR—CONRR', N—O—CO-Alk, or 2 $R_2$ bound at the same X form together with that X an heterocycle; wherein said Alk, Aryl or heterocycle are optionally substituted by OAlk, Alk, Hal, NRR', CN, OH, $CF_3$, OAryl, —CO—(NR-Alk-CO)$_{p'}$—OAlk, —CO(NR-Alk-CO)$_{p'}$—OH, where p' is 0 or 1;

$R_7$ is chosen from the group consisting of H, O, OH, N—OH, N-Aryl, N-OAlk, N—O-Aryl, N—O-Alk-Aryl, N—NR—CONRR', N—O—CO-Alk, or 2 $R_7$ bound at the same Y form together with that Y an heterocycle; wherein said Alk, Aryl or heterocycle are optionally substituted by OAlk, Alk, Hal, NRR', CN, OH, $CF_3$, OAryl, —CO—(NR-Alk-CO)$_{p'}$—OAlk, —CO(NR-Alk-CO)$_{p'}$—OH, where p' is 0 or 1;

R and R' are each identical or different and are independently chosen from the group consisting in H, Alk, wherein Alk is optionally substituted by Hal, NRR', CN, OH, $CF_3$, Aryl, Heteroaryl;

wherein:

the aryl is an aromatic monocyclic or multicyclic hydrocarbon ring system of 6 to 14 carbon atoms, the heteroaryl is a 5 to 10 membered aromatic monocyclic or bicyclic, wherein the ring comprises from one to three heteroatoms individually selected from the group consisting of nitrogen, oxygen and sulphur; and the heterocycle is a saturated, partially unsaturated; non-aromatic stable 5 to 10 membered monocyclic or bicyclic ring, wherein the ring comprises from one to three heteroatoms individually selected from the group consisting of oxygen, nitrogen, sulphur, phosphorus and selenium, or a pharmaceutically acceptable salt thereof;

and a pharmaceutically acceptable excipient;

and wherein the compound of formula (I) cannot be a compound in which R3, R4, R5 and R6=H, R1=CN, —$(X(R_2)_{m'})_m$— is C=O and —$(Y(R_7)_{n'})_n$— is a single bond and a compound in which R3, R4, R5 and R6=H, R1=CN, and —$(Y(R_7)_{n'})_n$— is C=O and $(X(R_2)_{m'})_m$— is a single bond.

13. Pharmaceutical composition according to claim 12, wherein,

R1 is chosen from the group consisting of H, CN, Hal, OAlk, OH, NRCN, C(CN)=C(OH)(OAlk), NRR', (Alk)$_p$-C(O)NRR', Heterocycle, where Alk is optionally substituted by OAlk and where Heterocycle is optionally substituted by Hal where p is 0 or 1;

R3, R4, R5, R6 are each identical or different and are independently chosen from the group consisting of H, OAlk, Alk, Hal;

—(Y(R$_7$)$_{n'}$)$_n$— is a single bond or Y represents a carbon atom;

R$_2$ is chosen from the group consisting of H, O;

R$_7$ is chosen from the group consisting of H, O, OH, N—OH, N—OAlk, N—O-Aryl, N—O-Alk-Aryl, N—O-AlkOAryl, N—O-Alk-CO(NR-Alk-CO)p'-OAlk, N—O-Alk-CO(NR-Alk-CO)p'-OH, —N—NR—CONRR', N—CO-Alk, or 2 R$_7$ bound at the same Y form together with that Y an heterocycle where p' is 0 or 1;

R and R' are each identical or different and are independently chosen from the group consisting of H, Alk.

14. Pharmaceutical composition according to claim 12, wherein said compound of formula (I) is chosen from the group consisting of:

9-oxo-9H-indeno[1,2-b]pyrazine-2,3-dicarbonitrile
9-hydroxy-3-methoxy-9H-indeno[1,2-b]pyrazine-2-carbonitrile
3-methoxy-9-oxo-9H-indeno[1,2-b]pyrazine-2-carbonitrile
3-dimethylamino-9-oxo-9H-indeno[1,2-b]pyrazine-2-carbonitrile
3-(2-methoxy-ethoxy)-9-oxo-9H-indeno[1,2-b]pyrazine-2-carbonitrile
3-hydroxy-9-oxo-9H-indeno[1,2-b]pyrazine-2-carbonitrile
3-amino-9-oxo-9H-indeno[1,2-b]pyrazine-2-carbonitrile
3-(4,4-difluoro-piperidin-1-yl)-9-oxo-9H-indeno[1,2-b]pyrazine-2-carbonitrile
3-chloro-9-oxo-9H-indeno[1,2-b]pyrazine-2-carbonitrile
9-(1',3'-dioxolan-2'-yl)-9H-indeno[1,2-b]pyrazine-2,3-dicarbonitrile
2-cyano-9-[hydroxyimino]-9H-indeno[1,2-b]pyrazine-3-carboxylic acid amide
9-[hydroxyimino]-9H-indeno[1,2-b]pyrazine-2,3-dicarbonitrile
9-(methoxyimino)-9H-indeno[1,2-b]pyrazine-2,3-dicarbonitrile
9-(Allyloxyimino)-9H-indeno[1,2-b]pyrazine-2,3-dicarbonitrile
9-Benzyloxyimino-9H-indeno[1,2-b]pyrazine-2,3-dicarbonitrile
9-Ethoxyimino-9H-indeno[1,2-b]pyrazine-2,3-dicarbonitrile
9-Phenoxyimino-9H-indeno[1,2-b]pyrazine-2,3-dicarbonitrile
9-[phenylimino]-9H-indeno[1,2-b]pyrazine-2,3-dicarbonitrile
6-Methoxy-9H-indeno[1,2-b]pyrazine-2,3-dicarbonitrile
6,7-Dimethoxy-9H-indeno[1,2-b]pyrazine-2,3-dicarbonitrile
8-Methyl-9H-indeno[1,2-b]pyrazine-2,3-dicarbonitrile
7,8-Dimethoxy-9H-indeno[1,2-b]pyrazine-2,3-dicarbonitrile
6-Methyl-9H-indeno[1,2-b]pyrazine-2,3-dicarbonitrile
5,8-Dimethoxy-9H-indeno[1,2-b]pyrazine-2,3-dicarbonitrile
6-Methoxy-9-oxo-9H-indeno[1,2-b]pyrazine-2,3-dicarbonitrile
6,7-Dimethoxy-9-oxo-9H-indeno[1,2-b]pyrazine-2,3-dicarbonitrile
8-Methyl-9-oxo-9H-indeno[1,2-b]pyrazine-2,3-dicarbonitrile
7,8-Dimethoxy-9-oxo-9H-indeno[1,2-b]pyrazine-2,3-dicarbonitrile
6-Methyl-9-oxo-9H-indeno[1,2-b]pyrazine-2,3-dicarbonitrile
5,8-Dimethoxy-9-oxo-9H-indeno[1,2-b]pyrazine-2,3-dicarbonitrile
7-Chloro-9-oxo-9H-indeno[1,2-b]pyrazine-2,3-dicarbonitrile
7-Fluoro-9-oxo-9H-indeno[1,2-b]pyrazine-2,3-dicarbonitrile
7-Methoxy-9-oxo-9H-indeno[1,2-b]pyrazine-2,3-dicarbonitrile
7-Hydroxy-9-oxo-9H-indeno[1,2-b]pyrazine-2,3-dicarbonitrile
2-cyano-9-oxo-9H-indeno[1,2-b]pyrazin-3-yl-cyanamide
3-(1-cyano-2-ethoxy-2-hydroxy-vinyl)-9-oxo-9H-indeno[1,2-b]pyrazine-2-carbonitrile
3-ethylsulfanyl-9-oxo-9H-indeno[1,2-b]pyrazine-2-carbonitrile
7-Chloro-9-methoxyimino-9H-indeno[1,2-b]pyrazine-2,3-dicarbonitrile
9-Allyloxyimino-7-chloro-9H-indeno[1,2-b]pyrazine-2,3-dicarbonitrile
6-Chloro-9-oxo-9H-indeno[1,2-b]pyrazine-2,3-dicarbonitrile
2-(2-cyano-9-oxo-9H-indeno[1,2-b]pyrazin-3-yl)-acetamide
9-(2-Phenoxy-ethoxyimino)-9H-indeno[1,2-b]pyrazine-2,3-dicarbonitrile 7-Chloro-9-(2-phenoxy-ethoxyimino)-9H-indeno[1,2-b]pyrazine-2,3-dicarbonitrile
9-Allyloxyimino-6-chloro-9H-indeno[1,2-b]pyrazine-2,3-dicarbonitrile
7-Fluoro-8-methyl-9-oxo-9H-indeno[1,2-b]pyrazine-2,3-dicarbonitrile
6,7-dichloro-9-oxo-9H-indeno[1,2-b]pyrazine-2,3-dicarbonitrile
6-ethyl-9-oxo-9H-indeno[1,2-b]pyrazine-2,3-dicarbonitrile
2-cyano-9-[hydroxyimino]-9H-indeno[1,2-b]pyrazine-3-carboxylic acid amide
9-Allyloxyimino-2-cyano-9H-indeno[1,2-b]pyrazine-3-carboxylic acid amide2-Cyano-9-ethoxyimino-9H-indeno[1,2-b]pyrazine-3-carboxylic acid amide
2-Cyano-9-(2-methoxy-ethoxyimino)-9H-indeno[1,2-b]pyrazine-3-carboxylic acid amide
2-Cyano-9-methoxyimino-9H-indeno[1,2-b]pyrazine-3-carboxylic acid amide
2-cyano-9-acetoxyimino-9H-indeno[1,2-b]pyrazine-3-carboxylic acid amide
2-cyano-9-oxo-9H-indeno[1,2-b]pyrazine-3-carboxylic acid amide
(3-carbamoyl-2-cyano-indeno[1,2-b]pyrazin-9-ylideneaminooxy)-acetic acid ethyl ester
(3-carbamoyl-2-cyano-indeno[1,2-b]pyrazin-9-ylideneaminooxy)-acetic acid
[2-(3-carbamoyl-2-cyano-indeno[1,2-b]pyrazin-9-ylideneaminooxy)-acetylamino]-acetic acid ethyl ester
[2-(3-carbamoyl-2-cyano-indeno[1,2-b]pyrazin-9-ylideneaminooxy)-acetylamino]-acetic acid
7-chloro-3-hydroxy-9-oxo-9H-indeno[1,2-b]pyrazine-2-carbonitrile
9-[(aminocarbonyl)hydrazono]-7-chloro-9H-indeno[1,2-b]pyrazine-2,3-dicarbonitrile
or a pharmaceutically acceptable salt thereof.

15. Process of preparation of a compound according to claim 1 comprising the step of reacting a corresponding compound of formula (II)

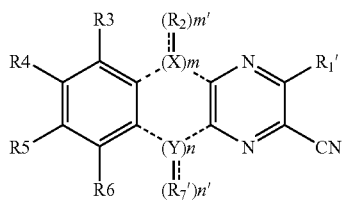
(II)

wherein R3, R4, R5, R6, X, Y, m, m', n, n' are defined as in formula (I) and $R_7'$ is $R_7$ as defined in formula (I) or a precursor thereof and R1' is R1 as defined in formula (I) or a precursor thereof.

16. Process according to claim 15, wherein R1' is CN.

17. Process according to claim 15, wherein —$(Y(R_7)_{n'})_n$— is —C(=O)—.

18. Process according to claim 15, wherein said compound of formula (II) is obtained from a corresponding compound of formula (III) or (III')

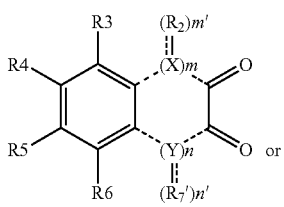
(III)

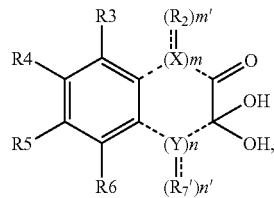
(III')

wherein R3, R4, R5, R6, X, Y, m', n, n' are defined as in formula (I) and $R_7'$ is defined as in formula (II).

19. Process according to claim 18, wherein when R1'=CN, this step is carried out in the presence of diaminomaleodinitrile.

20. Process according to claim 15, wherein said compound of formula (II) is obtained from a corresponding compound of formula (IV)

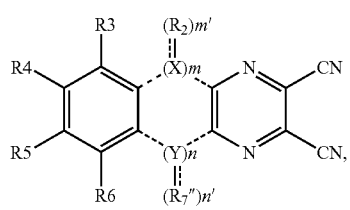
(IV)

wherein R3, R4, R5, R6, X, Y, m, m', n, n' are defined as in formula (I) and $R_7''$ represents $R_7'$ or a precursor thereof, if appropriate.

* * * * *